US012559535B2

(12) United States Patent
Vermaelen

(10) Patent No.: US 12,559,535 B2
(45) Date of Patent: Feb. 24, 2026

(54) METHOD FOR THE IN VITRO DIFFERENTIATION AND MATURATION OF DENDRITIC CELLS FOR THERAPEUTIC USE

(71) Applicant: Universiteit Gent, Ghent (BE)

(72) Inventor: Karim Vermaelen, Wondelgem (BE)

(73) Assignee: Universiteit Gent, Ghent (BE)

( * ) Notice: Subject to any disclaimer, the term of this patent is extended or adjusted under 35 U.S.C. 154(b) by 1398 days.

(21) Appl. No.: 17/253,886

(22) PCT Filed: Jun. 20, 2019

(86) PCT No.: PCT/EP2019/066398
§ 371 (c)(1),
(2) Date: Dec. 18, 2020

(87) PCT Pub. No.: WO2019/243537
PCT Pub. Date: Dec. 26, 2019

(65) Prior Publication Data
US 2021/0139852 A1    May 13, 2021

(30) Foreign Application Priority Data
Jun. 21, 2018    (EP) .................................... 18179073

(51) Int. Cl.
*C07K 14/705*    (2006.01)
*A61K 39/00*    (2006.01)
*A61K 40/19*    (2025.01)
*A61K 40/24*    (2025.01)
*C12N 5/0784*    (2010.01)

(52) U.S. Cl.
CPC ............ *C07K 14/705* (2013.01); *A61K 40/19* (2025.01); *A61K 40/24* (2025.01); *C12N 5/0639* (2013.01); *A61K 2039/5154* (2013.01); *A61K 2121/00* (2013.01); *C12N 2500/36* (2013.01); *C12N 2501/051* (2013.01); *C12N 2501/22* (2013.01); *C12N 2501/2304* (2013.01); *C12N 2501/24* (2013.01); *C12N 2510/00* (2013.01)

(58) Field of Classification Search
CPC ............ C12N 5/0639; C12N 2501/051; C12N 2501/22; C12N 2501/2304; C12N 2501/24; C12N 2510/00; C12N 2500/36; C12N 2500/99; C12N 2501/999; A61K 39/001191; A61K 2039/5154; A61K 39/4615; A61K 39/4622; A61K 39/464491; A61K 35/00; A61K 40/19; A61K 40/24; A61K 2121/00; C07K 14/705
See application file for complete search history.

(56) References Cited

FOREIGN PATENT DOCUMENTS

| | | |
|---|---|---|
| EP | 1806395 A1 | 1/2006 |
| EP | 2829600 A1 | 7/2013 |
| WO | 2007078196 A1 | 7/2007 |

OTHER PUBLICATIONS

Ten Brinke A et al. Monophosphoryl lipid A plus IFN gamma maturation of dendritic cells induces antigen-specific CD8+ cytotoxic T cells with high cytolytic potential. Cancer Immunol Immunother. Aug. 2010;59(8):1185-95. doi: 10.1007/s00262-010-0843-z. Epub Mar. 25, 2010. PMID: 20336295. (Year: 2010).*
Jarnjak-Jankovic S, Hammerstad H, Saebøe-Larssen S, Kvalheim G, Gaudernack G. A full scale comparative study of methods for generation of functional Dendritic cells for use as cancer vaccines. BMC Cancer. Jul. 3, 2007;7:119. doi: 10.1186/1471-2407-7-119. PMID: 17608923; PMCID: PMC1931601. (Year: 2007).*
Michiels A, Tuyaerts S, Bonehill A, Corthals J, Breckpot K, Heirman C, Van Meirvenne S, Dullaers M, Allard S, Brasseur F, van der Bruggen P, Thielemans K. Electroporation of immature and mature dendritic cells: implications for dendritic cell-based vaccines. Gene Ther. May 2005; 12(9):772-82. (Year: 2005).*
Jarnjak-Jankovic S, Pettersen RD, Saebøe-Larssen S, Wesenberg F, Olafsen MR, Gaudernack G. Preclinical evaluation of autologous dendritic cells transfected with mRNA or loaded with apoptotic cells for immunotherapy of high-risk neuroblastoma. Cancer Gene Ther. Aug. 2005; 12(8):699-707. (Year: 2005).*
Mu LJ, Gaudernack G, Saebøe-Larssen S, Hammerstad H, Tierens A, Kvalheim G. A protocol for generation of clinical grade mRNA-transfected monocyte-derived dendritic cells for cancer vaccines. Scand J Immunol. Nov. 2003;58(5):578-86. doi: 10.1046/j.1365-3083.2003.01333.x. PMID: 14629630. (Year: 2003).*
Tawab A, Fan Y, Read EJ, Kurlander RJ. Effect of ex vivo culture duration on phenotype and cytokine production by mature dendritic cells derived from peripheral blood monocytes. Transfusion. Mar. 2009;49(3):536-47. doi: 10.1111/j.1537-2995.2008.02020.x. PMID: 19243546; PMCID: PMC3859301. (Year: 2009).*
Büchler T, Kovárová L, Musilová R, Bourková L, Ocadlíková D, Buliková A, Hanák L, Michálek J, Hájek R. Generation of dendritic cells using cell culture bags—description of a method and review of literature. Hematology. Jun. 2004; 9(3):199-205. doi: 10.1080/10245330410001701486. PMID: 15204101. (Year: 2004).*
International Search Report in reference to co-pending European Patent Application No. PCT/EP2019/066398 filed Jun. 20, 2019.
Mu, et al., "A Protocol for Generation of Clinical Grade mRNA-Transfected Monocyte-Derived Dendritic Cells for Cancer Vaccine", Scandinavian Journal of Immunology, vol. 58, pp. 578-586, 2003.
Massa, et al., "Different maturation cocktails provide dendritic cells with different chemoattractive properties", Journal of Translational Medicine, pp. 1-16, 2015.
Kalady, et al., "Enhanced Dendritic Cell Antigen Presentation in RNA-Based Immunotherapy", Journal of Surgical Research, vol. 105, pp. 17-24, 2002.

(Continued)

*Primary Examiner* — Janet L Andres
*Assistant Examiner* — Carol Ann Chase
(74) *Attorney, Agent, or Firm* — DINSMORE & SHOHL LLP

(57) ABSTRACT

The present invention relates to an accelerated method to generate high yields of type-1 polarizing mRNA loaded dendritic cells for use in immunotherapy, and in particular for use in cancer vaccination.

24 Claims, 29 Drawing Sheets

Specification includes a Sequence Listing.

(56) References Cited

OTHER PUBLICATIONS

Brabants, et al., "An accelerated, clinical-grade protocol to generate high yields of type 1-polarizing messenger RNA-loaded dendritic cells for cancer vaccination", Cytotherapy, vol. 20, pp. 1164-1181, 2018.

Massa, et al., "Fast Dendritic Cells Stimulated with Alternative Maturation Mixtures Induce Polyfunctional and Long-Lasting Activation of Innate and Adaptive Effector Cells with Tumor-Killing Capabilities", The Journal of Immunology, vol. 190, pp. 3328-3337, 2013.

Okada, et al., "Induction of CD8+ T-Cell Responses Against Novel Glioma-Associated Antigen Peptides and Clinical Activity by Vaccinations With a-Type 1 Polarized Dendritic Cells and Polyinsosinic-Polycytidylic Acid Stabilized by Lysine and Carboxymethylcellulose in Ptients With Recurrent Malignany Giloma", Journal of Clinical Oncology, vol. 29, No. 3, pp. 330-336, Jan. 20, 2011.

Paustian, et al., "Effect of multiple activation stimuli on the generation of Th1-polarizing dendritic cells", Human Immunology, vol. 72, pp. 24-31, 2011.

Ponsaerts, et al., "Cancer immunotherapy using RNA-loaded dendritic cells", Clinical Exp. Immunol., vol. 134, pp. 378-384, 2003.

Prima, et al., "COX2/mPGES1/PGE$_2$ pathway regulates PD-L1 expression in tumor-associated macrophages and myeloid-derived suppressor cells", PNAS CrossMark, vol. 114, No. 5, pp. 1117-1122, Jan. 31, 2017.

Rouas, et al., "Dendritic Cells Generated in Clinical Grade Bags Strongly Differ in Immune Functionality When Compared With Classical DCs Generated in Plates", Journal Immunother, Basic Study, vol. 33, No. 4, pp. 352-363, May 2010.

Samson, et al., "The Second Extracellular Loop of CCR5 Is the Major Determinant of Ligand Specificity", The Journal of Biological Chemistry, vol. 272, No. 40, pp. 24934-24941, 1997.

Van Schijindel, et al., "Monophosphoryl lipid A plus IFN$\gamma$ maturation of dendritic cells induces antigen-specific CD8+ cytotoxic T cells with high cytolytic potential", Cancer Immunol Immunother, vol. 59, pp. 1185-1195, 2010.

Hansen, et al., "Comparison of clinical grade type 1 polarized and standard matured dendritic cells for cancer Immunotherapy", Vaccine, vol. 31, pp. 639-646, 2013.

Truxova, et al., "Day 3 Poly (I:C)-activated dendritic cells generated in CellGro for use in cancer immunotherapy trials are fully comparable to standard Day 5 DCs", Immunology Letters, vol. 160, pp. 39-49, 2014.

Tuyaerts, et al., "Induction of Influenza Matrix Protein 1 and MelanA-specific T lymphocytes in vitro using mRNA-electroporated dendritic cells", Cancer Gene Therapy, vol. 10, pp. 696-706, 2003.

Valmori, et al., "Diversity of the Fine Specificity Displayed by HLA-A*0201-Restricted CTL Specific for the Immunodominant Melan-A/MART-1 Antigenic Peptide", The Journal of Immunology, vol. 161, pp. 6956-6962, 1998.

Van Driessche, et al., "Clinical-grade manufacturing of autologous mature mRNA-electroporated dendritic cells and safety testing in acute myeloid leukemia patients in a phase I dose-escalation clinical trial", Cytotherapy, vol. 11, No. 5, pp. 653-668, 2009.

Van Lint, et al., "Optimized dendritic cell-based immunotherapy for melanoma: the TriMix-formula", Cancer Immunol Immunother, vol. 63, pp. 959-967, 2014.

Yamazaki, et al., "CCR6 Regulates the Migration of Inflammatory and Regulatory T Cells", The Journal of Immunology, pp. 8392-8401, 2008.

Yoshie, et al., "CCR4 and its ligands: from bench to bedside", International Immunology, vol. 27, No. 1, pp. 11-20, 2014.

Boccaccio, et al., "Identification of a Clinical-Grade Maturation Factor for Dendritic Cells", Journal of Immunotherapy, vol. 25, pp. 88-96, 2002.

Bonehill, et al., "Messenger RNA-Electroporated Dendritic Cells Presenting MAGE-A3 Simultaneously in HLA Class I and Class II Molecules[1]", The Journal of Immunology, pp. 6649-6657, 2004.

Bonehill, et al., "Single-Step Antigen Loading and Activation of Dendritic Cells by mRNA Electroporation for the Purpose of Therapeutic Vaccination in Melanoma Patients", Cancer Therapy: Preclinical, vol. 10, pp. 3366-3375, 2009.

Colantonio, et al., "Modulation of chemokine receptor expression and chemotactic responsiveness during differentiation of human naive T cells into Th1 or Th2 cells", European Journal of Immunology, vol. 32, pp. 1264-1273, 2002.

Dauer, et al., "Mature Dendritic Cells Derived from Human Monocytes Within 48 Hours: A Novel Strategy for Dendritic Cell Differentiation from Blood Precursors", The Journal of Immunology, vol. 170, pp. 4069-4076, 2003.

Groom, et al., "CXCR3 ligands: redundant, collaborative and antagonistic functions", Immunology and Cell Biology, vol. 89, pp. 207-215, 2011.

Gregg, et al., "Rationally Designed TLR4 Ligands for Vaccine Adjuvant Discovery", American Society for Microbiology, vol. 8, Issue 3, pp. 1-14, 2017.

Jarnjak-Jankovic, et al., "A full scale comparative study of methods for generation of functional Dendritic cells for use as cancer vaccines", BMC Cancer, pp. 1-9, Jul. 3, 2007.

Gato-Canas, et al., "PDL1 Signals through Conserved Sequence Motifs to Overcome Interferon-Mediated Cytotoxicity", Cell Reports, vol. 20, pp. 1818-1829, Aug. 22, 2017.

Johnson, et al., "Characterization of a Nontoxic Monophosphoryl Lipid A", Reviews of Infectious Diseases, vol. 9, Supplement 5, pp. S512-S516, Sep.-Oct. 1987.

Kalinski, et al., "Prostaglandin E$_2$ Induces the Final Maturation of IL-12-Deficient CD1a +CD83+ Dendritic Cells: The Levels of IL-12 Are Determined During the Final Dendritic Cell Maturation and Are Resistant to Further Modulation", The Journal of Immunology, pp. 2804-2809, 1998.

Kolanowski, et al., "Comparison of media and serum supplementation for generation of monophosphoryl lipid A/Interferon-y-matured type I dendritic cells for immunotherapy", Cytotherapy, vol. 16, pp. 826-834, 2014.

Kvistborg, et al., "Fast generation of dendritic cells", Cellular Immunology, vol. 260, pp. 56-62, 2009.

Kyte, et al., "Preclinical full-scale evaluation of dendritic cells transfected with autologous tumor-mRNA for melanoma vaccination", Cancer Gene Therapy, vol. 12, pp. 579-591, 2005.

Lebre, et al., "Differential expression of inflammatory chemokines by Th1-and Th2-call promoting dendritic cells: A role for different mature dendritic cell populations in attracting appropriate effector cells to peripheral sites of Inflammation", Immunology and Cell Biology, vol. 83, pp. 525-535, 2005.

Mailliard, et al., "a-Type-1 Polarized Dendritic Cells: A Novel Immunization Tool with Optimized CTL-inducing Activity", Cancer Research, vol. 64, pp. 5934-5937, Sep. 1, 2004.

* cited by examiner

Y-axis: Concentration (pg/ml)

after cryopreservation and thawing

Viability (%)

4 hours after EP

Viability (%)

Short DC culture: 3 days GM-CSF / IL-4; 24 hours MPLA (2.5µg/mL) and IFN-γ (1000U/mL)

1000U/mL GM-CSF; 1000U/mL IL-4; 2x10e6 monocytes/mL
1000U/mL GM-CSF; 1000U/mL IL-4; 1x10e6 monocytes/mL
2000U/mL GM-CSF; 1000U/mL IL-4; 1x10e6 monocytes/mL

FIG. 12B

METHOD FOR THE IN VITRO DIFFERENTIATION AND MATURATION OF DENDRITIC CELLS FOR THERAPEUTIC USE

CROSS-REFERENCE TO RELATED APPLICATIONS

This application is a § 371 national stage entry of PCT/EP2019/066398, filed Jun. 20, 2019, which claims priority to EP 18179073.4, filed Jun. 21, 2018, the entire contents of which are incorporated herein by reference in their entirety.

SEQUENCE LISTING

A Sequence Listing in ASCII format, having the file name 2021-07-28_ReplacementSequenceListing_UNG0004PA_P2018-021.txt, created Jul. 27, 2021 (4096 bytes) is incorporated herein by reference in its entirety.

FIELD OF THE INVENTION

The present invention relates to an accelerated method to generate high yields of type-1 polarizing mRNA loaded dendritic cells for use in immunotherapy, and in particular for use in cancer vaccination.

BACKGROUND TO THE INVENTION

Since the discovery of dendritic cells more than 40 years ago, the translation of these cells' unique biological properties into medical applications has remained a challenge. Most efforts have focused on bringing DCs to the clinic in the shape of vaccines against cancer. This is based on the DC's capacity to evoke T-cell responses against tumor antigens, leading to protection against tumor development or even eradication of established tumors, as has been demonstrated in countless preclinical models.

At the basis of this effect are a set of unique biological properties, which have been summarized as the "4-signal" concept: (1) presentation of very high amounts of processed antigen on major histocompatibility class (MHC) molecules, (2) upregulation of a large array of T-cell costimulatory molecules on the cell surface, (3) release of cytokines driving proper polarization of the T-cell response, and (4) provision of additional signals that program the tissue-homing pattern of elicited T-cell effectors. In the specific context of anti-tumor immunity, DCs can pick up dead cells by means of specialized receptors such as DNGR-1, leading to cross-presentation of MHC I and priming of antigen-specific cytotoxic T-cells. High expression of the T-cell costimulatory molecule CD40 boosts the magnitude of CD4+ and CD8+ T-cell expansion, resulting in enhanced tumor protection and conversion of tolerance into immunity, while upregulation of CD70 is essential for generation of powerful and long-lasting memory cytotoxic T-cell responses. In contrast, expression of T-cell inhibitory receptors or checkpoint ligands such as programmed death ligand-1 (PD-L1) should be minimal on the DCs surface.

Next, the ability to secrete sufficient amounts of bioactive IL-12 at the time of T-cell contact is essential to drive the type-1 polarized response necessary for optimal tumor control, while also supporting NK-cell effector functions. In addition, the pattern of chemokines released by the DC dictates which type of T-cells will be recruited, i.e. in the case of anti-tumor immunity preferentially type-1 polarized effectors, rather than T-helper (Th) 2 cells (with tumor-supporting potential) or immune suppressive regulatory T-cells (T-regs).

From this knowledge, it is clear that designing the ideal DC-based cancer vaccine requires maximal control and optimization of all of these critical parameters. A correct DC activation or maturation status is essential in determining T-cell outcome, since immature DCs (iDCs) are largely ineffective in stimulating T-cell responses and can even promote T-cell tolerance.

Therefore, thoughtful consideration is warranted in selecting strong activation stimuli to generate fully potent mature DCs, while also avoiding the phenomenon of DC "exhaustion".

Toll-like receptor (TLR) ligands are among the strongest triggers for DC maturation and can be either exogenous (i.e. pathogen-derived) or endogenous (danger-associated molecules from tissue damage or cell death). Despite this knowledge, one of the most used maturation strategies consists of exposing monocyte-derived DCs to a combination of inflammatory mediators that includes tumor necrosis factor-alpha (TNF-α), interleukin-1beta (IL-1β), interleukin-6 (IL-6), and prostaglandin E2 (PGE2), as first described by Jonuleit et al. The value of adding PGE2 lies in the observation that it can further increase DC yield, maturation, and migration (Jonuleit et al. 1997). However, it has also been shown that PGE2 impairs the capacity of DCs to secrete bioactive IL-12p70, and to shift T-helper cell polarization towards Th2-rather than Th1-development Kalinski et al. 1998).

Since then, many alternative strategies have been explored in order to maximize the capacity of DCs to induce type-1 polarized responses. Mailliard et al developed a protocol where DCs were matured in the presence of the pro-inflammatory cytokines TNF-α, IL-1β, IFN-γ and interferon-alpha (IFN-α), together with the TLR3 agonist poly (I:C) (U.S. Pat. Nos. 7,972,847; 8,691,570). In comparison to the "standard" TNF-α, IL-1β, IL-6, and PGE2-matured DCs, these α-type-1 polarized DCs (αDC1) produced higher levels of IL-12p70 and induced a more robust expansion of long-lived cytolytic Tcells (CTLs) against melanoma-associated antigens (Maillard et al. 2004). Although these αDC1 cells have already been used in a clinical trial for patients with recurrent malignant glioma (Okada et al. 2011), the complexity of the maturation "cocktail" poses significant challenges in terms of implementation in a good manufacturing practice (GMP)-compliant production process.

A simpler alternative involves combining a TLR4 ligand with interferon-gamma (IFN-γ). Lipopolysaccharide (LPS) is one of the strongest innate stimuli for DC maturation, triggering massive production of immunostimulatory cytokines such as IL-12. However, LPS-stimulated DCs become refractory to further IL-12 release when subsequently engaging in cognate interactions with T-cells in vivo. This "exhaustion" phenomenon can be offset by co-exposure of DCs to IFN-γ, enabling the production of a "second burst" of IL-12 upon triggering by T-cell contact or artificial CD40-ligation (Paustian et al. 2011). Still, the use of LPS raises issues for large-scale cellular therapy applications due to its toxicity and the absence of a GMP formulation. The LPS-derivate monophosphoryl lipid A (MPLA) however has been approved for clinical use (Boccaccio et al. 1997), as a result of acid hydrolysis of LPS which preserves immunostimulatory characteristics but significantly attenuates toxicity levels. MPLA is an integral ingredient of adjuvant formulations of current mass-produced vaccines. It has been reported that both MPLA/IFN-γ DCs and α-type-1 polarized DCs are equally superior in comparison to TNF-α, IL-1β, IL-6, and PGE2-matured DCs in terms of secretion of IL-12p70 and chemokines attracting effector T-cells, and also superior in terms of CD4+ and CD8+ T-cell priming capacity (Hansen et al. 2013). The MPLA/IFN-γ DC maturation approach has been further explored by the group of Ten Brinke et al whereby monocytes cultured for 8 days in the presence of GM-CSF and IL-4 received a maturation boost during the last 2 days of culture. After harvest, the resulting DCs exhibited the capacity to induce de novo Th1 polarization as well as priming of antigen-specific CD8+ T-cells with high cytolytic activity (Ten Brinke et al. 2007; WO2007/078196; ten Brinke et al. 2010), while retaining the ability to migrate towards CCR7 ligands. This DC culture protocol has been further investigated with regards to possible clinical implementation, with additional studies showing the detrimental impact of human serum on DC maturation and migration in this setting (Kolanowski et al. 2014).

Next to the right type of maturation stimulus, the antigen loading modality is an important determinant of clinical applicability. Passive loading of DCs with immunogenic peptides, as typically used for functional testing in the above mentioned studies, implies prior knowledge of immunodominant epitopes for each candidate antigen considered, and imposes specific restrictions in terms of the human leukocyte antigen (HLA)-type of eligible patients. An alternative exploiting the high antigen uptake capacity of immature DCs is incubation with tumor lysate. However this requires sufficient quantities of patient tumor material, which again restricts feasibility in metastatic disease where only small biopsies or cytological samples are usually available. Loading DCs with full length mRNA encoding tumor antigens is now widely recognized as an elegant way to induce presentation of a broad array of possible epitopes. It also offers the opportunity to co-introduce RNA constructs that can optimize the immunogenic power of the DC (Van Lint et al. 2014). This is typically achieved by electroporation of the cells, the flipside of this approach being the risk of considerable cell loss, hereby compromising the possibility to administer sufficient vaccine doses to the patient (Tuyaerts et al. 2003; Ponsaerts et al. 2003; Bonehill et al. 2004).

An important additional aspect in terms of vaccine production is the duration of cell culture. For monocyte-derived DCs, this has traditionally been in the range of 7 to 8 days, implying repeated supplementation of the cultures with fresh medium and cytokines. In the demanding context of a GMP production environment, this translates into increased costs in terms of consumables as well as operator intervention. Several groups have demonstrated that fully functional DCs can be differentiated from monocytes using accelerated culture protocols (Jarnjak-Jankovic et al. 2007; Dauer et al. 2003; Kvistborg et al. 2009; Massa et al. 2013; Truxova et al. 2014; EP2829600).

A final practical consideration is the option to use a closed system cell culture: this constitutes another advantage in terms of GMP requirements and allows to transpose the production process to commercially available automated cell culture devices.

With these considerations in mind, it was the aim of the present invention to develop a process for the production of a clinical-grade DC based cancer vaccine, hereby reuniting for the first time several key assets in one and the same production method: accelerated culture time and taking advantage of a GMP-compatible type-1-polarizing maturation cocktail, in combination with antigen loading by mRNA electroporation. Moreover, it was demonstrated that this can be achieved using a closed culture system in GMP-compliant cell culture bags, in serum-free conditions with maximal use of GMP-certified or pharmaceutical-grade ingredients.

The performance of the method according to the present invention was compared to a widely established "standard" 8-day culture of monocyte-derived DCs matured with the combination of TNF-a and PGE2. This maturation cocktail is well-known by those skilled in the art, and is a simplified version of the original classical mono-DC maturation cocktail described by Jonuleit et al comprising TNF-a, PGE2, IL-1b and IL-6.

Importantly, and in contrast to many previous reports and to closely mimic a real-life vaccination setting, all of the functional assays with electroporated DCs in the present invention were performed after cryopreservation and thawing rather than using freshly manipulated cells.

Compared to the standard protocol, the method of the present invention delivers higher yields of DCs which are phenotypically and functionally superior. Surprisingly, we found a strongly reduced expression of the T-cell suppressive checkpoint ligand PD-L1 on the DCs generated according to the present invention compared to those obtained with the classical protocol. Moreover, expression further increased on classical DCs after thawing of cryopreserved aliquots, and this was not the case with aliquots of thawed DC obtained with the method of the present invention. This is a crucial observation with respect to the cells that will actually be injected into the patient, where expression of this immunosuppressive ligand should be as low as achievable.

SUMMARY OF THE INVENTION

The present invention relates to an in vitro method for the generation of mature, preferably autologous, clinical grade dendritic cells in a closed system (such as a culture with one or more sterile connections) and suitable for vaccination of e.g. cancer patients. In one embodiment, the method comprises essentially the generation (e.g. in a closed system) of mature clinical grade dendritic cells by differentiation of monocytes obtained from a leukapheresis using clinical grade cytokines, preferably GM-CSF and IL-4, combined with further maturation of the DCs thus obtained by additional exposure to a combination of maturation factors, preferably clinical-grade IFN-g and the detoxified derivative of endotoxin, MPLA.

The obtained product comprising mature dendritic cells produced/generated within about 4 days of total in vitro culture time (preferably within about 3 days to about 5 days culture), are thereafter loaded with one or more antigens, in particular tumor-associated antigens (TAA). This fast method according to the invention is able to generate large number of DC from leukapheresis products preferably in a closed system using serum-free medium.

In one embodiment, the method according to the invention comprises the following steps:

obtaining from a patient a mononuclear cell leukapheresis product, isolation of monocytes from the leukapheresis, incubating the monocytes with clinical grade cytokines, preferably suitable amounts of GM-CSF and IL-4 for the differentiation into dendritic cells, addition of maturation factors MPLA and IFN-g for final maturation of the monocyte-derived dendritic cells, and recovering the obtained cells and transfecting them with a nucleic acid sequence, in particular mRNA, that encodes for one or several antigens or epitopes.

In one embodiment, the monocytes are contacted with GM-CSF and IL-4 for about 1 to 4, preferably 1 to 3, more preferably 2 to 3 days (with 1 day counting for 24 hours), during which time the DC precursors differentiate into immature dendritic cells. In a further embodiment, the maturation time in the presence of IFN-g and MPLA takes 1 to 3, preferably 1 to 2, more preferably about 2 days (24 hours). The culture conditions are suitable for maturation of the immature DCs to form a mature DC population.

In a further embodiment, the invention provides the mature (and transfected) dendritic cells or population of mature (and transfected) dendritic cells obtainable by the method provided herein. The invention also provides a composition, kit, clinical grade bag or cryovial comprising the dendritic cells obtained by the method of the invention.

The transfected dendritic cells are especially useful for preparing a composition for immunotherapy, in particular their use in immunotherapy, more in particular in treating cancer. Hence the invention also provides a method for immunotherapy, tumor therapy or a method for activating T cells, which comprises administering transfected dendritic cells obtained by the method provided herein, to a subject.

BRIEF DESCRIPTION OF THE DRAWINGS

With specific reference to the figures, it is to be noted that the particulars shown are by way of example and for purposes of illustrative discussion of the different embodiments of the present invention. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings make it apparent to those skilled in the art how the several forms of the invention may be embodied in practice.

Figure 1A:
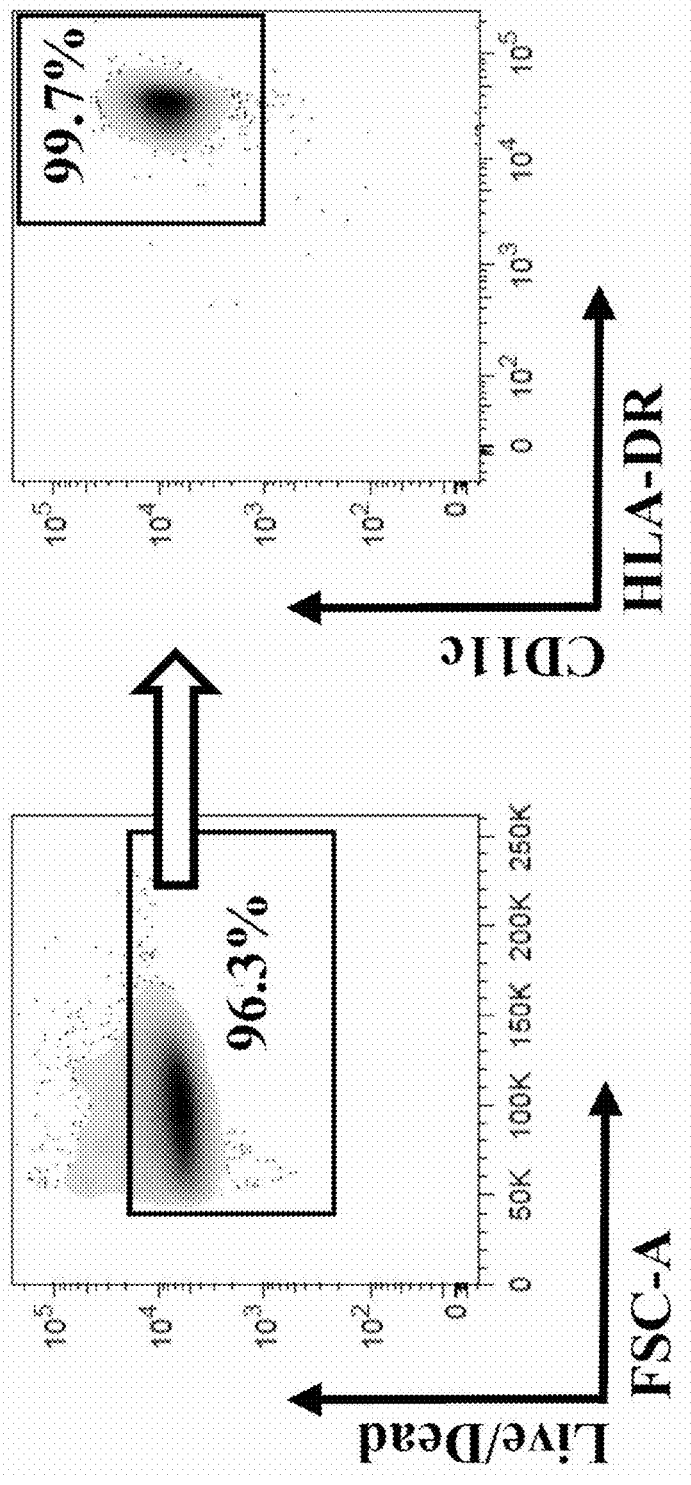
FIG. 1. Characteristics of 4-day cultured moDCs at harvest: (A) flow cytometric purity of $CD11c^{high}$ $HLA-DR^{high}$ DCs after exclusion of debris; (B) morphology under light microscopy after cytospin preparation and May-Grunwald Giemsa staining; (C) viability and monocyte-to-DC conversion rate (flow cytometry) (n=33) (box plots indicate medians and 95% C.I.); (D) cell surface expression of phenotypical and maturation markers including representative open histograms (vs grey background staining) and summarizing box plots (median and 95% C.I.; n=33) showing relative MFIs (ratio of geometric mean of the positive fluorescence signal over background fluorescence), both gated within live $CD11c^{high}$ $HLA-DR^{high}$ DCs).

no electroporation (Non-EP);
exponential pulse (EXP-EP): 300V; 150 μF; 200 μl; ∞Ω; +/−5×10E6 DCs/cuvette;
square wave pulse (SQW-EP): 500V; 0.5 ms; 200 μl; 1 pulse; +/−5×10E6 DCs/cuvette. eGFP mRNA was used at 0.5 μg/10E6 cells.

FIG. 12. (A) Flow cytometry analysis of viability and eGFP expression; (B) Stability of the DCs after thawing of cryopreserved aliquots, as assessed on viability and effective recovery of live DCs vs pre-freezing. Monocyte-derived DCs were generated from 2 separate donor leukaphereses. At harvest, DCs were electroporated with 0.5 μg eGFP mRNA/10E6 cells using a square wave pulse with the following settings: 500V; 1.0 ms; 200 μl; 1 pulse; 50×10E6 DCs/cuvette.

FIG. 13. Monocyte-derived dendritic cells were generated either according to the protocol described in the present invention ("MIDRIX DCs"), or the alt-2 protocol described in Massa et al., 2013 ("Massa DCs"). DCs were harvested at respective timepoints and electroporated with eGFP-encoding mRNA. Data from 6 different donors. (A) Viability and absolute cell yield at harvest of live CD11c+ HLA-DR+ dendritic cells obtained with both protocols. (B) Expression of the monocyte marker CD14 vs the DC differentiation marker CD83. (C) Expression of the DC maturation markers CD40, CD70, CD86 and CCR7. (D) Expression of the T-cell co-inhibitory receptor PD-L1. (E) Electroporation efficiency, expressed as levels of translated protein (relative mean fluorescence intensity of eGFP signal) as well as fraction of cells with successful translation of electroporated eGFP-mRNA (percentage eGFP+ DCs), as measured 4 hours after electroporation.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. As used in the specification and appended claims, the singular forms "a", "an", and "the" include plural referents unless the context clearly dictates otherwise. By way of example, "a compound" means one compound or more than one compound. Throughout the description and claims of this specification the word "comprise" and other forms of the word, such as "comprising" and "comprises," means including but not limited to, and is not intended to exclude, for example, other additives, components, integers, or steps. The terms described above and others used in the specification are well understood to those in the art. All references, and teachings specifically referred to, cited in the present specification are hereby incorporated by reference in their entirety.

The present invention relates to the manufacturing of a dendritic cell vaccine, in particular an autologous, monocyte-dendritic cell vaccine. Of particular interest is that the method of the invention can be performed using a clinical-grade, fully closed system. A gas-permeable culture bag or container offers the advantages of a closed fluid path culture system whereby the cell suspension may be added to the culture bag via a sterile-connect port. Ideally, the entire cell collection, and preselection if desired, is conducted in a closed fluid path system which then is aseptically connected to the gas-permeable bag for the transfer of cells into the bag. The culture media can then be continuously perfused through the bag, or periodically refreshed, via sterile connect ports and sterile tubing systems. The cell culture within the gas-permeable bag can be maintained in the gas-regulated atmosphere of the incubator without exposure to environmental hazards such as microorganisms which could otherwise be introduced into the culture when the cells are originally introduced to the bag or container, when the medium is refreshed or when new medium is added. Throughout the culture period, samples of the cultured cells can be aseptically drawn off from the bags through sterile-connect ports for analysis. Likewise, when the DC culture is ready for harvest, the cells can be aseptically drawn off for closed-system washing and/or further processing. The closed-system additionally opens the possibility to execute the cell culture in a clean-room environment with lower stringency in terms of airborne particle counts (e.g. Class C cleanroom environment). This has advantages in terms of working conditions for operators, decreases costs, and also offers the possibility to easily transpose the cell differentiation process to commercially available automated culture systems (e.g. CliniMACS Prodigy® System, Miltenyi Biotec GmBH, Bergisch Gladbach, Germany).

Hence, as used herein, the term "closed system" refers to an assembly of components, each of which is closed to the ambient environment, and each of which is provided with means for effecting sterile connections among the components. In one embodiment, the closed system comprises the leukapheresis product, along with the differentiation and maturation components as provided herein. Examples of GMP-certified gas-permeable culture bag systems are MACS® GMP Cell Culture Bags (Miltenyi Biotec GmBH, Bergisch Gladbach, Germany). As used herein, "GMP-certified" means Good Manufacturing Practice and describes the minimum standard that a medicines manufacturer must meet in their production processes. The European Medicines Agency (EMA) e.g. coordinates inspections to verify compliance with these standards and plays a key role in harmonizing GMP activities at European Union (EU) level.

In one embodiment, the method of the invention comprises the step of isolating and/or providing a population of dendritic cell precursors. Typically, a "dendritic cell precursor" as used herein is a (human) peripheral blood mononuclear cell, a monocyte or another myeloid progenitor cell. As used herein, "monocyte" refers to a CD14+ mononuclear leukocyte having the capacity to differentiate into a dendritic cell. The monocyte may be from any mammal, but preferably is a human monocyte. The monocytes can be provided and incubated in compositions such as, but not limited to, blood, blood fractions (e.g., white blood cells (WBCs), buffy coats, peripheral blood mononuclear cells (PBMCs), mononuclear cell leukapheresis products, and as well as in compositions further enriched for monocytes. In a preferred embodiment, the monocytes are provided together with other peripheral blood mononuclear cells (PBMCs), for example, as a mononuclear cell apheresis product. Methods for isolating cell populations enriched for dendritic cell precursors such as monocytes and conventional dendritic cells from various sources, including blood and bone marrow, are known in the art. For example, monocytes and conventional dendritic cells can be isolated by collecting heparinized blood, by apheresis or leukapheresis, by preparation of buffy coats, rosetting, centrifugation, density gradient centrifugation, differential lysis of cells, filtration, elutriation, fluorescence-activated cell sorting or immunomagnetic isolation. In a preferred embodiment, the monocytes are isolated from a mononuclear cell leukapheresis. Methods of leukapheresis are known in the art. Leukapheresis is a procedure by which the white blood cells are removed from a subject's blood, the remainder of which is then transfused back into the subject. The leukapheresis product is typically a blood fraction enriched for PBMCs, with low levels of contaminating red blood cells, granulocytes and platelets. Methods and equipment for performing leukapheresis are well known in the art. Monocytic dendritic cell precursors and/or differentiated conventional dendritic cells can be isolated from a healthy subject or from a subject in need of immunostimulation, such as, for example, a cancer patient or other subject for whom cellular immunostimulation can be beneficial or desired (i.e., a subject having a bacterial or viral infection, and the like). Dendritic cell precursors and/or immature dendritic cells also can be obtained from an HLA-matched healthy individual for administration to an HLA-matched subject in need of immunostimulation.

In one embodiment, the monocytes are enriched prior to the differentiation step. Manipulations may be performed on the monocytes or PBMCs, etc., and include e.g. centrifugation, elutriation, tangential flow filtration, Ficoll density gradient, dilute Ficoll density gradient centrifugation, dilute Percoll density gradient centrifugation, antibody panning, magnetic cell sorting, positive or negative immunomagnetic selection, and the like. In addition, once isolated from a subject, monocytes (e.g., purified monocytes, enriched monocytes, PBMCs comprising monocytes, etc.) can optionally be incubated, e.g. at a temperature of 1° C.-34° C. for a certain period, e.g. approximately 1 to 96 hours, from the time they are isolated from a subject.

In a particular embodiment, the monocytic progenitor is obtained from a leukapheresis by immunomagnetic isolation. Even more particular, the population of viable monocytic DC precursors is highly purified e.g. more than 90%, 95% or even 99% pure as determined by flow-cytometry using the monocytic marker CD14 and a viability stain.

Hence, the first step of a method disclosed herein comprises providing isolated (autologous) monocytic DC precursors, in particular using a closed system as provided herein. Typically the DC precursor cell density in the culture bags or containers at initiation of cell culture ranges from $0.5 \times 10E6$ to $2 \times 10E6$ cells/ml, preferably about $1 \times 10E6$ cells/ml, as determined by methods known in the art.

Following isolation, purification and/or enrichment, the DC precursors are induced to differentiate into dendritic cells. Hence in a further embodiment, the method of the invention comprises a culturing and/or differentiation step in order to obtain immature DCs, such as the culturing of the precursor cells in the presence of at least granulocyte-macrophage colony-stimulating factor (GM-CSF) and interleukin-4 (IL-4) (referred to as the differentiation medium), and this for about 48 to 96 hours, more particular for 48 to 84 hours, even more particular for up to 80, 75, 74, 73, 72, 71, 70, or less hours, more specifically for at least 48 hours and up to 72 hours. A margin of +/−4 hours or +/−2 hours is acceptable and can be necessary in view of practical constraints. In a specific embodiment, the isolated DC precursors are transferred via the closed system to gas-permeable culture bags containing the (serum-free) differentiation medium.

GM-CSF and IL-4 can be used at concentrations from about 100 U/ml to 5000 U/ml of each cytokine, preferably from 500 U/ml to 2500 U/ml, more preferably from 500 U/ml to 1500 U/ml or about 500 to 1000 U/ml. In particular, GM-CSF can be used at a concentration between 500 U/ml and 2500 U/ml, preferably between 1000 and 1500 U/ml, and more preferably at about 1000 U/ml. More specifically, IL-4 can be used at a concentration from 500 U/ml to 2500 U/ml, preferably from 500 to 1500 U/ml, more preferably from 500 to 1000 U/ml, and even more preferably at about 500 U/ml.

Following differentiation of monocytes into immature dendritic cells, the immature dendritic cells can be matured into mature dendritic cells. Hence, in one embodiment, the method of the invention comprises a maturation step, such as adding to the (differentiated) immature DCs interferon gamma (IFN-g) and monophosphoryl lipid A (MPLA) (referred to as maturation stimuli or cocktail), and this for at least up to 30 hours, preferably at least 24 hours. In particular, the maturation stimuli IFN-g and MPLA are added to the medium for the last 24 hours+/−4 hours, in particular +/−2 hours, of cell culture before harvest and/or transfection.

IFN-g is used at concentrations from 500 U/ml to 2000 U/ml, preferably from 500 U/ml to 1500 U/ml, even more preferably from 500 U/ml to 1000 U/ml, and in a particular embodiment about 1000 U/ml. MPLA is used at concentrations between 1 to 20 μg/ml, more particular between 1 to 10 μg/ml, even more particular between 1 to 5 μg/ml. In a particular embodiment, MPLA is used in a concentration of about 2.5 μg/ml. In a further embodiment, IFN-g is a pharmaceutical-grade or GMP-certified recombinant human IFN-g. As used herein, a "pharmaceutical-grade" compound refers to any active or inactive drug, biologic or reagent, for which a chemical purity standard has been established by a recognized national or regional pharmacopeia.

Hence, according to the invention, precursor and/or immature dendritic cells are cultivated with (at least) the above combination of factors, i.e. the differentiation and/or maturation factors. This can be performed by adding the factors to the culture medium. Alternatively, the culture medium in which the precursor cells and/or immature dendritic cells have been grown is replaced by a medium already containing the factors. In a further embodiment, the substances mentioned above are added or may be part of a composition added to the culture medium of said cells. Said culture medium may be of any suitable kind, i.e. may be supplemented with or without any other supplements, like e.g. proteins, amino acids, or antibiotics. In a particular embodiment, the medium is produced and used under GMP conditions. Even more particular, the culture medium is serum-free such as e.g. serum-free GMP CellGro® (CG) medium (CellGenix GmBH, Freiburg, Germany). In the embodiment of a fully closed system, precursor cells can be transferred to culture bags containing DC differentiation medium as provided herein. In a second step, and after approximately 48 hours (plus or minus 4 hours), the maturation stimuli IFN-g and MPLA are added to the medium and cells in the culture bags.

It is moreover the aim of the present invention to provide an "accelerated" in vitro cell differentiation method for the production of clinical-grade dendritic cells (DCs) with strong Th1 polarizing capacity, combined with efficient presentation of nucleic acid-encoded antigen. Typically, the duration of the DC culture protocol of the present invention is limited to about 4 days instead of the 8 day "standard" protocol.

When assessed over a range of different donors, both DC viability and monocyte-to-DC conversion rates are significantly higher with the method of the present invention compared to the standard protocol (e.g. with respect to conversion rate: method of the invention: about 45%, standard method: about 25%).

Phenotypically, the cells obtained by the method provided herein display cardinal characteristics of dendritic cells, including:
  typical dendritic cell morphology as assessed by light microscopy,
  uniform expression of the DC differentiation markers CD11c, MHC class II (HLA-DR) and CD83,
  uniform downregulation of the monocytic marker CD14.

In terms of maturation state of the DCs, this is assessed by measuring expression of specific cell surface markers, among which T-cell costimulatory molecules, preferably by flow-cytometrical analysis. In that case, expression levels are given as relative mean fluorescence intensities (MFIs) (ratio of geometric mean of the positive fluorescence signal over background fluorescence) as determined by the methods generally known. T-cell costimulatory molecules are typically assessed as maturation markers, for which the expression on the surface of DCs should be as high as possible. Conversely, it is strived to maintain expression of T-cell co-inhibitory molecules as low as possible on the final DC product.

The DCs obtained according to the method of the invention demonstrate:
  1 uniform upregulation of T-cell costimulatory molecules (CD40, CD70, CD86), and
  uniform expression of the lymphoid tissue-homing chemokine receptor CCR7.

The median levels of CD40, CD70 and CCR7 are higher with statistical significance (two-tailed p-value $<0.05$) compared to those displayed by DCs generated using the "classical" protocol. In one embodiment of the present invention, cell surface marker expression levels on DCs generated herein are compared with the same on DCs generated using the "classical" method using PGE2 and TNF-α as maturation stimuli and whereby mature dendritic cells are obtained after 8 days.

For example, for the T-cell co-inhibitory ligand PD-L1, cell surface levels as expressed by relative mean fluorescence intensity (reIMFI) (for a description of the analytical method used, see Material and Methods section under EXAMPLES) are below 400, 350, 320, 310, 300, 250, 200, in particular below 150. In addition, on the DCs produced according to the present invention, surface PD-L1 expression after electroporation, cryopreservation and cell thawing (i.e. representative for the product at the time of administration to the patient) is below 500, 470, 450, in particular below 400.

Figure 10:
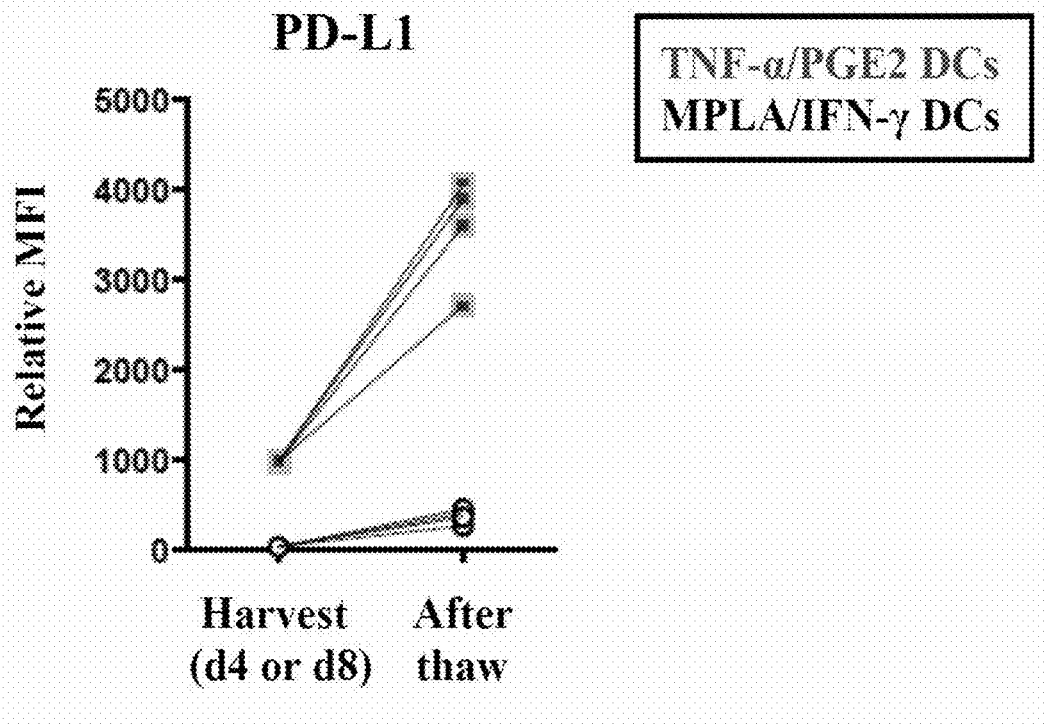
FIG. 10. Expression level of the T-cell coinhibitory molecule PD-L1 before and after cryopreservation compared between 4-day MPLA/IFN-γ and "classical" moDCs protocols. Levels of surface PD-L1 expression are calculated as relative MFI (ratio of geometric mean of the positive fluorescence signal over background fluorescence, gated within live CD11c$^{high}$ HLA-DR$^{high}$ DCs). The time points 'at harvest (n=2) (day 4 or day 8 respectively)' and 'immediately after thaw (n=4)' were included in the assay. In both DC cultures, at harvest each donor was divided over two electroporation conditions (i.e. eGFP mRNA- and MART-1 mRNA-EP) for subsequent cryopreservation and thawing.

Hence, at the time of cell harvest (directly after DC maturation), the expression levels of PD-L1 by the DCs generated according to the method of the present invention is at least 3-fold, 4-fold, 5-fold, 6-fold, 7-fold, 8-fold, 9-fold and in particular at least 10-fold, lower than expression by DCs generated using the "classical" method using PGE2 and TNF-a as maturation stimuli and whereby mature dendritic cells are obtained after 8 days (see FIG. 10 of the EXAMPLES).

Hence, at the time of cell thawing, the expression levels of PD-L1 by the DCs generated according to the method of the present invention is at least 4-fold, 5-fold, 6-fold, 7-fold, 8-fold, 9-fold and in particular at least 10-fold, lower than expression by DCs generated using the "classical" method using PGE2 and TNF-a as maturation stimuli and whereby mature dendritic cells are obtained after 8 days (see FIG. 10 of the EXAMPLES).

Functionally, after cryopreservation and thawing the cells preserve the capacity to secrete type-1 polarizing cytokines (IL-12, IFN-g) and chemokines attracting Th1, CD8 and NK cells during prolonged incubation in cytokine-free medium. In particular the DCs produced according to the method of the present invention secrete statistically significant higher levels of the CXCR3 ligands CXCL9 (MIG30) and CXCL10 (IP-10), as well as the CCR5 ligands CCL3 (MIP-1a), CCL4 (MIP-1β) and CCL5 (RANTES), and lower to undetectable levels of CCL17 compared to DCs obtained with the aforementioned "classical" method. In one embodiment, the cytokine and chemokine secretion level is expressed in relative terms, i.e. when compared to the secretion level of the resp. cytokine or chemokine by DCs generated using the "classical" method using PGE2 and TNF-a as maturation stimuli and whereby mature dendritic cells are obtained after 8 days. Secretion levels can be determined by using standard protein measuring methods, e.g. ELISA or the herein provided Luminex® method.

For example, for the prototypical type-1 T-cell-polarizing and NK cell-supporting chemokine IL-12, the range of levels released in dendritic cell supernatant after thawing and further culture in the abovementioned conditions are:

for DCs produced according to the method of the invention: from 50 to 250 µg/ml; in particular 60 to 200 µg/ml; more in particular 70 to 150 µg/ml;

for DCs produced according to the "standard" 8-day protocol: 0 to 35 µg/ml but less than 50 µg/ml.

For the chemokine CXCL10 (important in recruiting type-1-polarized T-cells and NK-cells), the range of levels released in dendritic cell supernatant after thawing and further culture in the abovementioned conditions are:

for DCs produced according to the method of the invention: from 200 to 2000 µg/ml; in particular 250 to 1800 µg/ml; more in particular 280 to 1600 µg/ml;

for DCs produced according to the "standard" 8-day protocol: 0-5 pg/ml but less than 10 pg/ml.

Hence for CXCL10 the secretion levels by the DCs generated according to the method of the present invention are at least 50-fold higher than the secretion by DCs generated using the "classical" method. A similar superiority of the DCs obtained with the method of the present invention is observed with additional cytokines and chemokines that promote type-1 polarized inflammatory responses as required for anti-cancer immunity, among which IFN-g, CCL3, CCL4, CCL5 and CXCL9.

By contrast, for the chemokine CCL17 (involved in the recruitment of regulatory T-cells and type 2-polarized T-cells, both detrimental to anti-cancer immune responses), release by the DCs generated according to the method of the present invention is at least 3-fold lower than secretion by DCs generated using the "classical" method.

Accordingly, the DCs obtained with the method of the invention drive the differentiation of naïve T-helper cells towards a type-1 polarized profile characterized by high IFN-γ secretion, as required for e.g. active cancer immunotherapy. Moreover, said cells can present immunogenic epitopes derived from transfected mRNA and subsequently drive the expansion of autologous, tumor antigen-specific CD8+ T-cells that express IFN-γ and the cytotoxic molecule granzyme B, as already mentioned.

In a further embodiment, the method of the invention comprises loading or transfecting the mature DCs with an antigen encoding nucleic acid, in particular RNA, more in particular mRNA. As used herein, the "antigen" is not limiting to the invention. In one embodiment, the antigen is selected from the group consisting of a tumor-antigen, a tumor-associated antigen, a cancer-testis antigen, a muta-nome-derived antigen, a (oncogenic) viral antigen, a bacterial antigen, a yeast antigen, a parasitic antigen and a fungal antigen. The antigen can be autologous to the subject, and can be used to prepare an antigen-loaded autologous DC vaccine for administration to the subject. By autologous to the subject is meant that the antigen (or sequence thereof) is obtained or derived from the same subject. As non-limiting examples, the antigens may be from cancer cells or tumor tissue obtained from a subject. The cancer antigens could be loaded into dendritic cells as cancer cells, cancer cell or tissue lysates, extracts from cancer cells or tissues, purified or cloned components of cancer cells or tissues, total RNA or total mRNA, or selected RNA or mRNA from such cells or tissues, whether present in extracts, purified, amplified, in vitro translated and the like. Alternatively, the antigen may be obtained or derived from a pathogen or from pathogen-infected cells present in a subject. The term "nucleic acid" refers to single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. More specifically, the dendritic cells are transfected in vitro with one or more antigen encoding mRNA. Optionally and in an alternative embodiment, after the maturation period is completed, DCs may be first harvested before further handling (such as e.g. transfection), whereby the cells are collected, centrifuged and/or the cytokines are washed out.

In view of the accelerated culture protocol, the transfection of the mature DCs is possible at about 72 to 96 hours, in particular after 86 hours+/−4 hours, after the monocyte isolation or the addition of differentiation stimuli to the precursor DCs.

In the context of the present invention, transfection methods include, but are not limited to, electroporation, photo-poration, lipofection, viral vector systems, incubation of naked nucleic acids or fusion of DCs with infected cells or tumor cells. These standard methods are well known in the art and are feasible and introduce nucleic acids, such as antigen encoding plasmids, RNA of them or DNA, into the DCs. There might also be other antigenic combinations with original MHC molecules conceivable such as membrane fragments or exosomes to use as antigen sources of any kind. In a specific embodiment, the mature DCs are transfected by electroporation. Three different types of pulses can be used for electroporation such as Exponential Decay Pulse, Square Wave Pulse and Time Constant. In a particular embodiment of the invention, the electroporation consists of square wave pulse. Typically 1 or 2 pulses are induced in order to complete transfection.

In a one embodiment of the invention, the antigen is loaded by electroporation of a dendritic cell with a nucleic acid, preferably a mRNA. Preferably, the dendritic cells are transfected with approximately 0.25 to 4 µg RNA per 10E6 dendritic cells, most preferably with about 1 to 3 µg RNA per 10E6 dendritic cells. In one embodiment, 1 to 2 µg antigen RNA per million DC is used per transfection.

It was demonstrated herein that the cells obtained by the method of the invention uniformly and stably express protein derived from transfected mRNA (see EXAMPLES). Moreover, said cells can present immunogenic epitopes derived from transfected mRNA and subsequently drive the expansion of autologous, tumor antigen-specific CD8+ T-cells with a cytotoxic profile, as required for e.g. active cancer immunotherapy.

In the context of the present invention, it has been found that stimulation of immature dendritic cells as provided herein under shortened incubation times, e.g. within approximately 3 days, results in the generation of mature dendritic cells with improved viability, functionality and/or immunostimulatory activity as compared to mDCs prepared by a "classical" protocol of 8 days. As used herein, the term "immunostimulatory activity" refers to the capability of a mature dendritic cell or of a mature dendritic cell population to produce and/or to secrete sufficient amounts of specific cytokines and chemokines, in particular IL-12 and CXCL10, which mediate the correct differentiation and mobilization of type-1-polarized effector T-cells and NK cells, as e.g. required for immunity against cancer and specific pathogens.

In one embodiment of the present invention the loaded/transfected dendritic cells can be frozen in a composition comprising a cryoprotectant. Numerous cryoprotectants and methods for freezing DCs are known to those skilled in the art. As an example, the dendritic cells are cooled using a controlled rate freezer and transferred for cryopreservation and storage in the vapour phase of a liquid nitrogen container. In particular, the dendritic cells are resuspended in a suitable cryopreservation medium in volume aliquots of 100 µL at a concentration of 20-70×10E6 live cells/mL, more specifically about 40-60×10E6 live cells/mL, even more specifically about 50×10E6 live cells/mL. In a further step, the thawed dendritic cell vaccine is ready for administration to a subject at any time, generally up to about 4 hours, after thawing.

In one embodiment, the invention provides a cryovial comprising cryopreserved, mature, transfected, in particular electroporated, DCs as provided herein, in particular in an amount of about 5×10E6 cells per 100 µL as measured prior to cryopreservation.

The invention further provides a method for the administration of an antigen loaded dendritic cell vaccine, comprising thawing cryopreserved live dendritic cells prepared according to the method provided herein and administering them to a subject.

The present invention also provides the use of an antigen-loaded dendritic cell obtained by the method disclosed herein as a medicament, in particular for the preparation of a medicament or pharmaceutical composition. The invention provides DCs or compositions as described herein for use in immunotherapy, in particular for the treatment or prevention of cancer or a pathogen infection.

In a further aspect, the present invention encompasses a pharmaceutical composition comprising the mature dendritic cells according to the present invention and a pharmaceutical acceptable carrier and/or excipient. Furthermore, the invention also relates to the mature dendritic cell or to the population of mature dendritic cells of the invention for use in a method of treating a disease selected from the group consisting of malignant disorders (cancer), specific non-malignant disorders (e.g. LAM lung disease (Lymphangioleiomyomatosis), and infectious diseases (e.g. provoked by viruses, bacteria, intracellular bacteria or fungi). Furthermore, the present invention relates to a method for treating a patient with a tumoral disease (such as cancer) or an infectious disease, wherein an effective amount of the mature dendritic cell of the invention is administered to said patient.

The antigen-loaded dendritic cells of the invention are useful as vaccines in the treatment or prevention of disease or for the activation of T cells. For example, antigen loaded dendritic cells can be used to elicit an immune response against an antigen. They may be used as vaccines to prevent future infection or disease ("prophylactic vaccination"), or to activate the immune system to treat ongoing disease ("therapeutic vaccination"), such as, but not limited to pathogen infection or cancer. The antigen loaded dendritic cells as prepared herein may be formulated for use as vaccines or pharmaceutical compositions with suitable carriers such as physiological buffers or other injectable liquids. The vaccines or pharmaceutical compositions are administered in therapeutically effective amounts sufficient to elicit an immune response.

The terms "treatment" and "treating" as used herein generally mean to obtain a desired pharmacologic and/or physiologic effect, and covers any treatment of a disease in a mammal, particularly a human, including:

(1) preventing the disease or symptom from occurring in a subject which may be predisposed to the disease or symptom, but has not yet been diagnosed as having it;

(2) inhibiting the disease symptom, i.e., arresting its development; or (3) relieving the disease symptom, i.e., causing regression of the disease or symptom.

The effect may be prophylactic in terms of completely or partially preventing a disease or symptom thereof and/or may be therapeutic in terms of a partial or complete stabilization or cure for a disease and/or adverse effect attributable to the disease. In addition, the vaccine can be used as "adjuvant therapy" given in addition to a primary or initial therapy to maximize its effectiveness in a curative setting, or as a "maintenance" or "consolidative" therapy subsequent to and initial therapy to maximize disease control and delay disease recurrence.

In the context of the present invention, the term "cancer" refers to any kind of disease provoked by a malignant tumor. The term "infectious disease" as used herein refers to any kind of clinically evident disease resulting from the presence of pathogenic microbial agents, including pathogenic viruses, pathogenic bacteria, fungi, protozoa, or multicellular parasites.

Methods for formulating dendritic cell vaccines are known to those of skill in the art. Suitable formulations for administration can include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, immunostimulants, cytokines and adjuvants.

The dendritic cell composition/vaccine can be administered by a variety of methods, such as, but not limited to, injection (e.g., subcutaneous, intradermal, intravenous, intralymphatic, intraarticular, intramuscular, intraperitoneal), by continuous infusion, sustained release from implants, etc. DC vaccines can be been administered at specific intervals. In one embodiment, the DCs are administered at two to four week intervals, in particular two week intervals. The dendritic cell vaccine can be administered with physiologically acceptable carriers, buffers, diluents, adjuvants, immunomodulators, etc. Preferably, the dendritic cell vaccine is autologous to the patient it is administered to, or is maximally HLA-matched.

The dose of cells administered to a subject is in an effective amount, effective to achieve the desired beneficial therapeutic response in the subject over time, or to inhibit growth of cancer cells, or to inhibit infection, while maintaining a good tolerability profile (minimal toxicity). An amount adequate to accomplish this is defined as a "therapeutically effective dose." The dose will be determined by the biological and/or clinical activity of dendritic cell produced and optionally the condition of the patient. The size of the dose also will be determined by the existence, nature, and extent of any adverse side-effects that accompany the administration of a particular cell in a particular patient. In determining the effective amount of the cell to be administered in the treatment or prophylaxis of diseases such as cancer (e.g., metastatic melanoma, prostate cancer, etc.), the physician (or investigator) needs to evaluate immune responses against the targets included in the vaccine (i.e. immunomonitoring), along with the clinical evolution of the tumor using measurable parameters (radiological tumor burden by regular or immune-related RECIST criteria, tumor markers, circulating tumor cells, plasma circulating tumor DNA or other surrogate markers of disease load or disease activity).

It is well known to those skilled in the art that there is no evidence for a preferred dose of DCs to be administered to achieve a specific level of biological and/or clinical effect. Likewise no clear dose-limiting toxicity (DLT) has been observed and accordingly no maximal tolerated dose (MTD) has been observed. The doses most commonly administered are dictated by the yield of DCs obtained from one round of leukapheresis and the desired number of subsequent vaccinations. In one embodiment, doses fall within 5-100×10E6 DCs per vaccination round, repeated 2 to 8 times, in particular 2 to 6 times, more in particular 2 to 4 times. Likewise, there is no relationship between the number of cells injected and toxicity. Toxicity with DC vaccination is usually low, and rather linked to the route of administration (more acute side effects with intravenous route as compared to intradermal route). The injections may be e.g. 2, 3, 4, 5 or 6 times repeated in a 1, 2 or 3 weeks interval and should be given either intravenously or near lymph nodes by intradermal or subcutaneous injections or injected directly into the lymph nodes. Booster injections may be performed after a pause, e.g. of 1 to several months.

Biological response modifiers are optionally added for treatment by the DCs or activated T cells of the invention. For example, the cells are optionally administered with an adjuvant, or cytokine such as GM-CSF, IL-12, IFN-α or IL-2.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The invention will be further described by the following figures, tables and examples, which are not intended to limit the scope of protection as defined in the claims. The methods and experiments described in the examples relate mostly to the preclinical development using anonymous donor buffy coats as starting material.

EXAMPLES

Materials and Methods

Monocyte-Derived Dendritic Cell Cultures

Buffy coats were obtained from the local blood transfusion center and peripheral blood mononuclear cells (PBMCs) were isolated by Ficoll-paque density gradient centrifugation (GE Healthcare Life Science, Chicago, Illinois, USA). Monocytes were immunomagnetically purified using human anti-CD14 immunomagnetic microBeads (Miltenyi Biotec, Bergisch Gladbach, Germany), according to the manufacturer's protocol. A purity of >90% was consistently obtained, as assessed by flow cytometry (data not shown).

The monocyte-depleted fractions (peripheral blood lymphocytes (PBLs)) were frozen in RPMI-GlutaMAX medium (Invitrogen by Life Technologies, California, USA) with 10% fetal bovine serum (FBS) (Sigma-Aldrich, Missouri, USA), 100 U/ml penicillin/streptomycin (P/S) (Gibco by Life Technologies, California, USA) and 10% dimethyl sulfoxide (DMSO) (Sigma-Aldrich, Missouri, USA).

For our accelerated (i.e. 4-day) DC culture protocol, monocytes were cultured in 30 ml GMP cell differentiation bags (Miltenyi Biotec, Bergisch Gladbach, Germany) at a density of 2×10E6 cells/ml in serum-free GMP CellGro (CG) medium (CellGenix GmBH, Freiburg, Germany) containing 1000 U/ml pharmaceutical-grade granulocyte macrophage colony-stimulating factor (GM-CSF) (Leukine (Berlex), Bayer HealthCare Pharmaceuticals, New Jersey, USA), 1000 U/ml GMP-certified recombinant human interleukine-4 (huIL-4) (Miltenyi Biotec, Bergisch Gladbach, Germany) and 100 U/ml P/S (Gibco by Life Technologies, California, USA). On day 3, 2.5 µg/ml synthetic MPLA (Invivogen, California, USA) and 1000 U/ml pharmaceutical-grade IFN-γ (Immukine, Boehringer Ingelheim BV, Ingelheim, Germany) were added to the culture medium for another 24 h. Mature DCs (mDCs) were harvested on day 4.

For the "classical" (8-day) protocol, monocytes were cultured in polystyrene culture flasks (Nunc by Thermo Fisher Scientific, Massachusetts, USA) at a density of 1×10E6 in the same complete medium, except for the lower concentration of recombinant huIL-4 (250 U/ml; Miltenyi Biotec, Bergisch Gladbach, Germany) and the addition of 1% pooled human AB serum (huAB serum) (Sigma-Aldrich, Missouri, USA). At day 3 or 4, fresh GM-CSF- and IL-4-containing culture medium was added. On day 6, 20 ng/ml recombinant human TNF-α (Miltenyi Biotec, Bergisch Gladbach, Germany) and 2.5 µg/ml pharmaceutical-grade PGE2 (Prostin E2, Pfizer, New York, USA) were added to the culture medium for an additional 48 h. Mature DCs were harvested on day 8.

DC Phenotypic Analysis

For surface staining, cells were first washed and then resuspended in phosphate buffered saline (PBS) (Invitrogen by Life Technologies, California, USA) prior to 20 min incubation at 4° C. with a combination of FcR-blocking reagent (Miltenyi Biotec, Bergisch Gladbach, Germany) and fixable viability dye eFluor 506 (eBioscience by Thermo Fisher Scientific, Massachusetts, USA) to stain dead cells.

Next, cells were washed with FACS buffer, consisting of PBS (Invitrogen by Life Technologies, California, USA) supplemented with 0.5 mM ethylene diamine tetraacetic acid (EDTA); 0.25% bovine serum albumin (BSA); and 0.05% NaN3 (all from Sigma-Aldrich, Missouri, USA), before adding the surface antibodies (Abs) for 30 minutes at 4° C. The following fluorochrome-conjugated monoclonal Abs were used: anti-CD40 FITC; anti-HLA-ABC FITC; anti-CCR7 APC; anti-CD11c Alexa Fluor 700; anti-HLA-DR APC-Cy7 (eBioscience by Thermo Fisher Scientific, Massachusetts, USA); anti-HLA-A2 FITC; anti-DNGR-1 PE; anti-CD86 PE Texas Red; anti-CD83 PE-Cy7; anti-PD-L1 Pacific Blue (BD Biosciences, New Jersey, USA); anti-CD70 PE; and anti-CD14 Pacific Blue (Miltenyi Biotec, Bergisch Gladbach, Germany).

Samples were acquired on an LSR Fortessa analytical flow cytometer (BD Biosciences, New Jersey, USA) and analyzed using FlowJo software (version 9.9.4; BD Biosciences, New Jersey, USA). Phenotypical and maturation marker expression levels are shown as relative mean fluorescence intensities (MFIs) (ratio of geometric mean of the positive fluorescence signal over background fluorescence, gated within live CD11c$^{high}$ HLA-DR$^{high}$ DCs).

Luminex Assay

Cryopreserved aliquots of 4-day and 8-day monocyte-derived DCs (moDCs) were thawed and cultured for 24 h in serum- and cytokine-free CG medium (CellGenix GmBH, Freiburg, Germany) supplemented with 100 U/ml P/S (Gibco by Life Technologies, California, USA). DC culture supernatants were collected and analyzed using the Luminex assay (R&D Systems, Minneapolis, USA), customized to include the following human cytokines and chemokines: IL-12p70; IFN-γ; IL-10; CCL3; CCL4; CCL5; CXCL9;

CXCL10; CCL17; CCL20; and CXCL12. The Luminex assay was analyzed on a Bio-Plex (Bio-Rad, California, USA) reader.

mRNA Electroporation of DC

After harvest, at day 4 or day 8 respectively, DCs were electroporated and subsequently cryopreserved in Plasma-Lyte A (Baxter, Illinois, USA) enriched with 3.5% human serum albumin (Sanquin, Amsterdam, The Netherlands); 6.25% hydroxyethyl starch (HES) (Grifols, Barcelona, Spain); and 6.25% DMSO (Sigma-Aldrich, Missouri, USA). eGFP mRNA originated from a pST1-eGFP2 plasmid, kindly provided by the Laboratory of Molecular and Cellular Therapy (LMCT) of the Free University of Brussels, Prof. K. Thielemans. The plasmid was first linearized using the SapI restriction enzyme (New England Biolab, Massachusetts, USA) and subsequently in vitro transcribed into mRNA using the mMESSAGE mMACHINE T17 Ultra kit (Ambion by Thermo Fisher Scientific, Massachusetts, USA). The MART-1 mRNA was also donated by the LMCT. The open reading frame of MART-1 was fused to the HLA class II-targeting sequence of the lysosomal protein DC-LAMP1, as described earlier by Bonehill et al (2004). 4 to 16×10E6 DCs were resuspended in 170 µl serum-free CG medium (CellGenix GmBH, Freiburg, Germany), supplemented with 30 µl mRNA dissolved in nuclease-free water (Applied Biosystems by Life Technologies, California, USA) at a dosage of 1 µg mRNA/10E6 DCs and transferred to a 4 mm gap cuvette (Bio-Rad, California, USA). Electroporation using the exponential wave pulse was performed using the Gene Pulser Xcell Electroporation System (Bio-Rad, California, USA) with the following parameters: capacity 150 µF; voltage 300V; resistance Q. Immediately after EP, DCs were left to recover for 4 hours at 37° C. and 5% $CO_2$ on ultra-low attachment plates (Corning, New York, USA) in CG medium (CellGenix GmBH, Freiburg, Germany) supplemented with 1000 U/ml GM-CSF (Leukine (Berlex), Bayer HealthCare Pharmaceuticals, New Jersey, USA), recombinant huIl-4 (1000 U/ml or 250 U/ml depending on the DC type; Miltenyi Biotec, Bergisch Gladbach, Germany) and 100 U/ml P/S (Gibco by Technologies, California, USA). MOCK-EP DCs were electroporated with the same pulse settings in CG medium (CellGenix GmBH, Freiburg, Germany) without mRNA. Electroporation using the square wave pulse electroporation (SQW-EP) was performed using the same electroporation system, with the following parameters: voltage 500V; 0.5 ms; 200 µl; 1 pulse; 5×10E6 or 50×10E6 DCs/cuvette.

Allogeneic T Helper Cell Polarization Assay

Electroporated and cryopreserved DCs were thawed, allowed to recover for at least 1 hour at 37° C. and 5% $CO_2$ in warm RPMI-GlutaMAX medium (Invitrogen by Life Technologies, California, USA) supplemented with 10% huAB serum (Invitrogen by Life Technologies, California, USA) and 100 U/ml P/S (Gibco by Life Technologies, California, USA) and used as stimulators. As responders, CD45RO-negative T helper cells were enriched from allogeneic PBLs using the naive CD4+ T-cell isolation kit II on an AutoMACS cell separator (both from Miltenyi Biotec, Bergisch Gladbach, Germany). DCs and T-cells were co-cultured for 14 days at a 1:5 DC:T-cell ratio in RPMI-GlutaMAX medium (Invitrogen by Life Technologies, California, USA) supplemented with 10% huAB serum (Sigma-Aldrich, Missouri, USA) and 100 U/ml P/S (Gibco by Life Technologies, California, USA). 10 ng/ml recombinant human IL-2 (R&D Systems, Minneapolis, USA) was added at day 7 of the co-culture, and additionally at day 3 and 10 for control conditions containing no DCs.

At the end of the allogeneic co-culture, 50 ng/ml phorbol 12-myristate 13 acetate (PMA); 1 µg/ml ionomycine (iono) and 10 µg/ml brefeldin A (BFA) (all from Sigma-Aldrich, Missouri, USA) were added for 5 hours at 37° C. and 5% CO2, whereafter cells were harvested for flow cytometry staining. Antibodies detecting surface T-cell markers included anti-CD3 PerCP-Cy5.5; anti-CD8a PE-Cy7 (BioLegend, California, USA); anti-CD4 APC-Cy7 (BD Biosciences, New Jersey, USA); and anti-CD45RO PE-Cy7 (eBioscience by Thermo Fisher Scientific, Massachusetts, USA). For intracellular (IC) stainings, cells were washed with FACS buffer after surface staining and treated with Cytofix/Cytoperm (BD Biosciences, New Jersey, USA), according to the manufacturer's protocol, prior to 30 minutes incubation at 4° C. with the following Abs: anti-IL-4 FITC (BD Biosciences, New Jersey, USA); anti-IL-10 PE; anti-IL-17A APC; and anti-IFN-γ Pacific Blue (eBioscience by Thermo Fisher Scientific, Massachusetts, USA).

Expansion of Antigen-Specific Autologous CTLs

Buffy coats from HLA-A2+ donors were used to generate 4-day MPLA/IFN-γ-matured DCs, which were either frozen 4 hours after harvest (i.e. non-EP DCs) or first electroporated with either vehicle (i.e. eGFP mRNA-EP DCs) or antigen MART-1 mRNA (i.e. MART-1 mRNA-EP DCs) before cryopreservation. For more details on DC culture and manipulations, we refer to the above materials and methods sections "monocyte-derived dendritic cell culture" and "mRNA electroporation of DC".

After thawing, non-EP DCs; eGFP mRNA-EP DCs; and MART-1 mRNA-EP DCs were allowed to recover for at least 1 hour at 37° C. and 5% CO2 in RPMI-GlutaMAX medium (Invitrogen by Life Technologies, California, USA) supplemented with 10% huAB serum (Invitrogen by Life Technologies, California, USA) and 100U/ml P/S (Gibco by Life Technologies, California, USA). Afterwards, half of the non-EP DCs were pulsed with 10 UM of an optimized, immunodominant, HLA-A*201-restricted peptide from MART-1 (AAAGIGILTV; SEQ ID NO 1) (Genscript, New Jersey, USA) (Valmori D. et al. 1998), serving as positive control condition. Half of the non-EP DCs was only pulsed with vehicle and served as negative control condition (MOCK pulsed DCs). After incubation for at least 1 hour at 37° C. and 5% CO2, unbound peptides were washed away using the same culture medium as described above CD8+ T-cells were purified from the cryopreserved autologous CD14-negative fraction using a positive immunomagnetic selection kit (Miltenyi Biotec, Bergisch Gladbach, Germany). DCs and T-cells were co-cultured for 14 days at a 1:10 ratio in RPMI-GlutaMAX medium (Invitrogen by Life Technologies, California, USA) supplemented with 10% huAB serum (Invitrogen by Life Technologies, California, USA) and 100 U/ml P/S (Gibco by Life Technologies, California, USA). 20 ng/ml recombinant human IL-2 (R&D Systems, Minneapolis, USA) was added at day 3 and 10. Culture wells with autologous CD8+ T-cells without DCs were included as additional controls. At day 7 of the co-culture, autologous CD8+ T-cells were re-stimulated with the corresponding DCs (i.e. MOCK-pulsed DCs, eGFP mRNA-EP DCs, MART-1 mRNA DCs, and MART-1 peptide pulsed DCs). At the end of the co-culture, cells were incubated with PMA/iono/brefA for 5 hours as described above, and harvested for surface staining using PE-conjugated A*02:01/human MART-1 MHC tetramer (Sanquin, Amsterdam, The Netherlands) and intracellular staining using the following markers: anti-IFN-γ FITC (BioLegend, California, USA); and anti-granzyme B Pacific Blue (BD Biosciences, New Jersey, USA).

Evaluation of DC-Induced Antigen-Specific Cytolytic Activity

Effector T-cells were harvested at day 14 of autologous DC: T-cell co-cultures set-up as described above. Target cells consisted of TAP2-deficient T2 cells loaded with the same peptide from MART-1 as described above (Genscript, New Jersey, USA), or an irrelevant A2-restricted peptide from influenza matrix protein with sequence GILGFVFTL (AnaSpec, California, USA; SEQ ID NO 2) as a control, both used at 10 μg/ml. T2 cells were pulsed for 3 hours and washed thoroughly to remove unbound peptide. Co-cultures were set-up for 14 hours at an E:T ratio of 10:1, in the presence of monensin (Golgistop, BD Biosciences, New Jersey, USA) and anti-CD107a Pacific Blue Ab (Miltenyi Biotec, Bergisch Gladbach, Germany). At the end of the co-cultures, cells were stained with surface anti-CD3, anti-CD8 and anti-CD137 (eBioscience by Thermo Fisher Scientific, Massachusetts, USA).

Statistics

Statistical analysis was performed using GraphPad Prism (version 7.02, GraphPad Software, California, USA). Normal distribution was first tested using the D'Agostino-Pearson omnibus normality test. Normally-distributed data was analyzed with the unpaired or paired t-test for 2 groups or the ANOVA test in combination with Tukey's multiple comparisons testing for 3 or more groups. For non-normally distributed data, non-parametric tests were used, i.e Mann-Witney test for unpaired data sets and the Wilcoxon matched-pairs signed rank test for paired data sets for 2 groups. For more than 2 groups, the non-parametric Kruskal-Wallis test was used in combination with the Dunn's multiple comparisons testing. Levels of statistical significance were coded with asterix symbols as follows: p-value 0.01-0.05 (*), p-value 0.001-0.01 (), p-value <0.001 (*) and p-value <0.0001 (****).

Results

High Yields of Fully-Differentiated Mature Dendritic Cells can be Obtained by a Shortened Monocyte Culture Protocol Involving Maturation with a TLR4-Ligand Plus IFN-γ

The feasibility of generating DCs by combining a greatly reduced monocyte culture duration, together with maturation using an established type-1 polarizing factor combination, was assessed using an extensive series of small-scale cultures starting from buffy coats. Cell culture media, cytokines and closed-system containers were selected for direct translation to our GMP production environment.

Figure 1B:
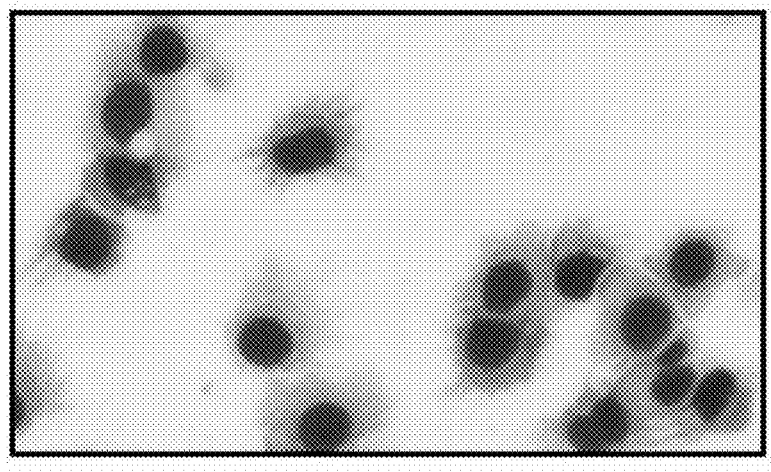
Figure 1B:
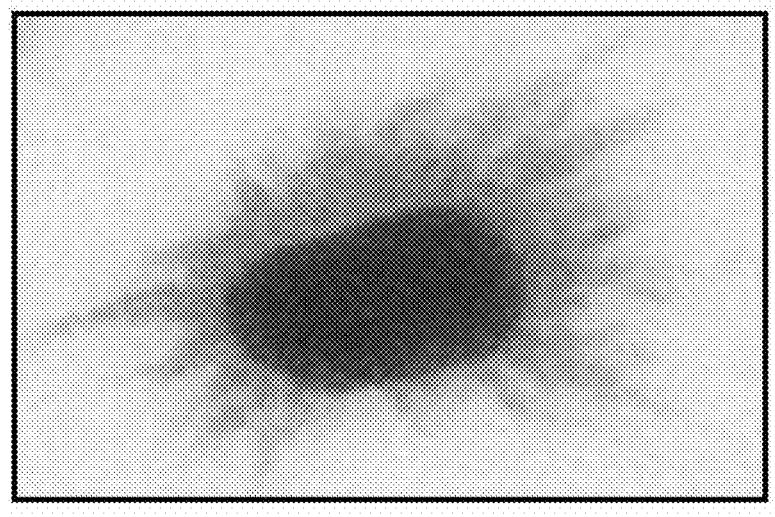
Figure 1C:
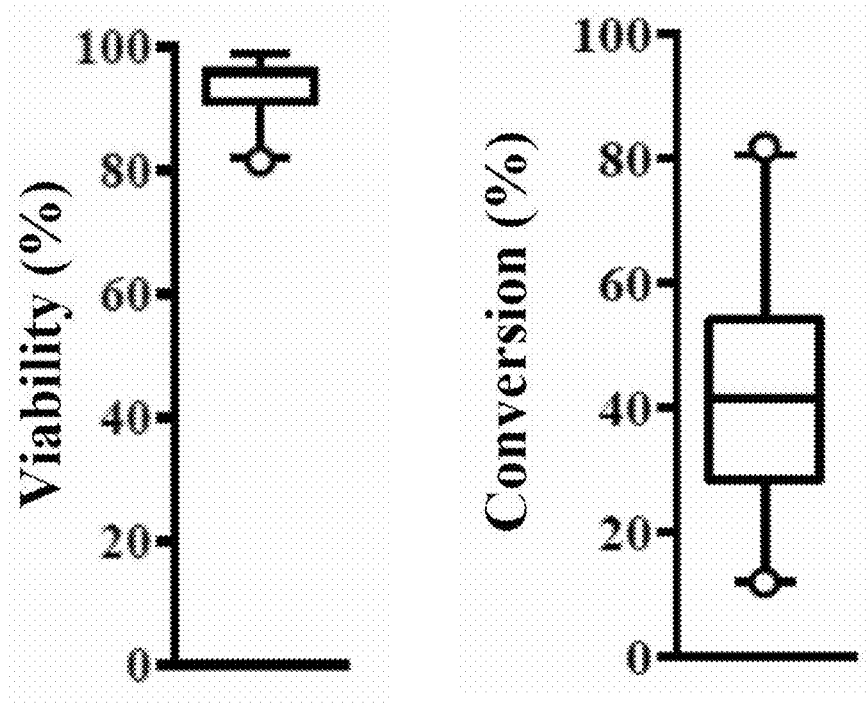

To reduce the need for operator intervention, we aimed to cut the standard 8-day DC culture duration to a total period of 4 days. This consisted of 3 days culture in GM-CSF/IL-4-supplemented GMP-compliant, serum-free medium, followed by exposure to the combination of MPLA and IFN-γ for an additional 24 hours before harvest. This protocol resulted in a CD11c$^{high}$ HLA-DR$^{high}$ mononuclear cell population with a median purity of 94.6% [95% CI: 93.7-96.9] (FIG. 1A), showing characteristic dendritic morphology by light microscopy (FIG. 1B). At harvest, the median monocyte-to-DC conversion rate was 41.5% [95% CI: 30.7-51.7] with a median viability (by flow cytometry) of 95.7% [95% CI: 92.7-96.4] (FIG. 1C).

Figure 1D:
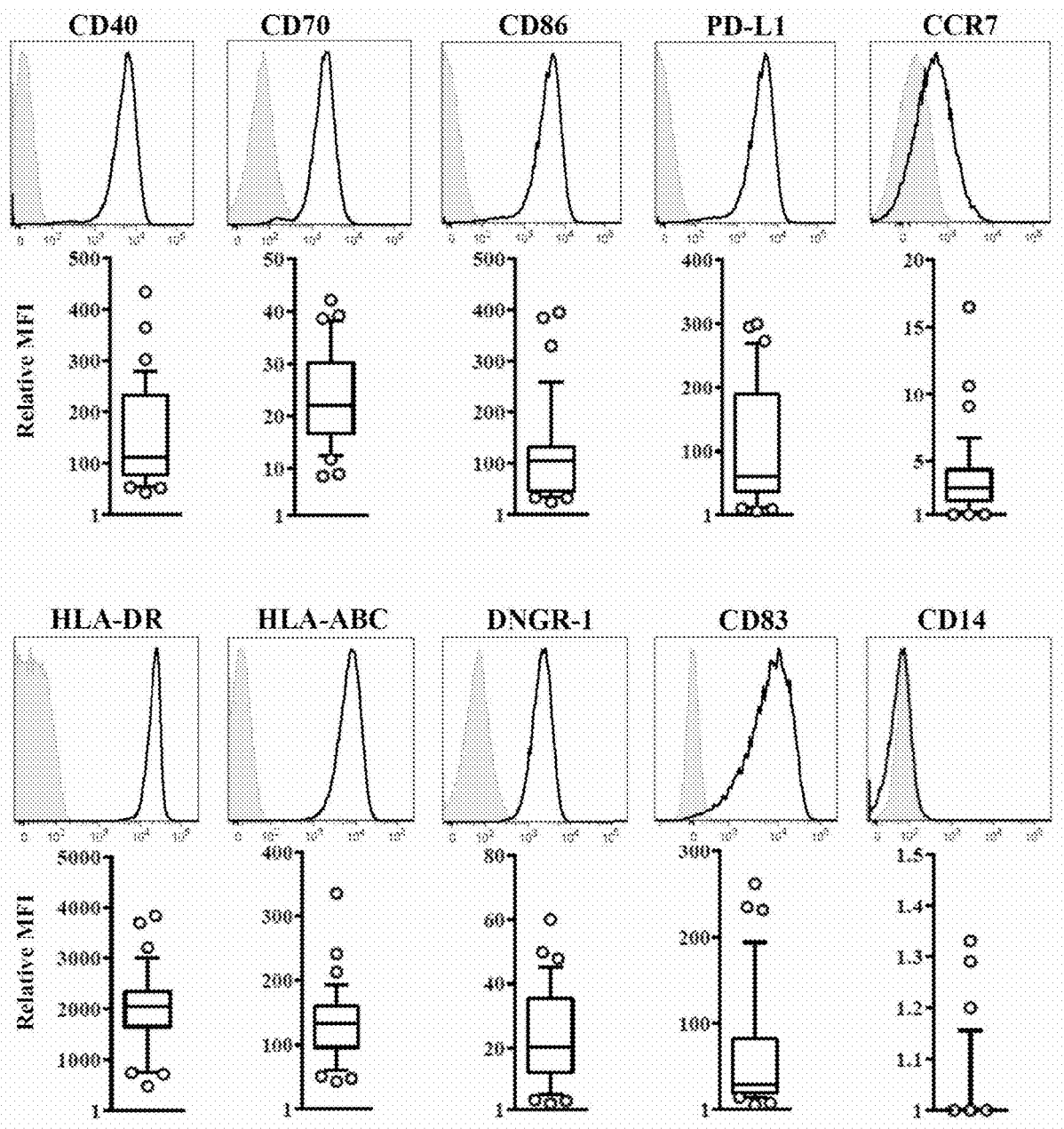

The phenotype of the cells was consistent with that of fully differentiated, mature DCs, with profound downregulation of the monocytic marker CD14, paralleled by an upregulation of CD83 as well as a high surface expression of the T-cell costimulatory markers CD40, CD70, and CD86 in combination with high levels of HLA class I and class II antigen-presenting molecules. Furthermore, the observation that the molecule DNGR-1 could be detected at high level suggests a potential to capture and cross-present exogenous cell-bound antigens. CCR7 was induced on mature DCs, indicating a capacity to migrate to secondary lymphoid organs. The T-cell checkpoint molecule PD-L1 was also upregulated, as a reflection of the global activation status of the moDCs (FIG. 1D).

Figure 9:
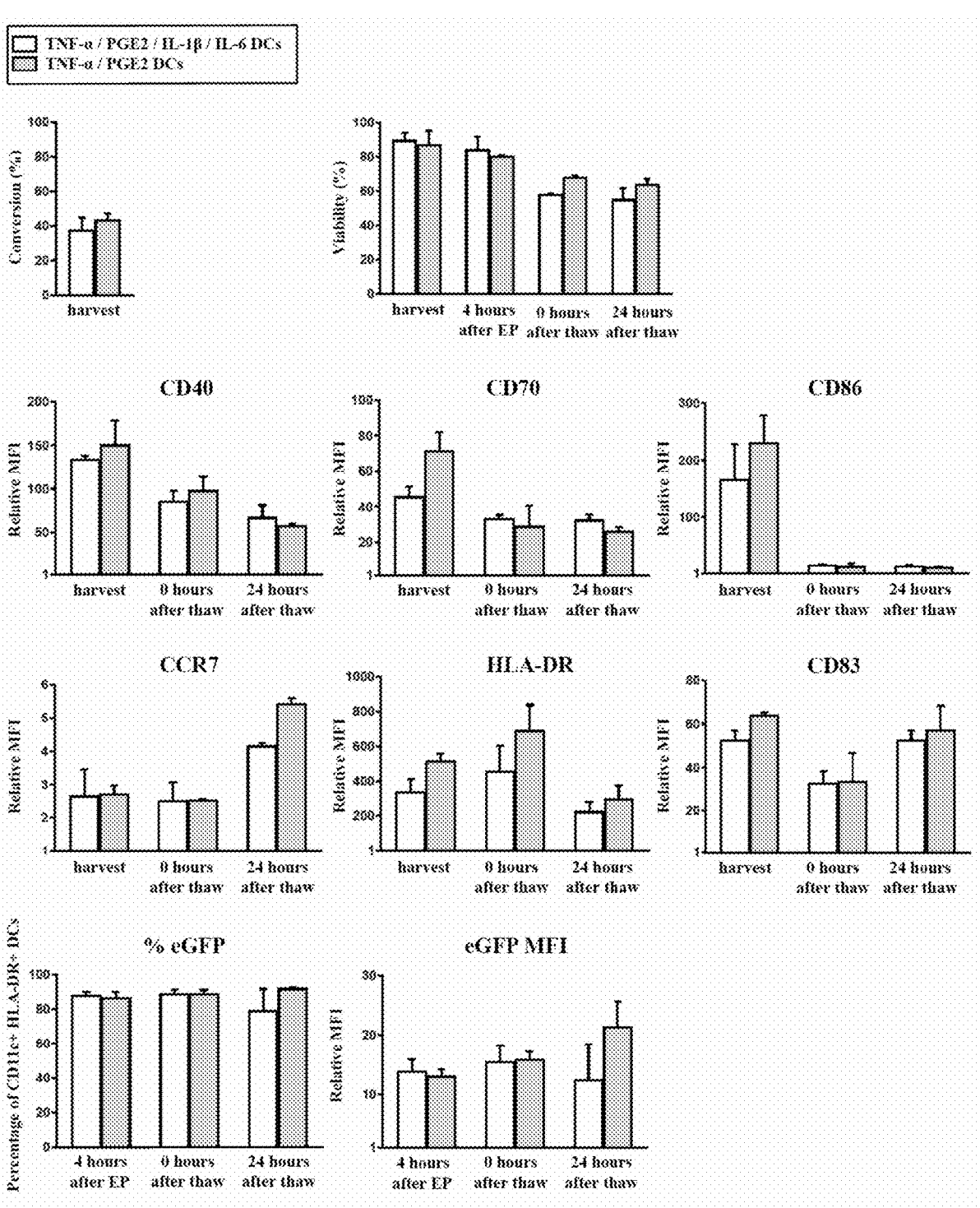
FIG. 9. DC phenotype compared between 8-day TNF-α/PGE2/IL-1β/IL-6-matured moDCs and 8-day TNF-α/PGE2-matured moDCs (n=3), as determined at different timepoints. Whenever relevant, the time points 'at harvest', '4 hours after EP', 'immediately after thaw' and '24 hours later in the absence of cytokines' were included in the assay. (A) monocyte-to-DC conversion rate at harvest (trypan blue); (B) viability (trypan blue) in time; (C) comparison of cell surface expression of phenotypical and maturation markers in time, calculated as relative MFIs (ratio of geometric mean of the positive fluorescence signal over background fluorescence, gated within live CD11c$^{high}$ HLA-DR$^{high}$ DCs); (D) The intensity of the eGFP expression level in time, depicted as a percentage of eGFP+ cells within live CD11c$^{high}$ HLA-DR$^{high}$ cells and relative MFI. The geometric mean of MOCK-EP DCs served as background staining. Statistics: bar graphs represent median with 95% C.I.

We then compared this 4-day moDC differentiation protocol with an established "classical" clinical-grade 8-day DC-culture in terms of several key parameters relevant to vaccine production. 8-day moDCs were generated in GM-CSF/IL-4-supplemented culture medium and matured for the last 2 days by addition of TNF-α and PGE2. Although the original maturation cocktail as first described by Jonuleit et al (1997) consisted of TNF-α, PGE2, IL-1β and IL-6, we and others have observed that the omission of IL-1β and IL-6 has no detrimental effect on viability, differentiation and maturity of the DCs thus generated (FIG. 9), nor does it have an negative impact on DC functionality (Van Driessche et al. 2009).

Figure 2A:
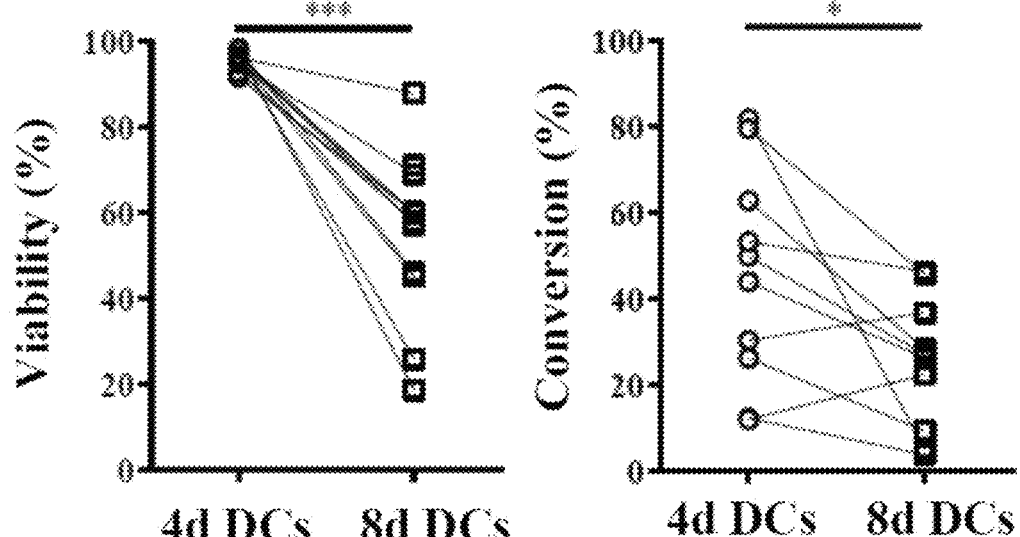
FIG. 2. DC profile at harvest compared between 4-day moDCs and 8-day moDCs (n=10): (A) viability and monocyte-to-DC conversion rate (flow cytometry); (B) comparison of cell surface expression of phenotypical and maturation markers, calculated as relative MFIs (ratio of geometric mean of the positive fluorescence signal over background fluorescence, gated within live $CD11c^{high}$ $HLA-DR^{high}$ DCs). Statistics: Wilcoxon matched-pairs signed rank test.

First, we consistently observed that 4-day moDCs were significantly more viable (p-value 0.0010) than 8-day moDCs at harvest with a median viability (flow cytometry) of 96.3% [95% CI: 92.7-98] compared to 58% [95% CI: 45.1-69.1]. The 4-day moDCs also gave rise to the highest median monocyte-to-DC conversion rate (46.9% [95% CI: 27.2-63.2] vs 26.8% [95% CI: 14.1-36.2]), reaching statistical significance (p-value 0.0195) (FIG. 2A).

Figure 2B:
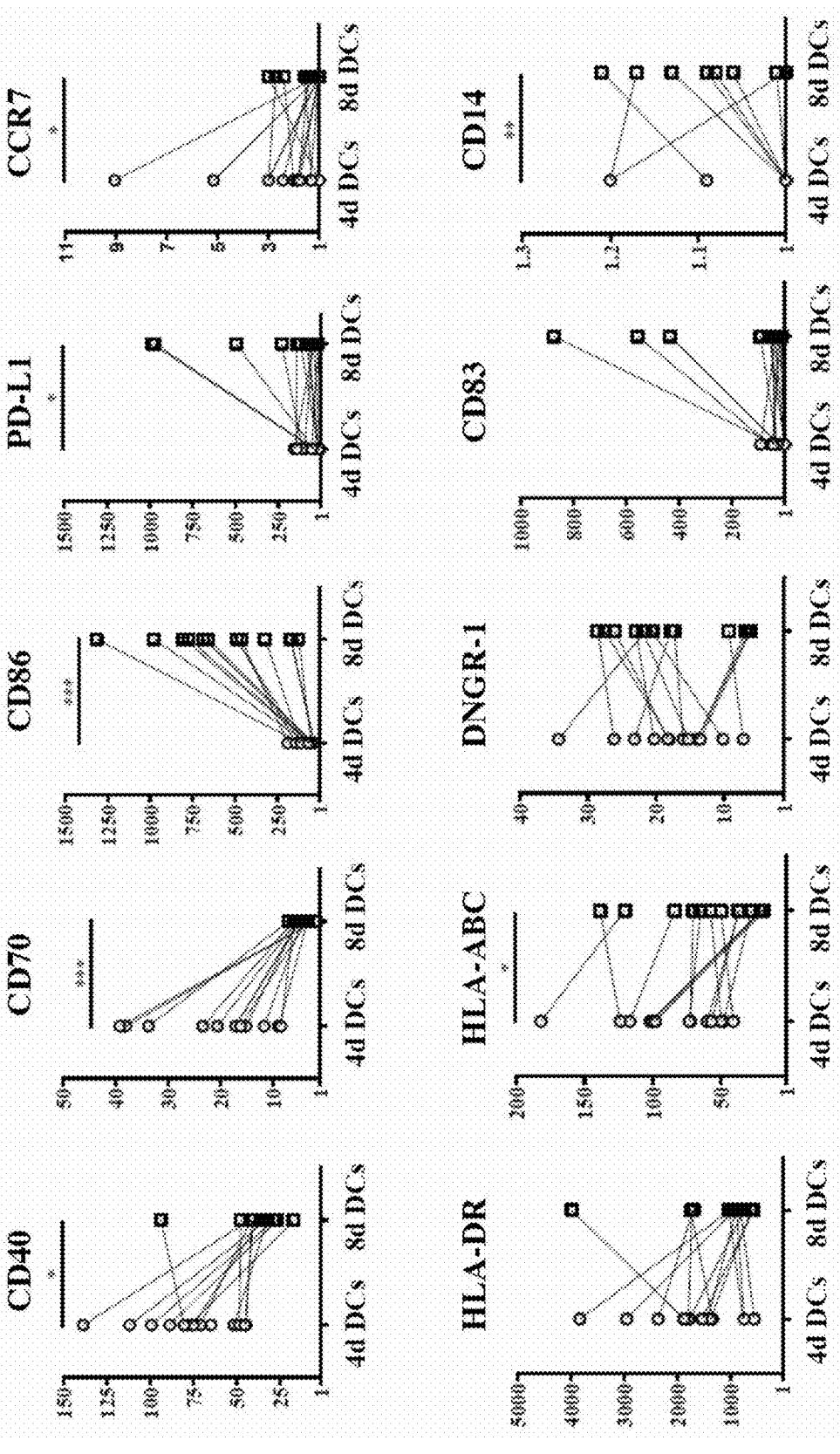

Next, we looked at the difference in phenotypical profile at harvest. 4-day moDCs, displayed significantly higher levels (MFI) of CD40, CD70 and HLA-ABC than standard 8-day moDCs. Unexpectedly, CCR7 was also expressed at higher levels on MPLA/IFN-γ-matured 4-day moDCs, despite the absence of exposure to PGE2. By contrast, expression of CD86 is higher in 8-day moDCs (FIG. 2B and Table 1). CD83, HLA-DR and DNGR-1 showed no statistically significant difference in expression across both DC-culturing protocols. Unexpectedly, PD-L1 expression was consistently higher (four-fold on average) in standard 8-day compared to 4-day moDCs, and even further increased after thawing of cryopreserved DC aliquots (FIG. 10).

TABLE 1

| Rel MFI* at harvest | 4d MPLA/IFN-γ mature DCs | 8d TNF-α/PGE2 mature DCs |
| --- | --- | --- |
| CD40 | 74.9 [95% CI: 48.4-99.3] | 40.4 [95% CI: 28.1-47.4] |
| CD70 | 17.1 [95% CI: 11.6-38.1] | 5.0 [95% CI: 1.9-5.9] |
| CD86 | 52.8 [95% CI: 36.1-113] | 491.8 [95% CI: 172.6-807.4] |
| PD-L1 | 41.9 [95% CI: 14.4-110.2] | 84.9 [95% CI: 42.9-494.9] |
| CCR7 | 2.0 [95% CI: 1.35-3.02] | 1.0 [95% CI: 1.0-2.4] |
| CD83 | 31.8 [95% CI: 2.4-47.2] | 47.3 [95% CI: 19.8-435.8] |
| HLA-DR | 1542 [95% CI: 771.5-2365] | 919.5 [95% CI: 749.5-1732] |
| HLA-ABC | 72.9 [95% CI: 49.5-116.8] | 49.9 [95% CI: 21.0-83.6] |

TABLE 1-continued

| Rel MFI* at harvest | 4d MPLA/IFN-γ mature DCs | 8d TNF-α/PGE2 mature DCs |
| --- | --- | --- |
| DNGR-1 | 15.9 [95% CI: 13.4-23.1] | 20.5 [95% CI: 6.7-26.0] |
| CD14 | 1.0 [95% CI: 1.0-1.09] | 1.01 [95% CI: 1.0-1.13] |

*Background signal: geometric mean of alive CD11c$^{high}$ HLA-DR$^{high}$ DCs

From these data, we conclude that reducing monocyte culture duration by half, in combination with the activation factors MPLA and IFN-γ gives rise to fully differentiated, mature DCs with a higher conversion yield, higher cellular viability, and no detrimental impact on costimulatory molecule expression levels.

To our knowledge, only one report described the integration of MPLA+IFN-γ as maturation cocktail in an accelerated DC-differentiation protocol with a monocyte-to-DC-differentiation period of only 24-36 hours (Massa et al. 2013). However, the consequence on the activity of a DC vaccine was not evaluated for said alternative DCs. As a comparison, monocyte-derived dendritic cells were generated either according to the protocol described herein before ("MIDRIX DCs"), or according to the alt-2 protocol described by Massa et al. ("Massa DCs"). CD14+ monocytes were isolated from buffy coats as described herein before. DCs were harvested at respective timepoints and electroporated with eGFP-encoding mRNA. Data were derived from 6 different donors and the following aspects were evaluated:

(A) Viability and absolute cell yield at harvest of live CD11c+ HLA-DR+ dendritic cells obtained with both protocols;

(B) Expression of the monocyte marker CD14 vs the DC differentiation marker CD83;

(C) Expression of the DC maturation markers CD40, CD70, CD86 and CCR7;

(D) Expression of the T-cell co-inhibitory receptor PD-L1;

(E) Electroporation efficiency, expressed as levels of translated protein (relative mean fluorescence intensity of eGFP signal) as well as fraction of cells with successful translation of electroporated eGFP-mRNA (percentage eGFP+ DCs), as measured 4 hours after electroporation.

As can be seen in FIG. 13 the duration of the differentiation step of 24 to 36 hours was not enough in order to achieve sufficient differentiation of the monocytes into DCs, as well as to generate sufficient phenotypical features of maturation which are correlated with T-cell stimulatory capacity. Importantly, absolute yields of viable DCs were significantly lower using the protocol described by Massa et al. compared to the method of the present invention, which was seen to significantly impair the possibility to further process these cells with electroporation and cryopreservation, and thus having an impact on the DC vaccine. "Massa DCs" were less susceptible to electroporation with mRNA encoding full-length protein, while DCs generated according to the present invention showed high electroporation efficiency.

In addition, "Massa DCs" display less downregulation of the monocyte marker CD14, less upregulation of the DC differentiation marker CD83, and lower levels of the DC maturation/T-cell costimulatory receptors CD40, CD70 and CD86. Levels of CCR7, required for migration into T-cell zones of lymphoid tissues, are also less upregulated on D1

DCs. Even more, PD-L1 levels showed a trend towards higher expression on "Massa DCs".

Both MPLA and IFN-γ are Necessary Together to Confer Short-Term Cultured DCs a Fully Mature Phenotype and the Capacity to Induce De Novo T Helper 1 Polarization We next dissected the relative contribution of MPLA, IFN-γ or the combination to the phenotypical maturation status, as well as to the functional impact in terms of T helper-polarization capacity of 4-day-cultured moDCs.

Figure 3:
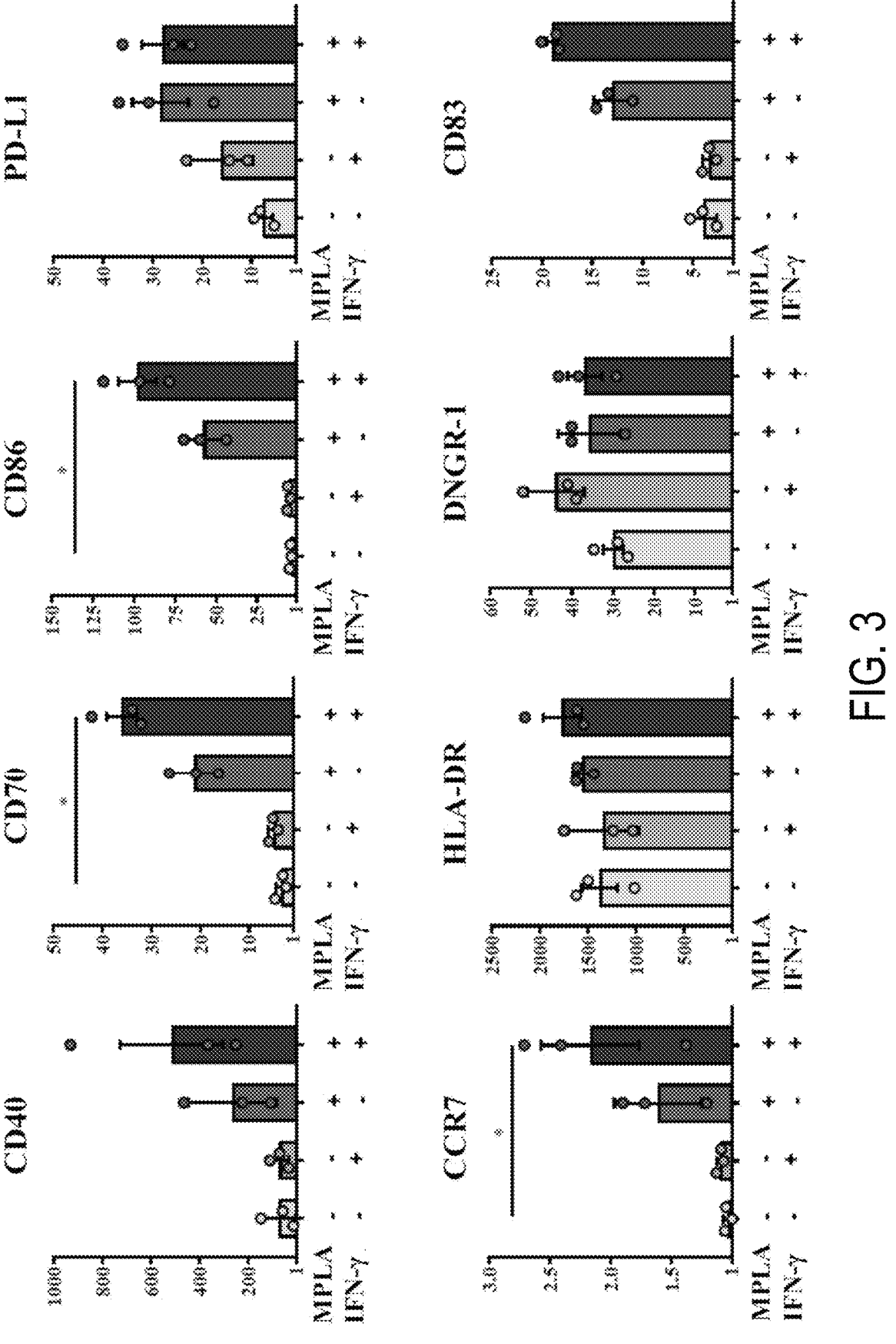
FIG. 3. Relative contribution of MPLA, IFN-γ or both to the induction of maturation profile in 4-day moDC at harvest (n=3). Relative MFIs of DC maturation markers, shown as bar graphs. Statistics: Kruskal-Wallis combined with the Dunn's multiple comparisons test.

We found that both maturation stimuli were required to maximize surface expression levels of the T-cell costimulatory molecules CD40, CD70, CD86, as well as CD83 and CCR7 (FIG. 3). This effect was not observed with respect to expression of HLA-DR or DNGR-1, the latter remaining stable relative to immature DCs. Of note is the observation that PD-L1 induction on moDCs was primarily driven by MPLA rather than IFN-γ exposure.

Figure 4A:
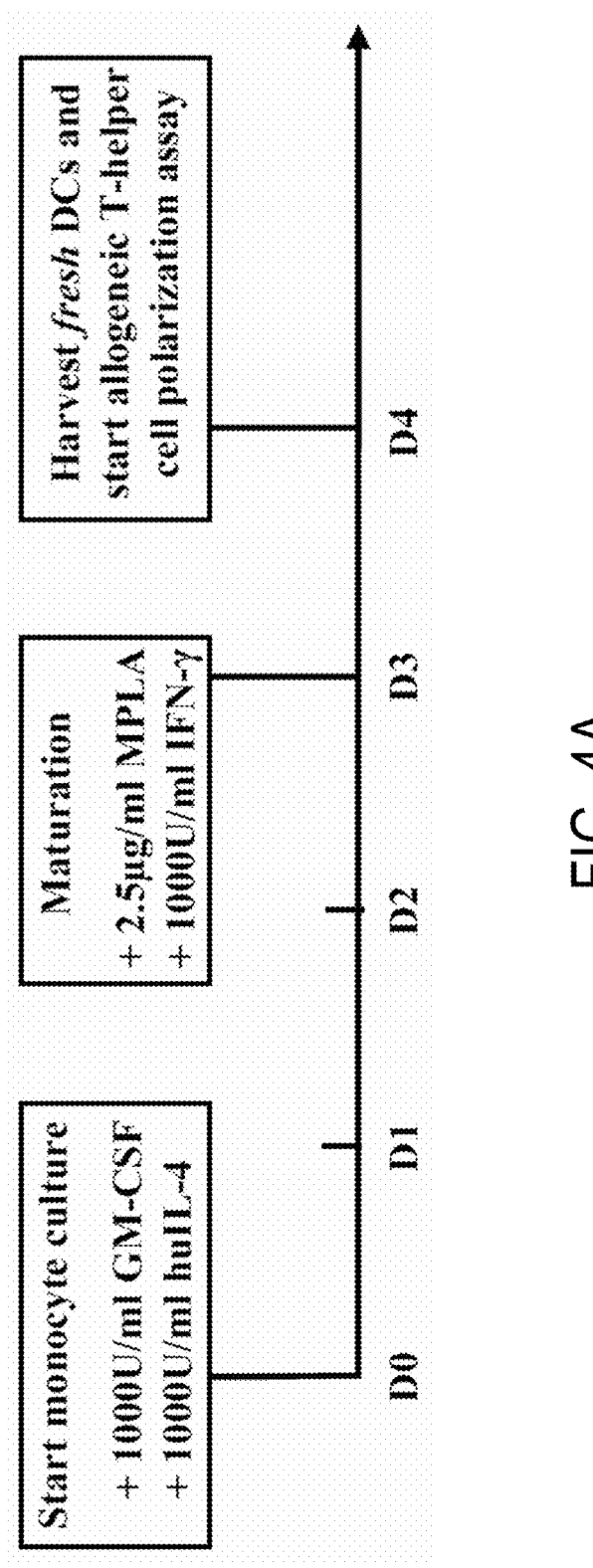
FIG. 4. Combinatorial effect of MPLA and IFN-γ on 4-day moDCs in terms of naive T helper polarization potential, (n=6 to 12 replicates pooled from repeat experiments with 2 different DC donors and 3 different allogeneic T-cell donors). (A) Schematic of experiment timeline for allogeneic naive T helper cell polarization assay. (B) Representative dot plots showing the CD4+ T-cell IFN-γ/IL-10 cytokine production within CD4+ T-cells after 14 days co-culture with immature or fully matured allogeneic DCs. (C) Relative contribution of MPLA, IFN-γ or the combination on DC-mediated naive T helper cell polarization: bar graphs indicate percentage of CD4+ cells showing intracellular expression of IFN-γ, IL-10, IL-4, and IL-17 respectively.
Figure 4B:
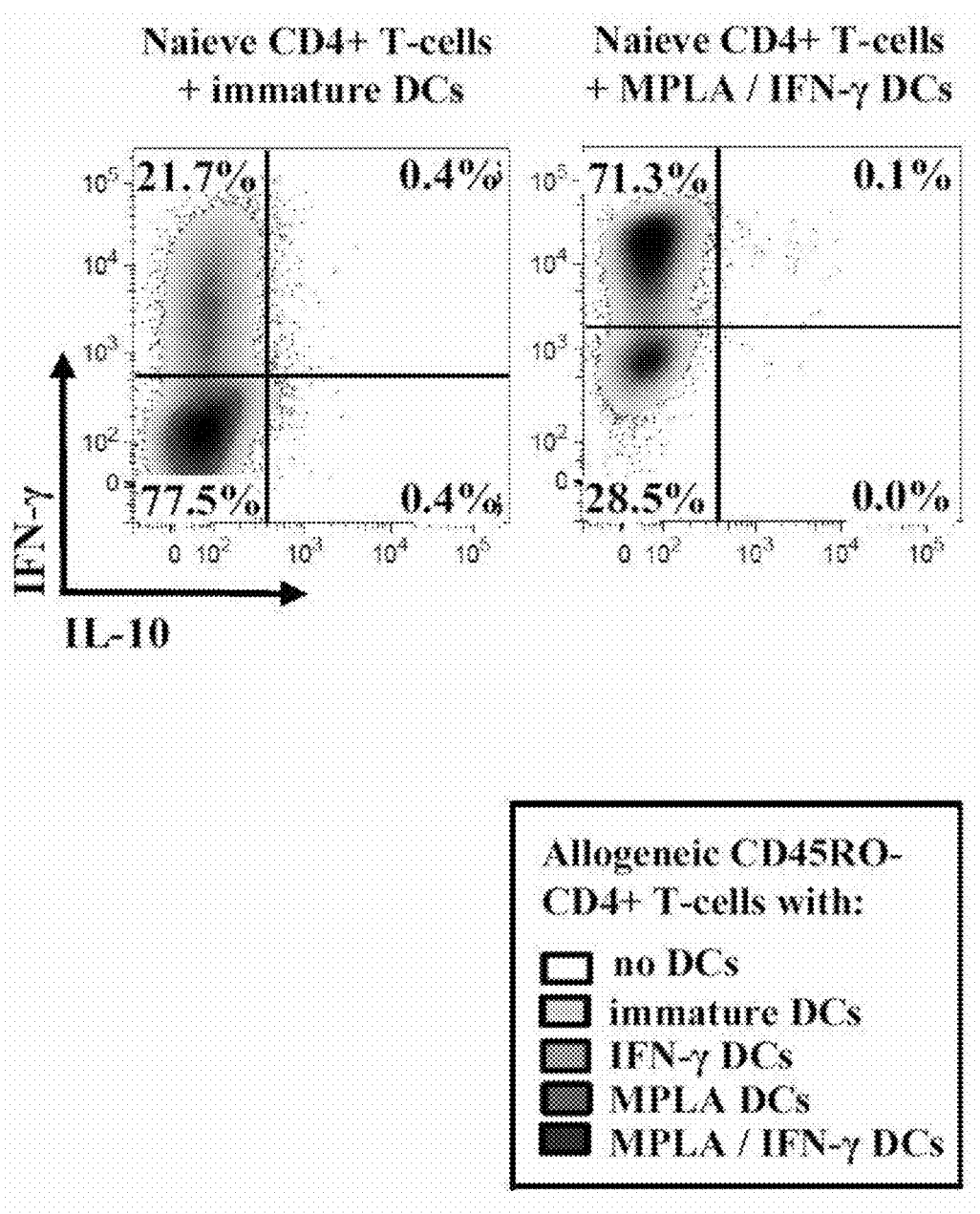
Figure 4C:
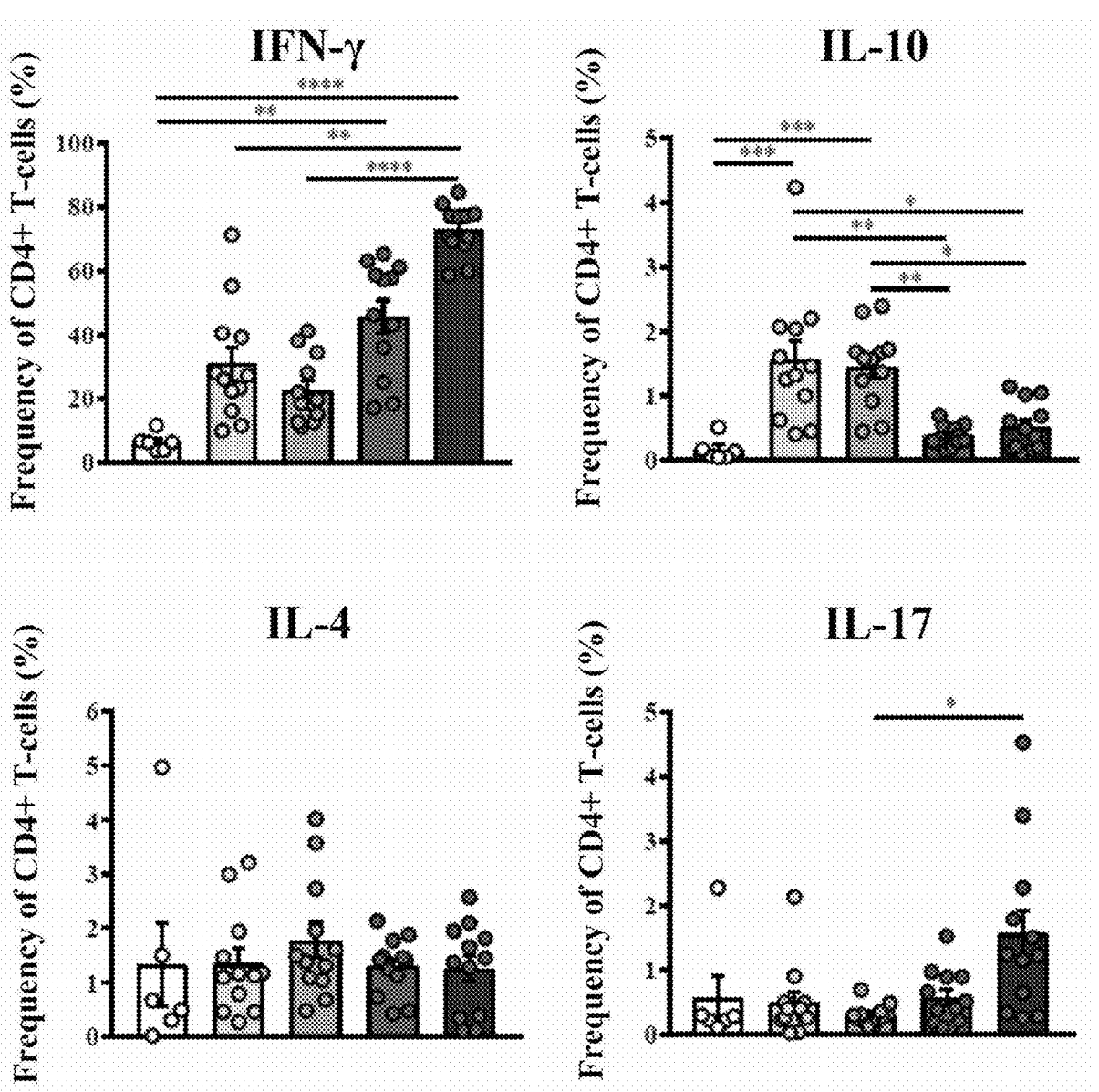

On the functional level, maximal induction of IFN-γ secretion by naive allogeneic CD4+ T-cells was only achieved by prior exposure of the DCs to both MPLA and IFN-γ. Limited amounts of IL-10 production were induced by immature DCs in naive T helper cells, and this was further suppressed in the presence of MPLA pre-exposed DCs, regardless of prior IFN-γ exposure. T helper cell IL-4 production was only induced at low levels, as was IL-17 which showed a small increase in the presence of MPLA/IFN-γ-matured DC (FIG. 4).

Thus, exposure of short-term-differentiated moDCs to both MPLA and IFN-γ together is necessary to obtain a fully mature phenotype and endow these cells with the capacity to induce robust de novo type 1-polarized T helper cell responses.

Short-Term Cultured DCs Exhibit Superior Resiliency to Electroporation Together with High mRNA Translational Efficiency In addition to phenotypical maturation and type-1 immune polarization potential, sufficient DC quantities should be recovered following the stress of electroporation and cryopreservation in order to be implementable in clinical practice.

We first assessed the ability of MPLA/IFN-γ-matured, short-term cultured DCs to successfully and stably express protein antigens derived from electroporated antigen-encoding mRNA. Using eGFP-encoding mRNA as a marker for electroporation efficiency we looked at eGFP expression 4 hours after electroporation/before cryopreservation, immediately after cell thawing, and 24 hours after cell thawing following further incubation in cytokine-free medium.

Figure 5A:
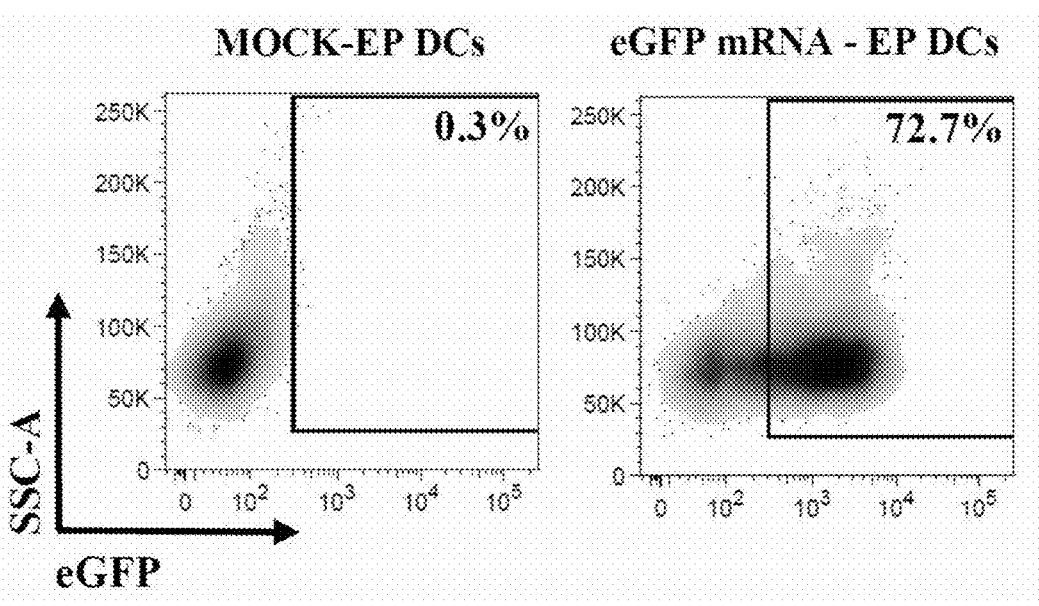
FIG. 5. (A) Representative dotplots of 4-day moDCs, EP with either vehicle (MOCK-EP) or eGFP mRNA (1 µg mRNA/10e6 DCs), showing the eGFP expression level of viable $CD11c^{high}$ $HLA-DR^{high}$ DCs 4 hours post-electroporation. (B) The intensity of the eGFP expression level in time, depicted as a percentage of viable $CD11c^{high}$ $HLA-DR^{high}$ DCs and relative MFI. The geometric mean of MOCK-EP DCs served as background staining. The time points include 4 hours after EP (n=9), immediately after thaw (n=9) and 24 hours later in the absence of cytokines (n=3) were included in the assay. (C) Viability (trypan blue) and recovery percentages of 4-day moDCs after being electroporated with eGFP-mRNA (n=17). The recovery rate was calculated as the division of the number of viable DCs (trypan blue) post-versus pre-electroporation. (D) Viability (trypan blue) and recovery rate comparisons between 4-day and 8-day moDCs after EP with eGFP mRNA (n=8). (B-C) Statistics: Kruskal-Wallis combined with Dunn's multiple comparisons test; (D) Wilcoxon matched-pairs signed rank test.
Figure 5B:
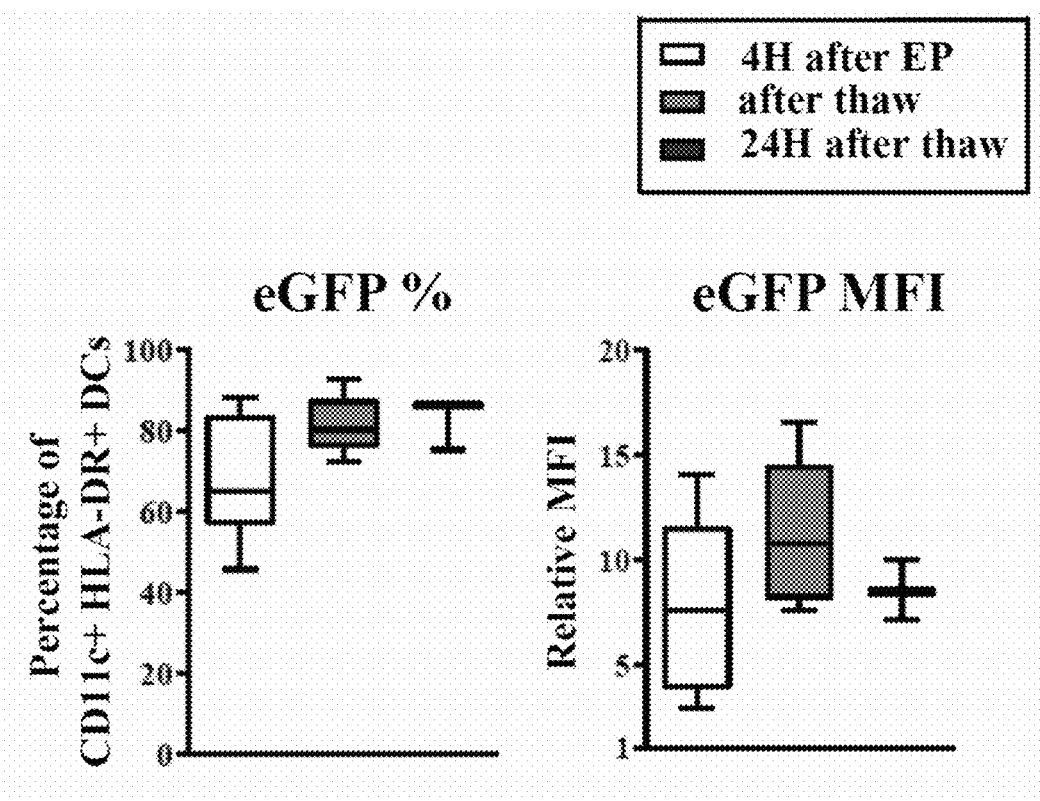

The median percentage of eGFP positive DCs electroporated by exponential pulse evolved from 64.8 [95% CI: 55.2-87.7] before cryopreservation, to 80.2 [95% CI: 73.1-87.7] immediately after thawing and remained stable in the following 24 hour period (86.3 [95% CI: 75.2-86.4), with no significant change in expression intensity (MFI) over that time period (FIG. 5A, B).

Figure 5C:
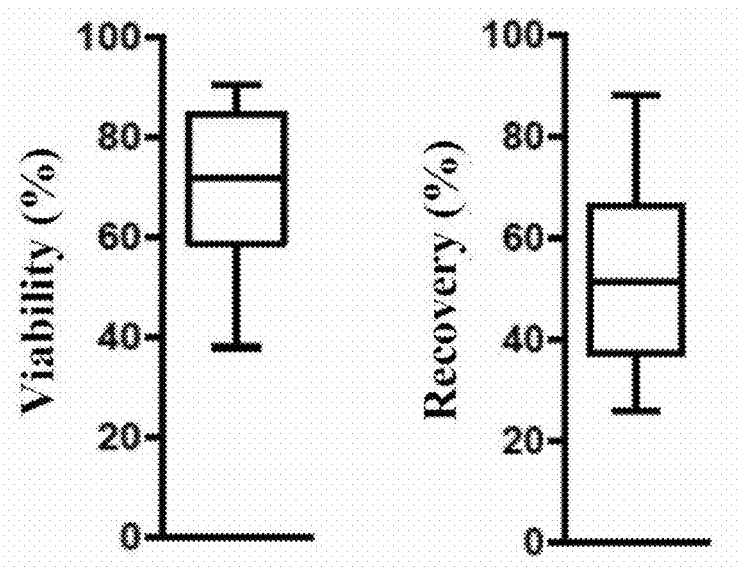
Figure 5D:
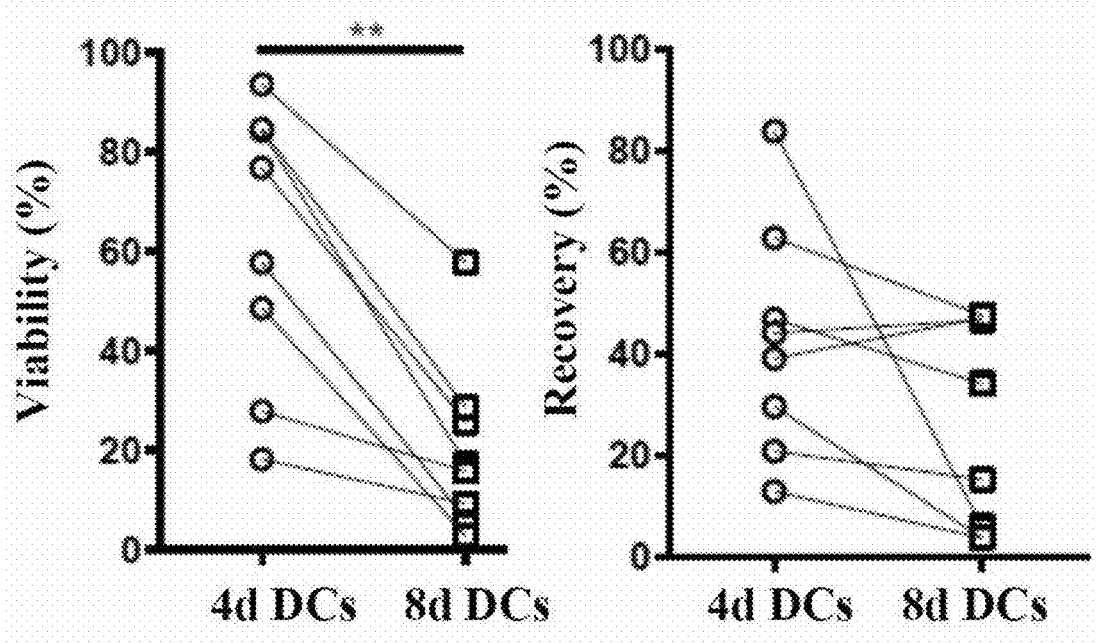

Exponential pulse electroporation led to an average decrease in viability (trypan blue) of 17.3% in 4-day moDCs. In combination with electroporation-induced net cellular loss, this translated into a median percentual live DC recovery of 51.4% [95% CI: 36-67%] (live cells recovered post-vs pre-electroporation) (FIG. 5C). Using a separate series of donors, we compared 4-day MPLA/IFN-γ moDCs to standard 8-day moDCs in terms of resiliency to electroporation. We observed that 4-day DCs were significantly more viable (trypan blue) than 8-day DCs after EP with a median viability of 67.3% [95% CI: 18.2-93.5] vs 16.5% [95% CI: 2.8-57.8]. 8-day moDCs were also more susceptible to net cellular loss after eGFP mRNA EP, with a mean live cell recovery rate of 24.6% [95% CI: 3.7-47.5] compared to 41.5% [95% CI: 12.8-83.8] with 4-day moDCs. (FIG. 5D)

Figure 11:
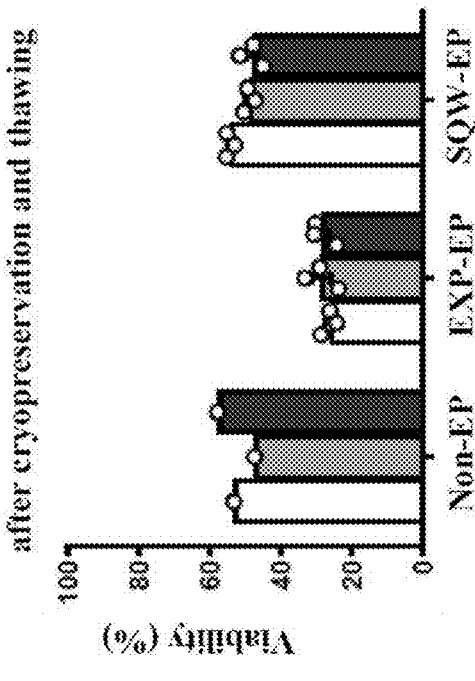
FIG. 11. DC viability was assessed 4 h after electroporation (or further incubation for non-electroporated conditions), and after freezing and thawing. Short DC culture: 3 days GM-CSF/IL-4; 24 hours MPLA (2,5 μg/mL) and IFN-γ (1000 U/mL). At harvest, DCs were divided among following electroporation settings.
Figure 11:
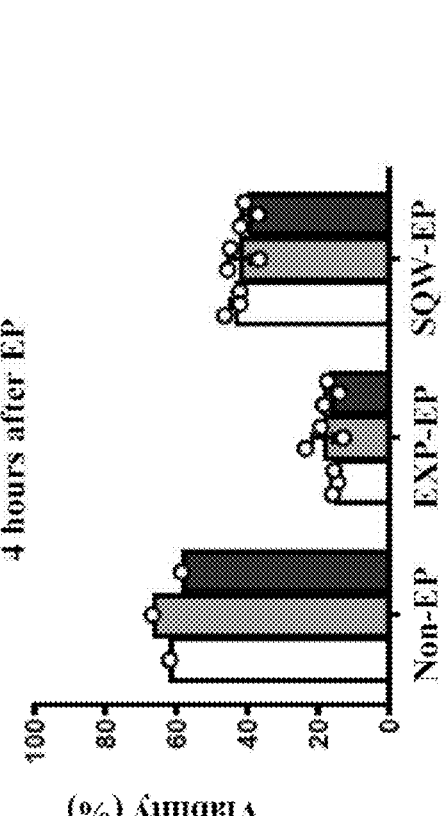

In further tests we evaluated the outcome after square wave pulse electroporation. Using small-scale runs using DCs produced across a range of cytokine concentrations, we found that cell viability after electroporation and after cryopreservation was consistently higher using the square wave pulse as compared to the exponential pulse program (FIG. 11).

Figure 12A:
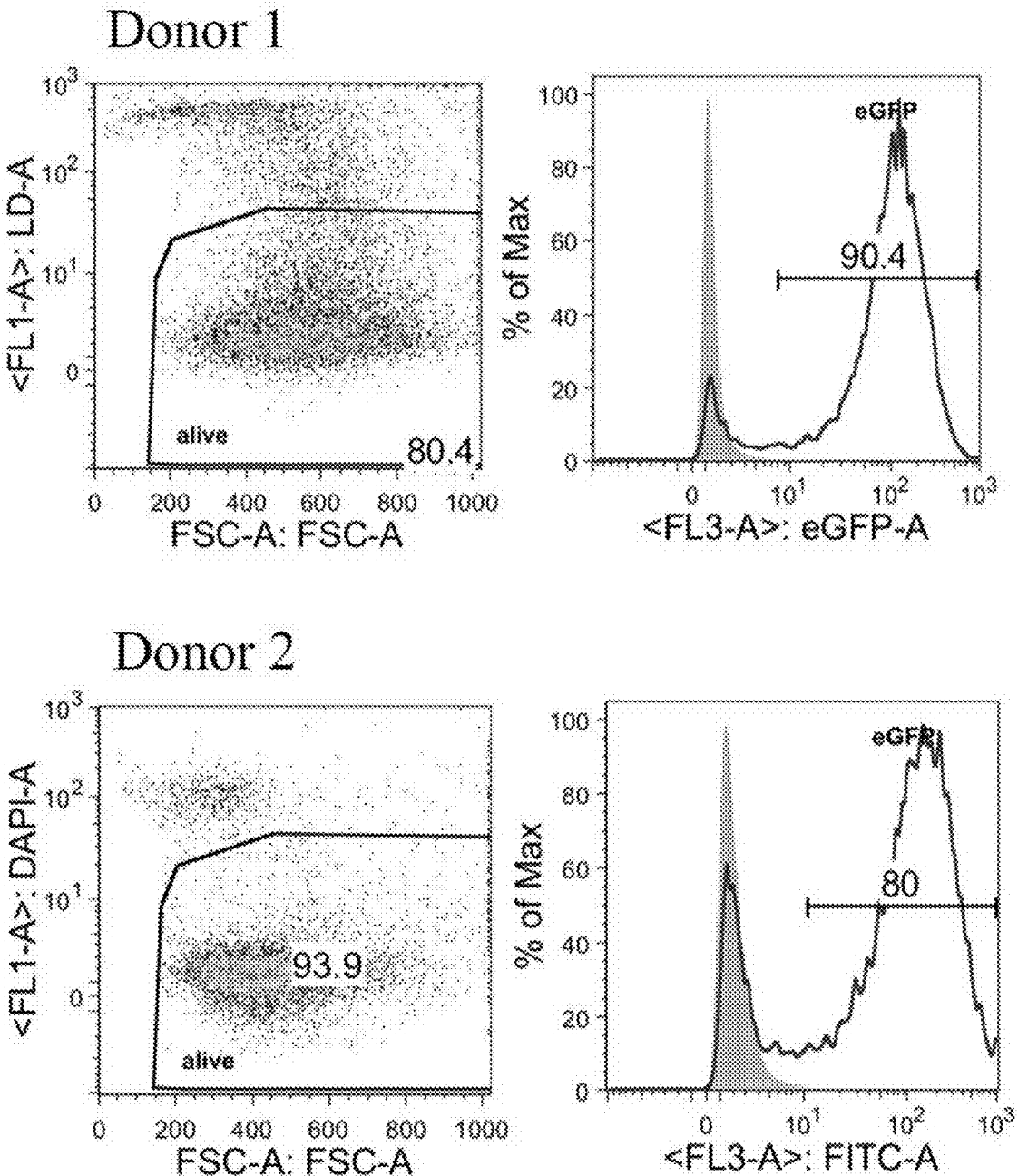
Figure 12B:
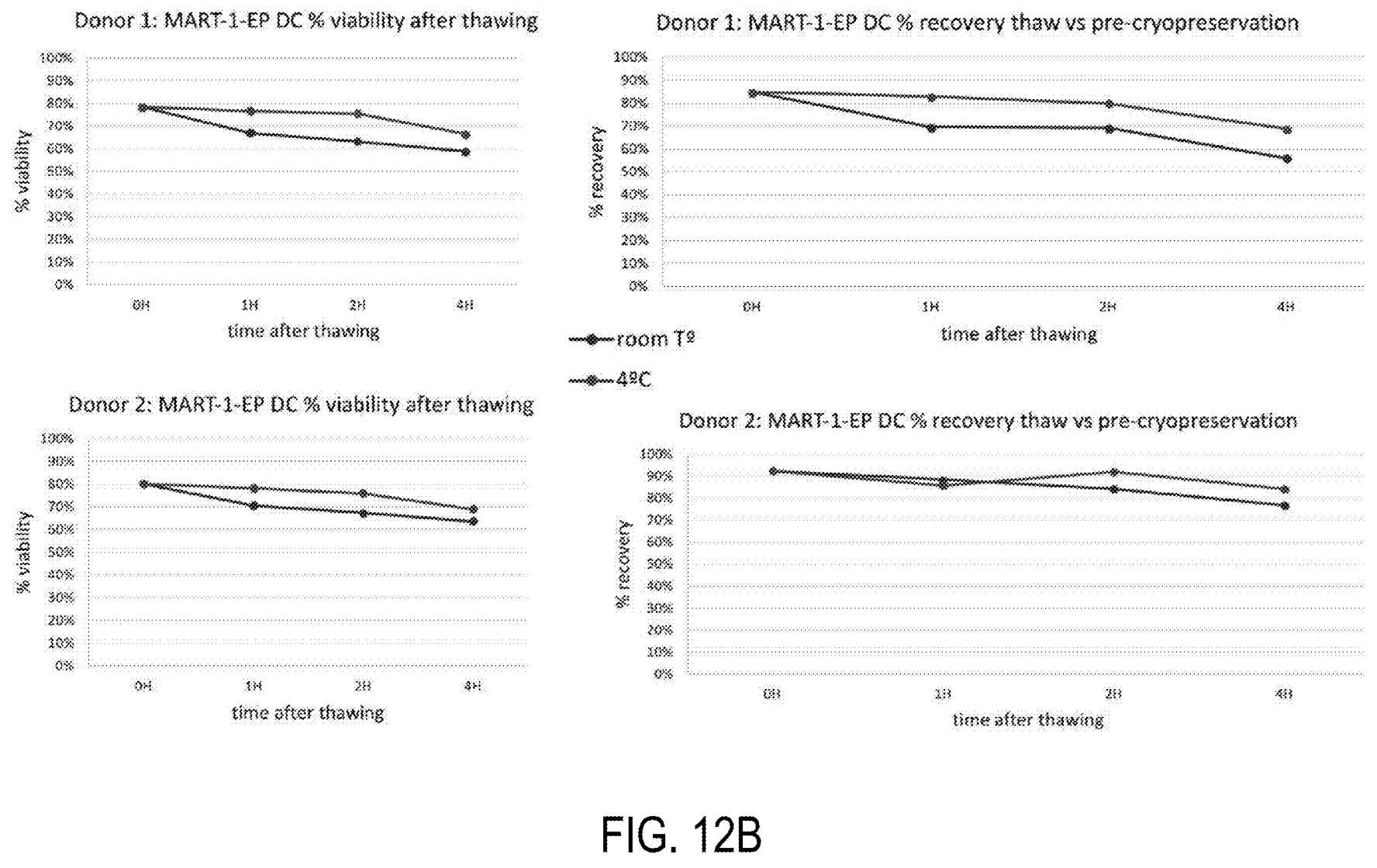
Figure 13A:
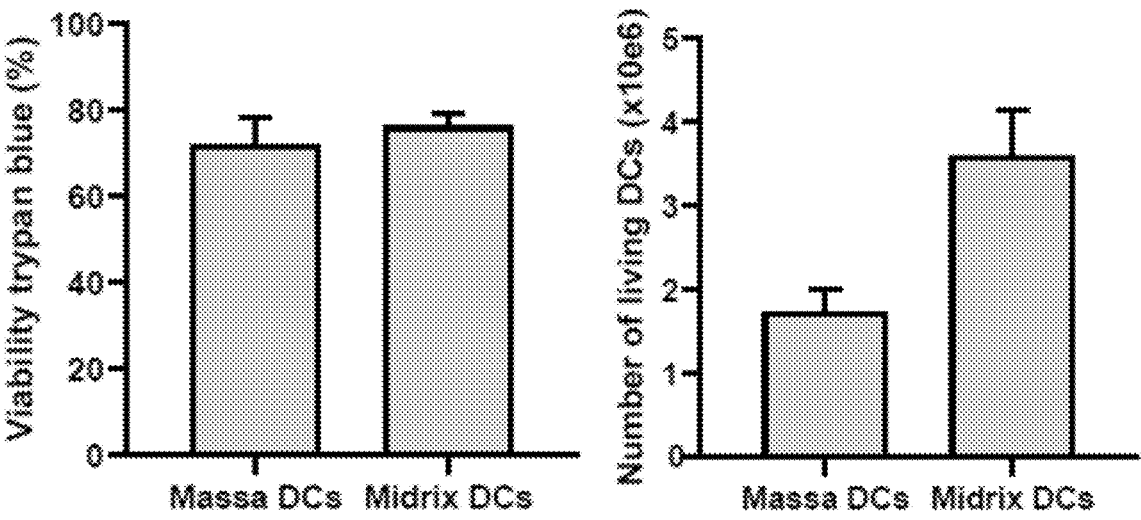
Figure 13B:
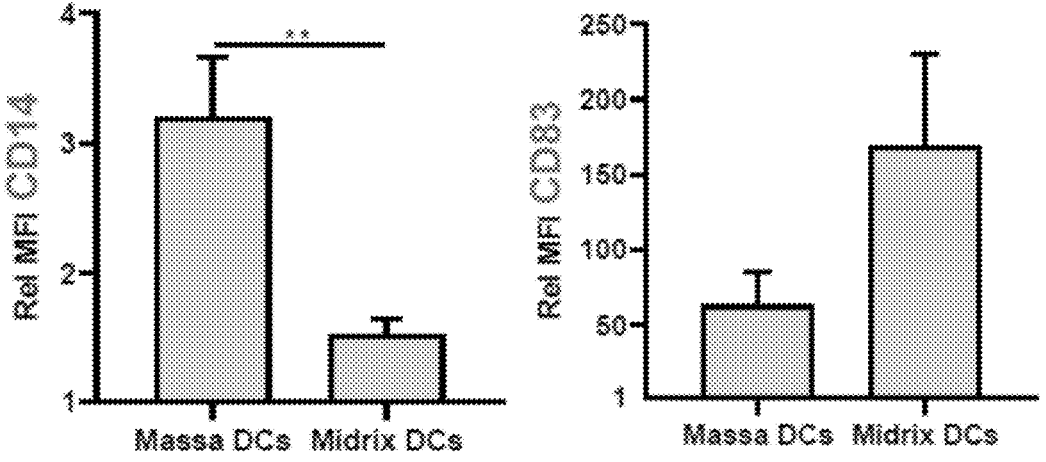
Figure 13C:
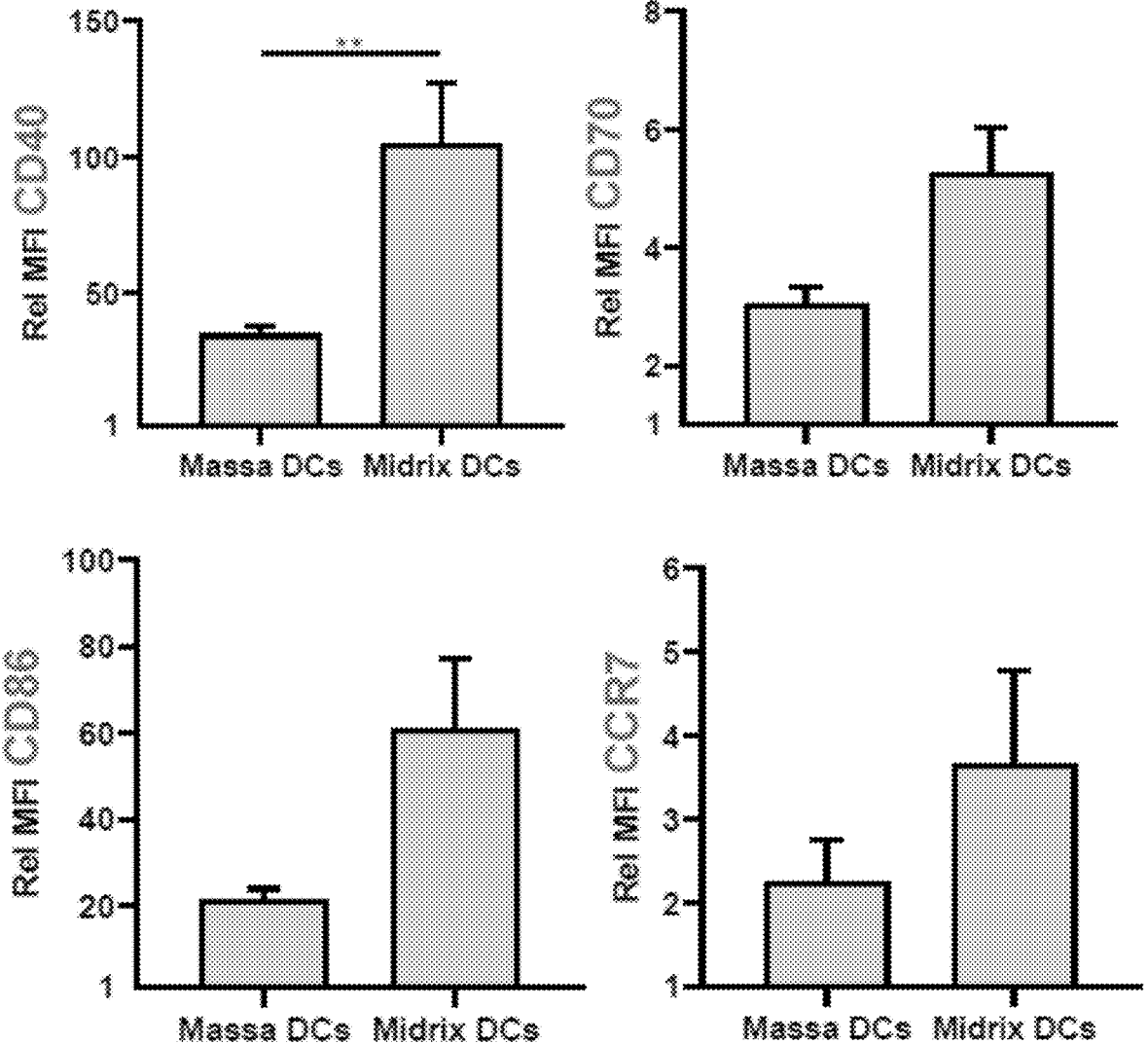
Figure 13D:
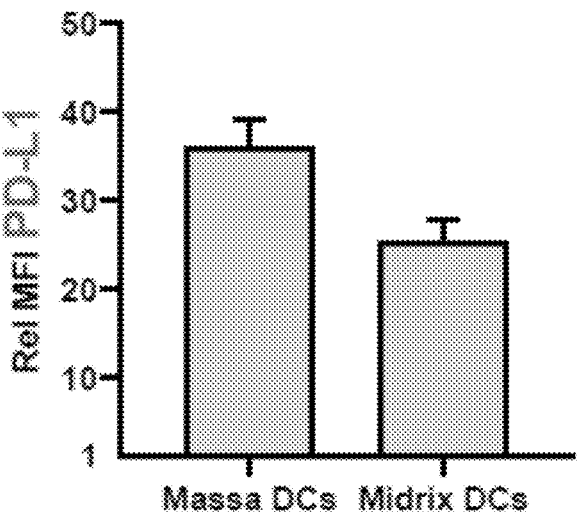
Figure 13E:
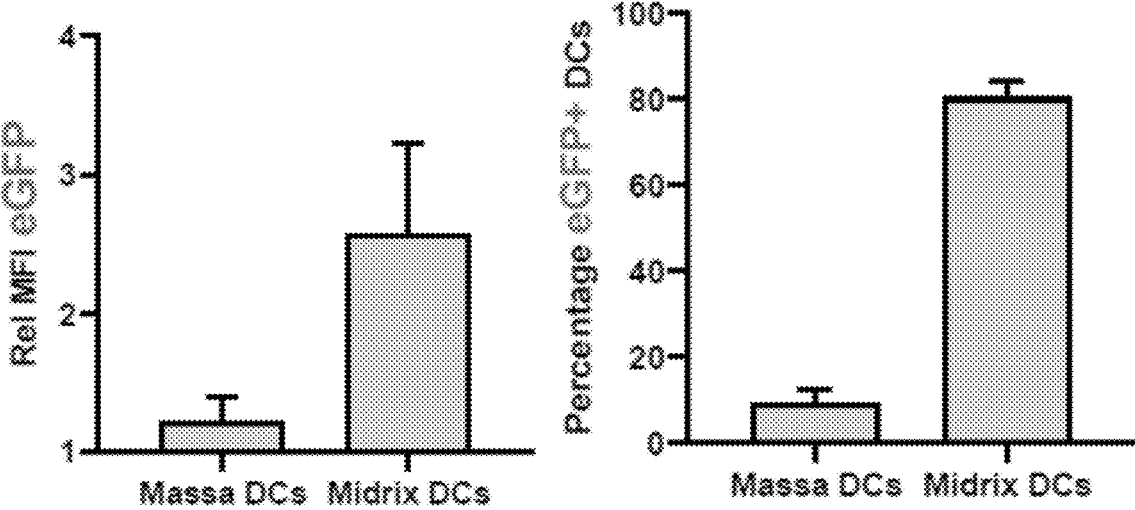

Further evaluation of the square-wave pulse was performed on full-scale DC production rounds in a GMP environment. Flow cytometry analysis of eGFP expression by DCs electroporated using square wave pulse was non-inferior compared to exponential pulse in terms of % eGFP positive cells (representative data shown in FIG. 12A). Electroporation by square wave pulse resulted in DC recovery immediately after thawing) of >80% cryopreserved DCs with a viability of >75% (FIG. 12B).

No formation of macroscopic cellular aggregates were observed after square-wave pulse electroporation, which greatly facilitates further cell handling and improves overall cell recovery (results not shown).

Figure 6A:
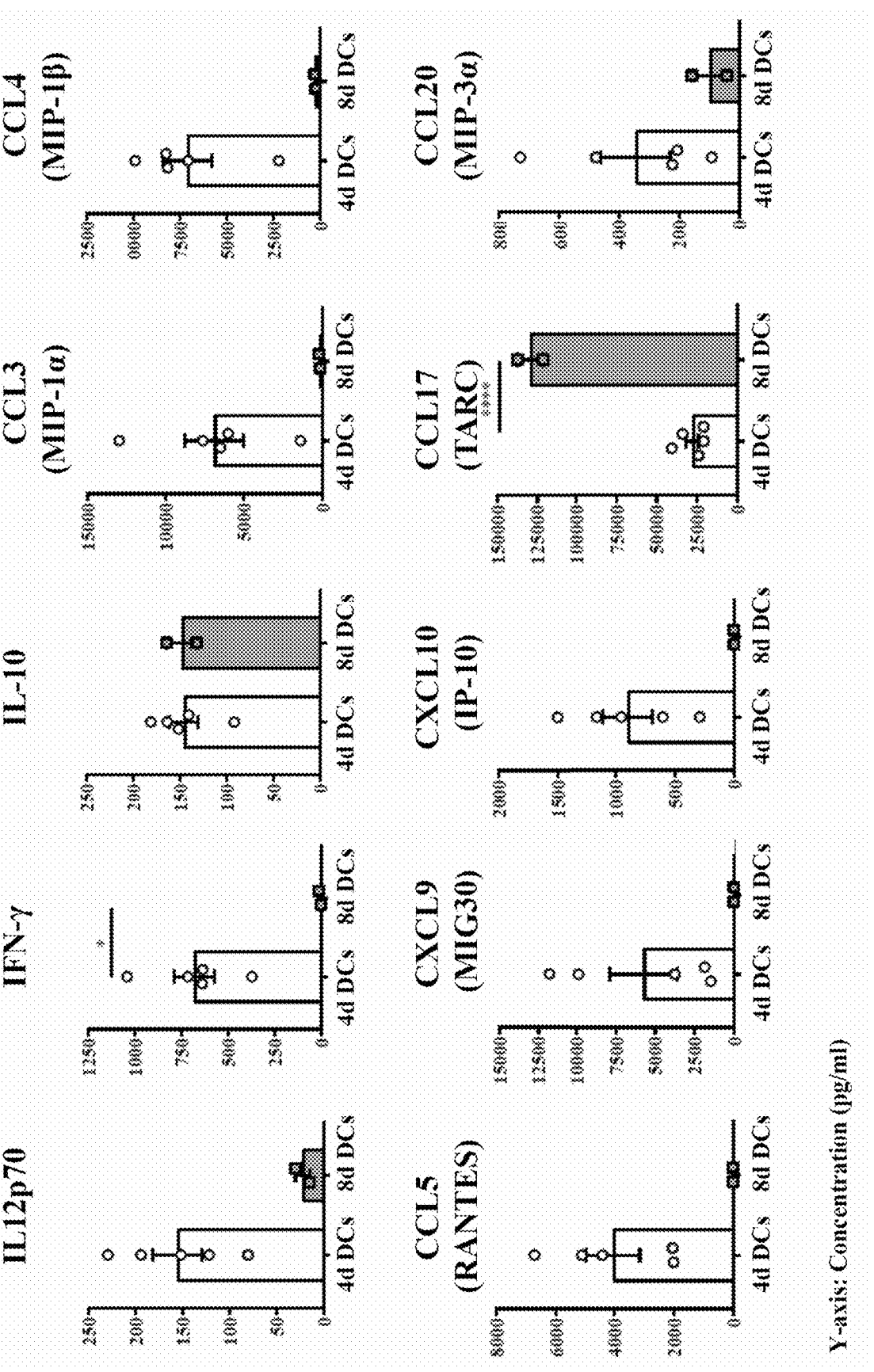
FIG. 6. (A) Cytokine and chemokine secretome of cryopreserved 4-day (n=5) and 8-day (n=2) eGFP mRNA-EP DCs, after an incubation period of 24 hours in cytokine-free medium, as measured using Luminex assay. Statistics: unpaired t-test. (B) Time line of cryopreserved EP-DCs in co-culture with allogeneic T helper cells. (C) T-cell polarization characteristics of electroporated DCs after cryopreservation and thawing (light grey bars). Allogeneic naive CD4+ T-cells without DCs served as negative control (white bars). (n=3 to 6 replicates pooled from repeat experiments with 2 different DC donors and 1 allogeneic T-cell donor). The data shows the percentage of cytokine-expressing CD4+ T-cells. Statistics: Mann-Whitney test.
Figure 6B:
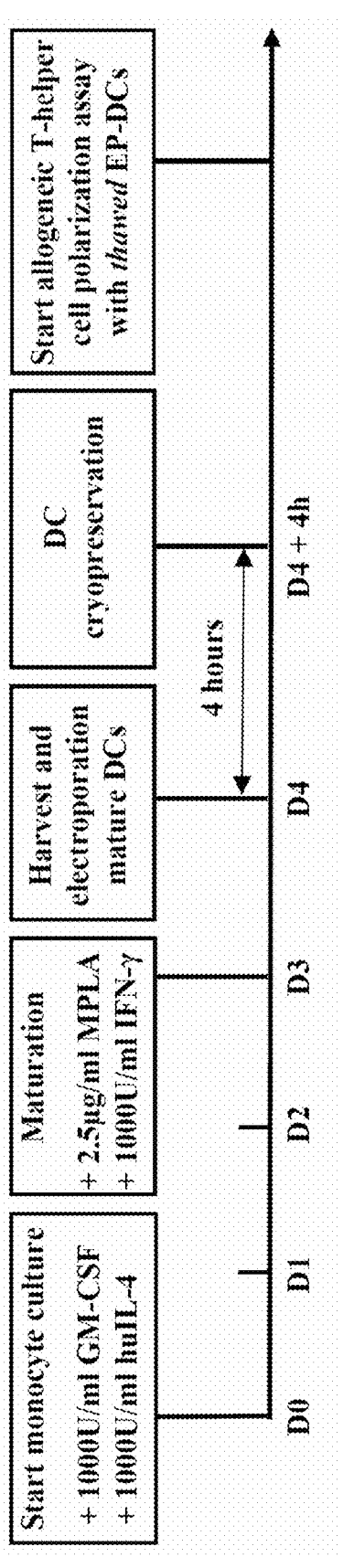

Electroporation and Cryopreservation does not Impair the Capacity of Short-Term Cultured DCs to Selectively Promote Type 1-Polarized T-Cell Responses A key DC property that should remain intact following the stress of electroporation and cryopreservation is the potential to selectively mobilize type-1-polarized and cytolytic T-cells when administered to patients. To provide an assessment of this functionality we analyzed the cytokine and chemokine secretome of electroporated and cryopreserved 4-day moDCs vs standard 8-day DCs following a 24 hour incubation period in cytokine-free medium (FIG. 6A). We found that 4-day moDCs were still capable of secreting bioactive IL-12 as well IFN-γ, while production of these cytokines by 8-day moDCs was below detection limits. No difference in IL-10 production was observed between both DC types. More strikingly, we found that only MPLA/IFN-γ-matured 4-day moDCs produced high amounts of chemokines involved in attracting type-1 polarized T helper cells, cytolytic T-cells and NK-cells (Colantonio et al. 2002), with no detectable secretion from standard 8-day moDCs. This includes high levels of the CXCR3 ligands CXCL9 (MIG30) and CXCL10 (IP-10) (Groom et al. 2011), as well as the CCR5 ligands CCL3 (MIP-1α), CCL4 (MIP-1β) and CCL5 (RANTES) (Samson et al. 1997). Secretion of the CXCR3 ligand CXCL11 (Groom et al. 2011) was below detection limits. By contrast, secretion of the T-reg- and Th2-mobilizing chemokine CCL17 (TARC) (Yoshie et al. 2015) was five-fold higher in standard 8-day moDCs. There was a trend towards higher release of Th17- and T-reg-attracting chemokine CCL20 (Yamazaki et al. 2008) by 4-day moDCs, while production of the T-reg-attracting CXCR4 ligand CXCL12 (SDF-1a) (Colantonio et al. 2002) did not differ between both DC culture protocols (data not shown).

Figure 6C:
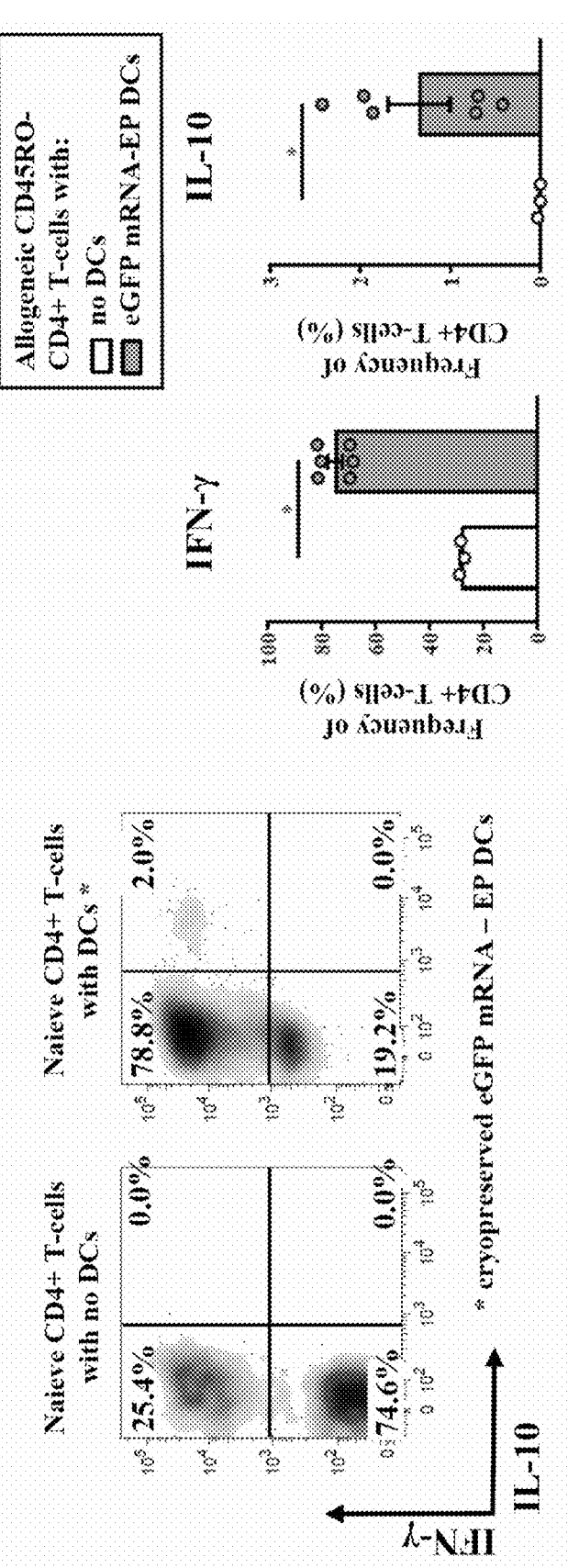

We also investigated whether electroporation and cryopreservation affected the capacity of 4-day moDCs to induce de novo T helper 1-polarized responses (FIG. 6C). Co-culture of allogeneic naive CD4 T-cells with thawed 4-day moDCs resulted in high IFN-γ production levels comparable to what was obtained with freshly harvested, unelectroporated 4-day moDCs (FIG. 4). Induction of IL-10 production was very low in this setting (FIG. 6C), consistent with the results obtained with fresh DCs (FIG. 4).

Short-Term Cultured DCs Efficiently Prime and Expand Tumor Antigen-Specific CD8+ T-Cells with Cytolytic Activity Having established the superiority of short-term cultured moDCs in terms of yield, phenotype, recovery after electroporation/cryopreservation, and the capacity to promote type-1 polarized T-cell responses, we next tested the capacity of these cells to present immunogenic epitopes from electroporated tumor antigen-encoding mRNA. Again, to reflect implementation of the DC vaccine in a real-life clinical setting, we performed all assays with cryopreserved rather than fresh mRNA-EP DCs. MART-1/Melan-A was used as model tumor-associated antigen given the possibility of detecting MART-1 specific CD8+ T-cells using tetramers in HLA-A2-positive healthy blood donors.

Figure 7A:
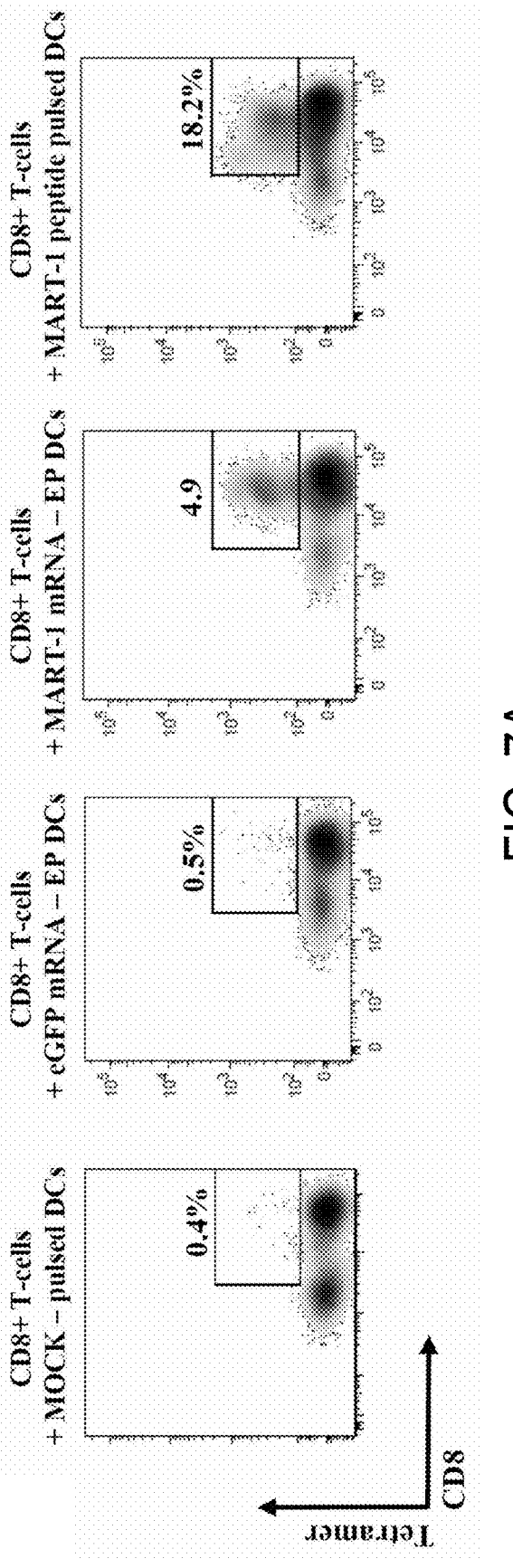
FIG. 7. (A) MACS-purified CD8+ T-cells from HLA-A2-positive donors were stimulated twice with autologous 4d-moDCs electroporated with the indicated mRNAs or pulsed with the AAAGIGILTV A2-restricted peptide from MART-1. Representative dot-plots showing expansion of tetramer-positive CD8+ T-cells. DCs used in all the assays were cryopreserved and thawed. (B) Summary of data obtained using different HLA-A2+ donors and CD8+ T-cells stimulated without DCs, with MOCK-pulsed DCs, with eGFP-mRNA-EP DCs, with MART-1 mRNA-EP DCs and with MART-1 peptide pulsed DCs (n=4 to 8 replicates pooled from repeat experiments with 2 different HLA-A2-positive donors). (C) Levels of intracellular IFN-γ and granzyme B in MART-1 specific CD8+ T-cells stimulated with the indicated DC conditions. (B-C) Statistics: Kruskal-Wallis with Dunn's multiple comparisons test.
Figure 7B:
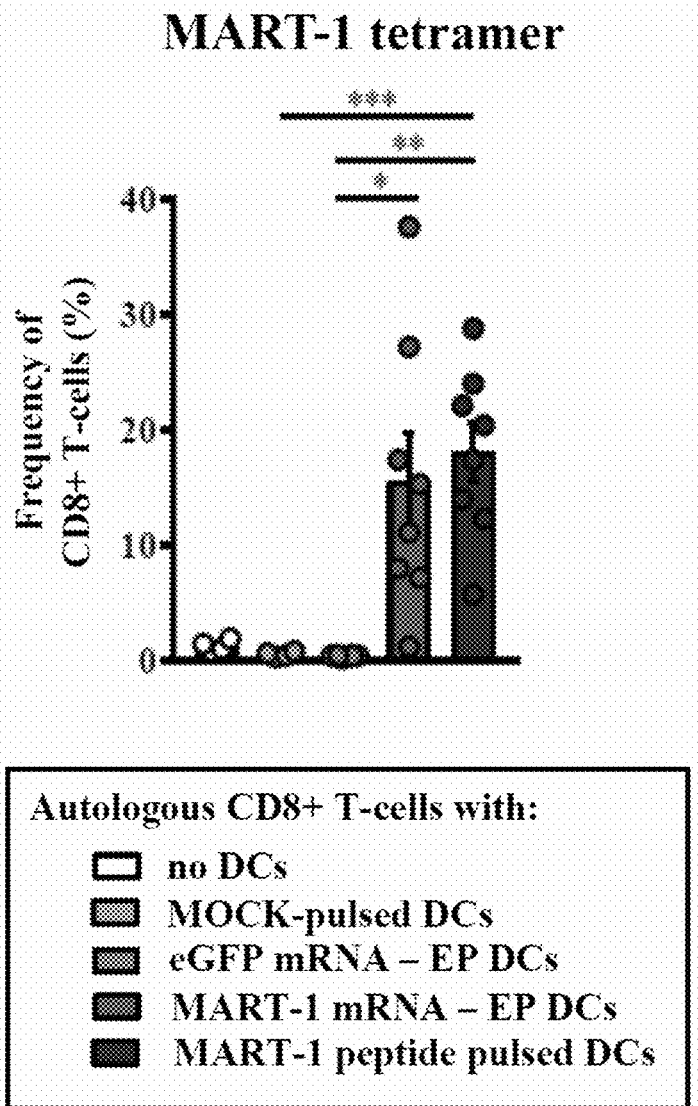

We observed that a total of 2 weekly stimulation rounds with MART-1-mRNA-EP DCs was sufficient to induce a more than 30-fold expansion of antigen-specific (tetramer-positive) CD8+ T-cells compared to stimulation with DCs loaded with irrelevant antigen (eGFP) (median 0.43% [95% CI: 0.22-0.53]) vs 13.2% [95% CI: 1.21-37.6]). No differences were observed in terms of viability and recovery rate post-electroporation whether 4-day moDCs were electroporated with MART-1 mRNA or eGFP mRNA (data not shown). The expansion of MART-1-specific CD8+ T-cells was in the same order of magnitude than obtained with MART-1 peptide pulsed DCs (positive control) (median 18.9% [95% CI: 5.75-28.8]). These results indicate that MPLA/IFN-γ matured 4-day moDCs were able to extract immunogenic epitopes from electroporated MART1-encoding mRNA, for efficient presentation to Ag-specific autologous CD8+ T-cells (FIG. 7A-B).

Figure 7C:
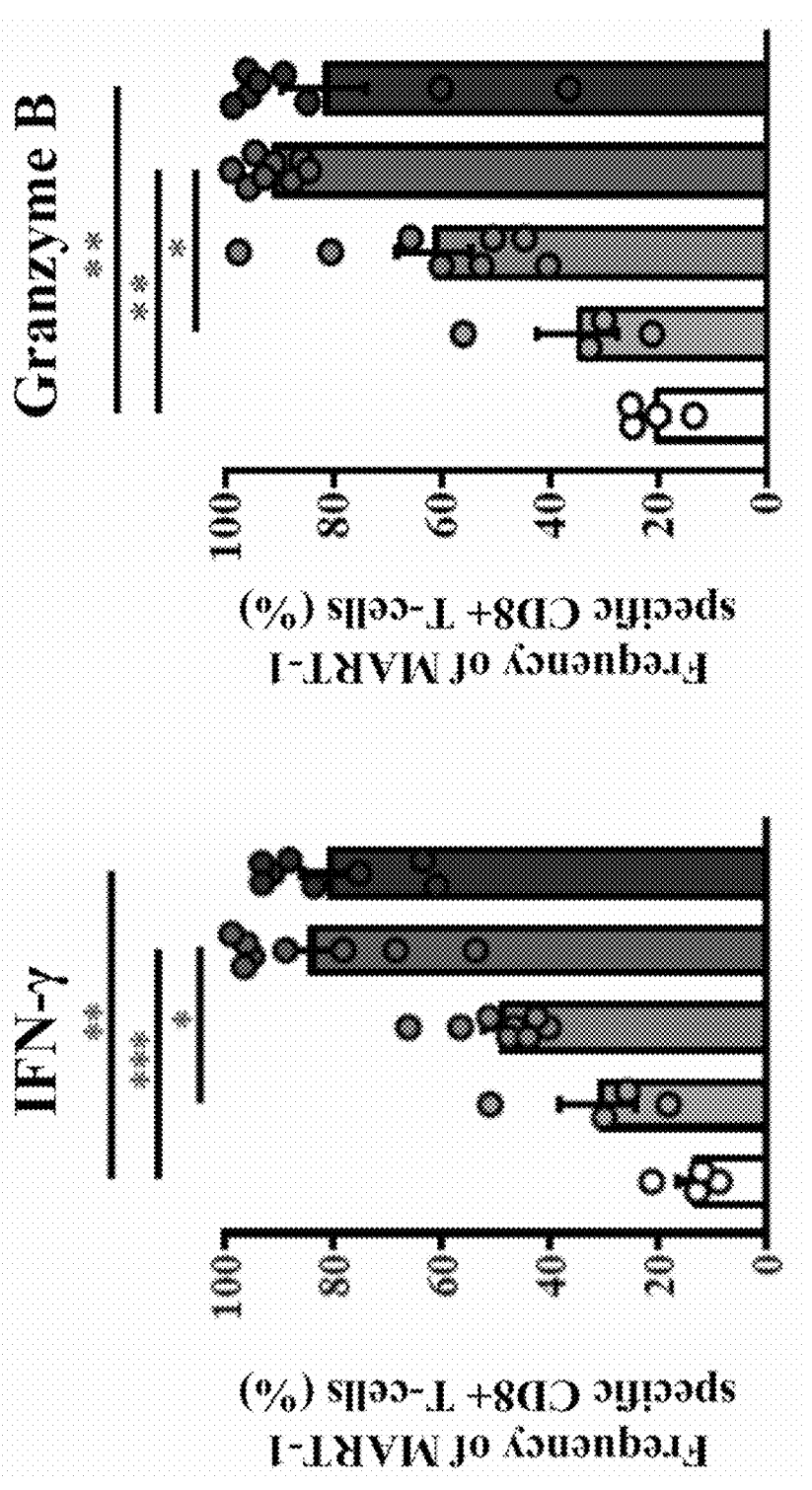

To evaluate the effector potential of the stimulated CD8+ T-cells we combined tetramer detection with IC staining for IFN-γ and granzyme B. We found MART-1-mRNA-EP 4-day moDCs induced the highest numbers of IFN-γ- and granzyme B-producing antigen-specific CD8+ T-cells, compared to negative control conditions (i.e. stimulation with MOCK-pulsed- or eGFP mRNA-EP-DCs, or no DCs) (FIG. 7C).

Figure 8A:
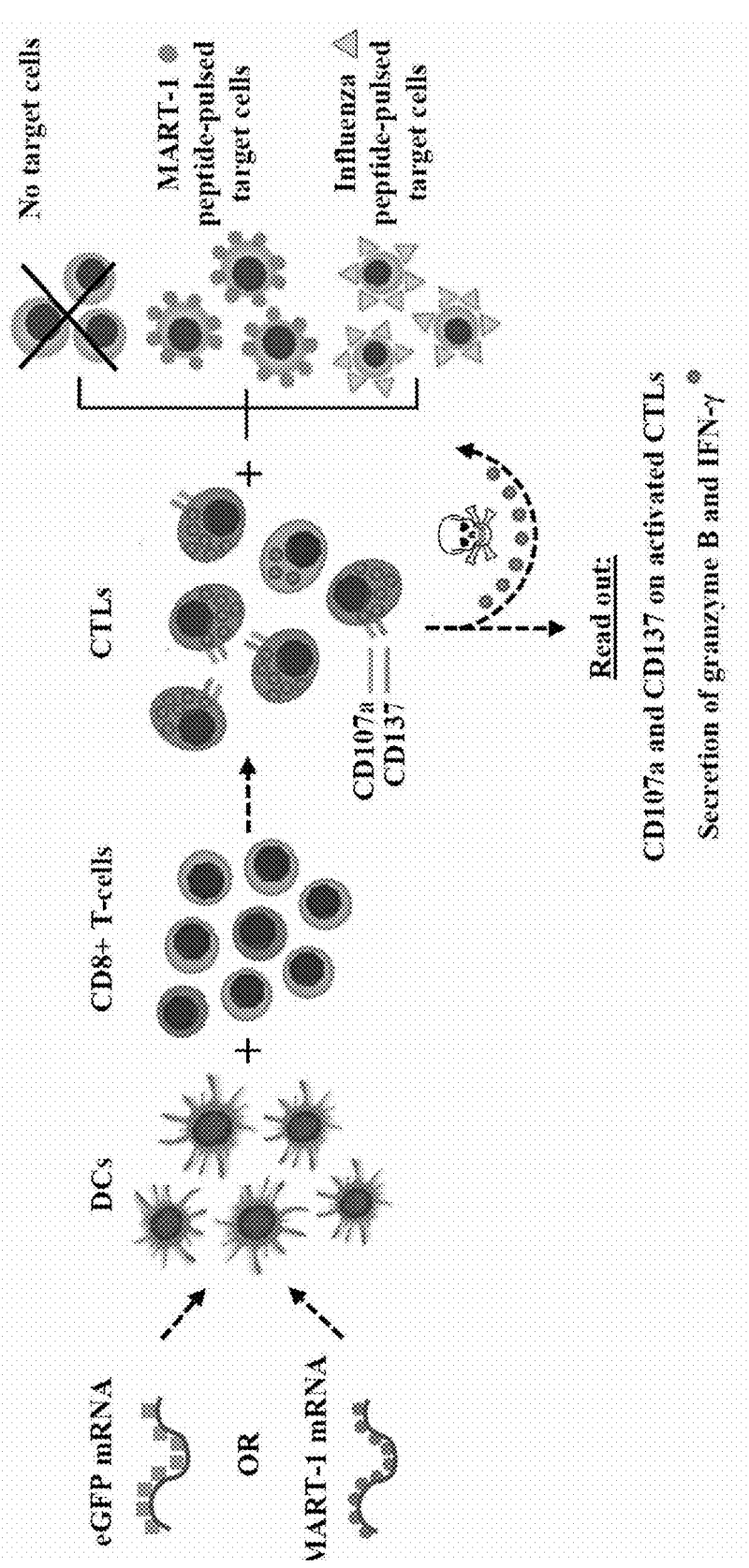
FIG. 8. (A) Schematic overview of the antigen-specific cytotoxicity assay following autologous DC:CD8 T-cell co-culture using HLA-A2+ donors and MART-1 as a model antigen. After 2 weekly rounds of stimulation with autologous 4d-moDC, cytolytic CD8+ T-cells were co-cultured with either no T2 target cells, irrelevant peptide pulsed T2 target cells (influenza peptide) or MART-1 peptide pulsed T2 target cells. The DC counterpart included negative control DCs (MOCK-pulsed DCs (not shown) and eGFP mRNA-EP DCs), MART-1 mRNA-EP DCs and positive control DCs (pulsed with the AAAGIGILTV peptide from MART-1 (not shown)). Cytolytic activity of CD8+ T-cells was characterized by the simultaneous upregulation of the degranulation marker CD107a and the activation marker CD137 in combination with secretion of granzyme B and IFN-γ. (B) CD8+ T-cells previously stimulated by the indicated DC conditions, with representative dotplots showing CD107a/CD137 expression after co-culture with MART-1 peptide-loaded T2 cells. (C) Cytotoxic activity of autologous CD8+ T-cells (CD107a/CD137 expression) according to previous DC stimulation and type of T2 target cells (n=4 to 8 replicates pooled from repeat experiments with 2 different HLA-A2-positive donors). Statistics: 2-way ANOVA with Tukey's multiple comparisons test.
Figure 8B:
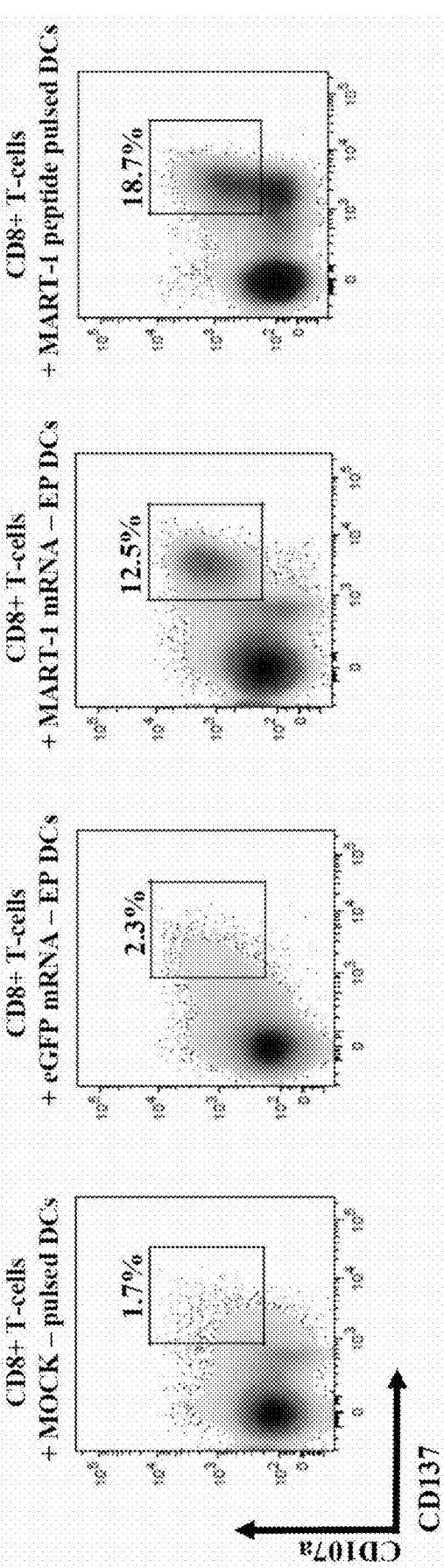
Figure 8C:
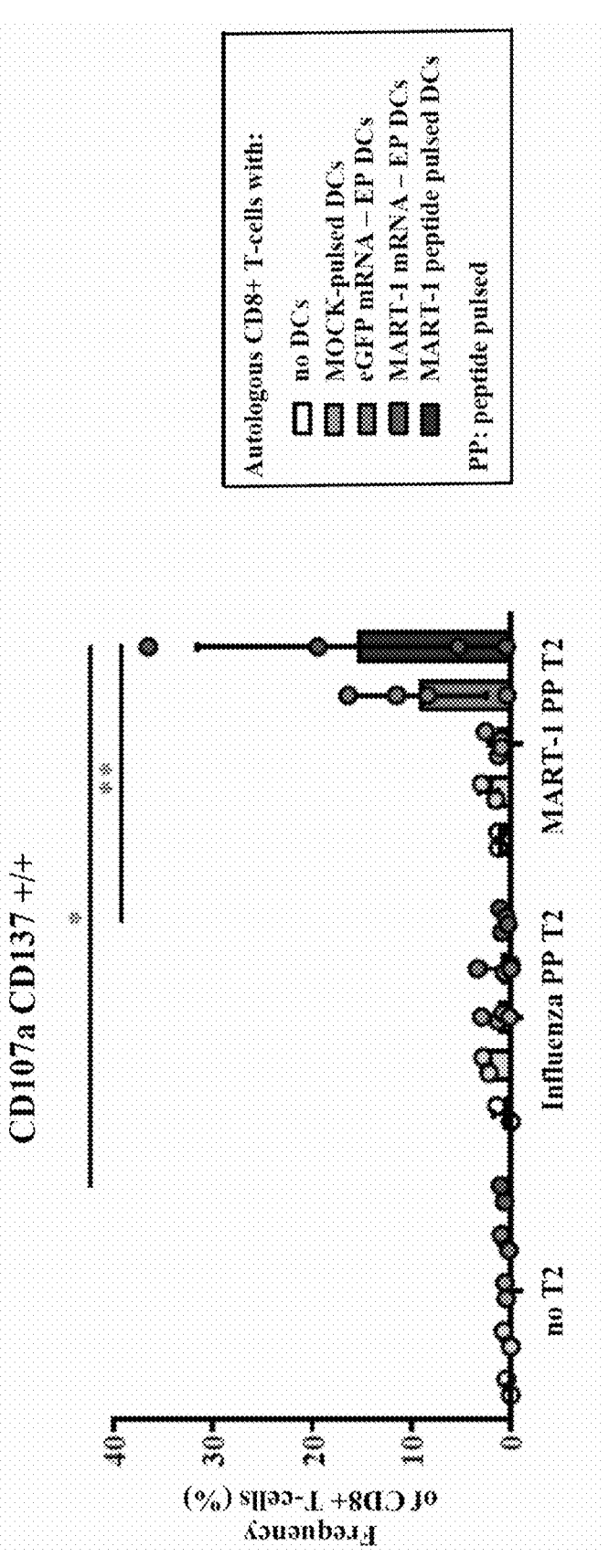

To further assess the cytolytic capacity of 4-day moDC-stimulated CD8+ T-cells, we used the TAP-deficient, HLA-A2+ T2 cells as targets loaded passively with an A2-restricted MART-1 peptide, vs irrelevant (Flu) peptide (experimental set up illustrated in FIG. 8A). Flow cytometry analysis looking at double expression of the T-cell activation marker CD137/4-1BB along with the cytolytic degranulation marker CD107a was used to detect target engagement and killing activity, as described previously (Bonehill et al. 2009). We observed that only CD8+ T-cells stimulated with MART-1-mRNA-loaded and MART-1 peptide pulsed 4-day moDCs during 2 weeks upregulated CD137/CD107a following contact with MART-1-peptide loaded T2-cells (representative dot plots in FIG. 8B). This signal was detected in most of the donors and was specific, as engagement of irrelevant targets (Flu-peptide-loaded T2 cells) did not induce cytolytic marker expression, nor did prior stimulation of the effector CD8+ T-cells with MOCK-pulsed or eGFP-mRNA-electroporated DCs (FIG. 8C).

Discussion

To our knowledge, this is the first description of an accelerated in vitro cell differentiation method allowing the production of clinical-grade DCs with strong Th1 polarizing capacity, combined with efficient presentation of mRNA-encoded tumor antigen introduced by electroporation.

The feasibility of shortening the classical 7-8 day in vitro culture to produce fully mature DCs has been described by other groups in the past. Often termed "fast-DCs", cells obtained after a monocyte-to-DC differentiation time of 24 (Dauer et al. 2003; Kvistborg et al. 2009; Jarnjak-Jankovic et al. 2007) to 72 hours (Truxova et al. 2014) in the presence of GM-CSF and IL-4, followed by a maturation period of 24 hours using either the standard inflammatory cytokine cocktail TNF-α, IL-1β, IL-6, PGE2 or TLR ligands (Truxova et al. 2014), performed equally compared to classical long-term DC cultures in terms of maturation profile and functionality. Only one report described the integration of MPLA+IFN-γ as maturation cocktail in an accelerated DC-differentiation protocol, as part of a comparative study using 4 different maturation strategies after a monocyte-to-DC-differentiation period of 24-36 hours (Massa et al. 2013). Compared to DCs matured with the classical cocktail of TNF-α+IL-1β+IL-6+PGE2 or the alternatives TNF-α+IL-1β+IFN-α+IFN-γ+poly(I:C) or TNF-α+IL-1β+IFN-γ+CL097, MPLA+IFN-γ-matured DCs expressed the highest levels of costimulatory molecule expression and generated the best ratio of IL-12p70/IL-10 release.

Studies performed by Ten Brinke et al (2007; 2010) also documented the use of MPLA/IFN-γ in terms of type 1-polarizing potency, albeit using a 6-7 day culture time. The present invention demonstrates that MPLA/IFN-γ can drive full maturation of DCs when applied to an accelerated culture protocol as well (FIG. 1D; 2B). In addition we demonstrate that the combination of both agents is necessary to induce maximal expression of key T-cell costimulatory molecules such as CD86, CD40 and CD70 as well as of the lymph node-homing chemokine receptor CCR7 (FIG. 3). Of these, CD40 and CD70 upregulation was consistently higher than obtained using 8-day DCs matured with a complex inflammatory cocktail. Sufficient levels of both molecules are essential in anti-tumor immune responses: CD40 is central in facilitating T helper cell-DC activation allowing downstream optimal stimulation of CD8+ cytotoxic T lymphocytes, while CD70 is pivotal in driving Th1 rather than T-reg or Th17 T-cell differentiation and for endowing CD8+ T-cells with effector and memory characteristics. Accordingly, tapping into the potential of the CD40/CD40 L and CD70/CD27 axes has been successfully exploited as a strategy to increase DC immunogenicity for clinical cancer vaccine applications.

We were surprised to detect lower levels of the T-cell coinhibitory receptor PD-L1 on MPLA/IFN-γ-matured DCs vs TNF-α/PGE2 DCs (FIG. 2B). Strikingly, the difference in PD-L1 expression levels at harvest further increases after cryopreservation/thawing (FIG. 10), i.e. the biological formulation that will effectively be administered to the patient, where expression of this immunosuppressive ligand should be as low as possible. Although type-2 interferon is a prototypical inducer of PD-L1 expression on many cell types (Gato-Canas et al. 2017), PGE2 has been described as a powerful driver of PD-L1 upregulation on myeloid cells, as was shown to be the case in tumor-associated myeloid cells with immunosuppressive capacity (Prima et al. 2017). The use of PGE2 in DC culture protocols has usually been motivated by its capacity to induce optimal expression of CCR7 on DCs, maximizing the efficiency of migration into T-cell dependent areas of lymphoid tissue. However, in the present invention 4-day MPLA/IFN-γ DCs expressed at least as much CCR7 as TNF-α/PGE2-matured DCs. Combined with the IL-12 suppression seen in our TNF-α/PGE2-matured DCs (FIG. 6A), altogether these findings strongly support a move away from the classical DC maturation cocktail for next-generation DC-based cancer vaccines.

Further confirming the capacity of 4-day MPLA/IFN-γ-matured DCs to support type-1 polarized immune responses is the profile of chemokines released after cryopreservation, thawing and further 24 hour culture in cytokine-free medium (FIG. 6A). Compared to 8-day TNF-α/PGE2-matured DCs, only 4-day MPLA/IFN-γ-matured DCs secreted high levels of the Th1-attracting chemokines CCL3, CCL4, CCL5, CXCL9, and CXCL10. In vivo, interactions between DC-secreted CXCL10 and CXCR3 receptor expression on CD4+ T-cells were shown to ensure the formation of stable contacts between these cell types in the lymph nodes. This stable cell-contact in combination with the placement of these CD4+ T-cells into potential niches of high IFN-v production, can further promote Th1-differentiation. Additionally, our experiments show the T-reg and Th2-mobilizing chemokine CCL17 to be predominantly released by 8-day TNF-α/PGE2-matured DCs, possibly as a consequence of PGE2 preconditioning. Although statistical significance was not reached, there was also a trend towards higher release of Th17- and T-reg-attracting chemokine CCL20 by 4-day MPLA/IFN-γ-matured DCs. The fact that the choice in DC maturation stimuli defines the Th1- or Th2-T-cell mobilization profile, has already been documented by Lebre et al (2005). In their tests, chemokine production of freshly harvested mature DCs was assessed in response to CD40 ligation. DCs matured in the presence of LPS and IFN-γ were shown to predominantly release Th1-attracting chemokines, whereas the expression level of the Th2-associated chemokine CCL22 significantly increased when PGE2 was present in the maturation cocktail. In contrast to our findings, the expression pattern of CCL17 was not dependent on DC type in the paper of Lebre et al.

An additional factor potentially influencing the level of DC maturation achieved is the physical property of the culture container used. By the method of the present invention it is feasibly to differentiate and activate the cells in gas-permeable bags which constitutes a closed system, compatible with clinically certified immunomagnetic isolation systems. Our results contradict earlier studies indicating that DCs generated in clinical grade bags have an impaired maturation program with downregulated costimulatory molecule expression, chemokines and IL-12 secretion (Rouas et al. 2010). Surprisingly, we show that all these features are induced in our DCs and even intact after cryopreservation, thawing and further culture in cytokine-free base medium. Similar studies were performed by the groups of G. Gaudernack et al and G. Kvalheim et al (Kyte et al. 2005; Mu et al. 2003), reinforcing the idea that clinical-grade DCs with intact immunogenic properties can indeed be generated in bags. Culturing in cell differentiation bags will also allow us to easily transpose our method to commercially available, fully automated closed cell culture systems. This option will enable further reduction in operator interventions, decrease contamination risk, and increase overall reproducibility.

The present invention further differentiates itself from earlier reports focusing on alternative culture duration and/ or maturation protocols by selecting mRNA electroporation as the way to load DCs with antigen. The advantages of this technique is flexibility in terms of synthetizing customized sequences encoding for tumor-associated antigens or sequences containing mutation-derived neo-epitopes, with the option to incorporate sequences to optimize both MHCI and MHCII presentation. Also, in contrast to previous studies where DCs are passively loaded with selected, HLA-restricted peptides, electroporation with full-length mRNA ensures processing and potential presentation of a broad array of epitopes without imposing any patient pre-selection in terms of HLA-type. Moreover, the half-life of translated proteins in the DC ensures prolonged generation of MHC I-epitope complexes while passively loaded exogenous peptides are only transiently bound to surface HLA molecules or depleted by internalization. The capacity of DCs electroporated with mRNA to induce T-cell responses as robust as peptide-loaded DCs has been demonstrated earlier. Here we show that 4-day cultured, MPLA/IFN-γ-matured DCs electroporated with a model tumor-associated antigen can induce a vigorous expansion of rare antigen-specific CD8+ T-cells equipped with the necessary anti-tumoral toolkit (e.g. high expression of IFN-γ and perforin), which is reflected by efficient and highly specific cytotoxic activity. Importantly, we evaluated this essential DC property after cryopreservation and thawing, which reflects a real-life vaccination setting.

In conclusion, the present invention demonstrates the superiority of 4-day MPLA/IFN-γ-matured monocyte-derived DCs over "classical" 8-day TNF-α/PGE2-matured DCs in terms of cellular yield, phenotype, and type-1 polarizing profile. Reducing culturing time, using GMP-compliant materials and serum-free culturing medium in a closed-system, electroporation and cryopreservation did not impair the capacity of short-cultured MPLA/IFN-γ-DCs to induce cytolytic tumor-derived antigen specific CD8+ T-cell responses, which further underscores the robustness of this production method for clinical implementation.

REFERENCES

H. Jonuleit, U. Kuhn, G. Muller, K. Steinbrink, L. Paragnik, et al, Pro-inflammatory cytokines and prostaglandins induce maturation of potent immunostimulatory dendritic cells under fetal calf serum-free conditions, European journal of immunology 27 (12) (1997) 3135-42.

P. Kalinski, J. H. Schuitemaker, C. M. Hilkens, M. L. Kapsenberg, Prostaglandin E2 induces the final maturation of IL-12-deficient CD1a+CD83+ dendritic cells: the levels of IL-12 are determined during the final dendritic cell maturation and are resistant to further modulation, Journal of immunology (Baltimore, Md.: 1950) 161 (6) (1998) 2804-9.

R. B. Mailliard, A. Wankowicz-Kalinska, Q. Cai, A. Wesa, C. M. Hilkens, M. L. Kapsenberg, et al, alpha-type-1 polarized dendritic cells: a novel immunization tool with optimized CTL-inducing activity, Cancer research 64 (17) (2004) 5934-7.

H. Okada, P. Kalinski, R. Ueda, A. Hoji, G. Kohanbash, T. E. Donegan, et al, Induction of CD8+ T-cell responses against novel glioma associated antigen peptides and clinical activity by vaccinations with {alpha}-type 1 polarized dendritic cells and polyinosinic-polycytidylic acid stabilized by lysine and carboxymethylcellulose in patients with recurrent malignant glioma, Journal of clinical oncology: official journal of the American Society of Clinical Oncology 29 (3) (2011) 330-6.

C. Paustian, R. Caspell, T. Johnson, P. A. Cohen, S. Shu, S. Xu, et al, Effect of multiple activation stimuli on the generation of Th1-polarizing dendritic cells, Human immunology 72 (1) (2011) 24-31.

C. Boccaccio, S. Jacod, A. Kaiser, A. Boyer, J. P. Abastado, A. Nardin, Identification of a clinical-grade maturation factor for dendritic cells, Journal of immunotherapy (Hagerstown, Md. 1997) 25(1) (2002) 88-96.

A. G. Johnson, M. Tomai, L. Solem, L. Beck, E. Ribi, Characterization of a nontoxic monophosphoryl lipid A, Reviews of infectious diseases 9 Suppl 5 (1987) S512-6.

K. A. Gregg, E. Harberts, F. M. Gardner, M. R. Pelletier, C. Cayatte, et al Rationally Designed TLR4 Ligands for Vaccine Adjuvant Discovery, mBio 8 (3) (2017).

M. Hansen, G. M. Hjorto, M. Donia, O. Met, N. B. Larsen, M. H. Andersen, et al, Comparison of clinical grade type 1 polarized and standard matured dendritic cells for cancer immunotherapy, Vaccine 31(4) (2013) 639-46.

A. Ten Brinke, M. L. Karsten, M. C. Dieker, J. J. Zwaginga, S. M. van Ham, The clinical grade maturation cocktail monophosphoryl lipid A plus IFNgamma generates monocyte-derived dendritic cells with the capacity to migrate and induce Th1 polarization, Vaccine 25(41) (2007) 7145-52.

A. ten Brinke, G. van Schijndel, R. Visser, T. D. de Gruijl, J. J. Zwaginga, S. M. van Ham, Monophosphoryl lipid A plus IFNgamma maturation of dendritic cells induces antigen-specific CD8+ cytotoxic T cells with high cytolytic potential, Cancer Immunol Immunother 59(8) (2010) 1185-95.

S. T. Kolanowski, L. Sritharan, S. N. Lissenberg-Thunnissen, G. M. Van Schijndel, S. M. Van Ham, A. ten Brinke, Comparison of media and serum supplementation for generation of monophosphoryl lipid A/interferon-gamma-matured type I dendritic cells for immunotherapy, Cytotherapy 16(6) (2014) 826-34.

S. Van Lint, S. Wilgenhof, C. Heirman, J. Corthals, K. Breckpot, A. Bonehill, et al, Optimized dendritic cell-based immunotherapy for melanoma: the TriMix-formula, Cancer Immunol Immunother 63(9) (2014) 959-67.

S. Tuyaerts, A. Michiels, J. Corthals, A. Bonehill, C. Heirman, C. de Greef, et al, Induction of Influenza Matrix Protein 1 and MelanA-specific T lymphocytes in vitro using mRNA-electroporated dendritic cells, Cancer gene therapy 10(9) (2003) 696-706.

P. Ponsaerts, V. F. Van Tendeloo, Z. N. Berneman, Cancer immunotherapy using RNA-loaded dendritic cells, Clinical and experimental immunology 134(3) (2003) 378-84.

A. Bonehill, C. Heirman, S. Tuyaerts, A. Michiels, K. Breckpot, F. Brasseur, et al, Messenger RNA-electroporated dendritic cells presenting MAGE-A3 simultaneously in HLA class I and class II molecules, Journal of immunology (Baltimore, Md.: 1950) 172(11) (2004) 6649-57.

S. Jarnjak-Jankovic, H. Hammerstad, S. Saeboe-Larssen, G. Kvalheim, G. Gaudernack, A full scale comparative study of methods for generation of functional Dendritic cells for use as cancer vaccines, BMC cancer 7 (2007), 119.

M. Dauer, B. Obermaier, J. Herten, C. Haerle, K. Pohl, S. Rothenfusser, et al, Mature dendritic cells derived from human monocytes within 48 hours: a novel strategy for dendritic cell differentiation from blood precursors, Journal of immunology (Baltimore, Md.: 1950) 170(8) (2003) 4069-76.

P. Kvistborg, M. Boegh, A. W. Pedersen, M. H. Claesson, M. B. Zocca, Fast generation of dendritic cells, Cellular immunology 260 (1) (2009) 56-62.

C. Massa, B. Seliger, Fast dendritic cells stimulated with alternative maturation mixtures induce polyfunctional and long-lasting activation of innate and adaptive effector cells with tumor-killing capabilities, Journal of immunology (Baltimore, Md.: 1950) 190(7) (2013) 3328-37.

I. Truxova, K. Pokorna, K. Kloudova, S. Partlova, R. Spisek, J. Fucikova, Day 3 Poly (I:C)-activated dendritic cells generated in CellGro for use in cancer immunotherapy trials are fully comparable to standard Day 5 DCs, Immunol Lett 160(1) (2014) 39-49.

A. Van Driessche, A. L. Van de Velde, G. Nijs, T. Braeckman, B. Stein, J. M. De Vries, et al, Clinical-grade manufacturing of autologous mature mRNA-electroporated dendritic cells and safety testing in acute myeloid leukemia patients in a phase I dose-escalation clinical trial, Cytotherapy 11(5) (2009) 653-68.

L. Colantonio, H. Recalde, F. Sinigaglia, D. D'Ambrosio, Modulation of chemokine receptor expression and chemotactic responsiveness during differentiation of human naive T cells into Th1 or Th2 cells, European journal of immunology 32(5) (2002) 1264-73.

J. R. Groom, A. D. Luster, CXCR3 ligands: redundant, collaborative and antagonistic functions, Immunology and cell biology 89(2) (2011) 207-15.

M. Samson, G. LaRosa, F. Libert, P. Paindavoine, M. Detheux, G. Vassart, et al, The second extracellular loop of CCR5 is the major determinant of ligand specificity, The Journal of biological chemistry 272(40) (1997) 24934-41.

O. Yoshie, K. Matsushima, CCR4 and its ligands: from bench to bedside, International immunology 27(1) (2015) 11-20.

T. Yamazaki, X. O. Yang, Y. Chung, A. Fukunaga, R. Nurieva, B. Pappu, et al, CCR6 regulates the migration of inflammatory and regulatory T cells, Journal of immunology (Baltimore, Md.: 1950) 181(12) (2008) 8391-401.

A. Bonehill, A. M. Van Nuffel, J. Corthals, S. Tuyaerts, C. Heirman, V. Francois, et al, Single-step antigen loading and activation of dendritic cells by mRNA electroporation for the purpose of therapeutic vaccination in melanoma patients, Clinical cancer research: an official journal of the American Association for Cancer Research 15(10) (2009) 3366-75.

M. Gato-Canas, M. Zuazo, H. Arasanz, M. Ibanez-Vea, L. Lorenzo, G. Fernandez-Hinojal, et al, PDL1 Signals through Conserved Sequence Motifs to Overcome Interferon-Mediated Cytotoxicity, Cell reports 20(8) (2017) 1818-1829.

V. Prima, L. N. Kaliberova, S. Kaliberov, D. T. Curiel, S. Kusmartsev, COX2/mPGES1/PGE (2) pathway regulates PD-L1 expression in tumor-associated macrophages and myeloid-derived suppressor cells, P Natl Acad Sci USA 114(5) (2017) 1117-1122.

M. C. Lebre, T. Burwell, P. L. Vieira, J. Lora, A. J. Coyle, M. L. Kapsenberg, et al, Differential expression of inflammatory chemokines by Th1- and Th2-cell promoting dendritic cells: a role for different mature dendritic cell populations in attracting appropriate effector cells to peripheral sites of inflammation, Immunology and cell biology 83(5) (2005) 525-35.

R. Rouas, H. Akl, H. Fayyad-Kazan, N. El Zein, B. Badran, B. Nowak, et al, Dendritic cells generated in clinical grade bags strongly differ in immune functionality when compared with classical DCs generated in plates, Journal of immunotherapy (Hagerstown, Md.: 1997) 33(4) (2010) 352-63.

J. A. Kyte, G. Kvalheim, S. Aamdal, S. Saeboe-Larssen, G. Gaudernack, Preclinical full-scale evaluation of dendritic cells transfected with autologous tumor-mRNA for melanoma vaccination, Cancer gene therapy 12(6) (2005) 579-591.

L. J. Mu, G. Gaudernack, S. Saeboe-Larssen, H. Hammerstad, A. Tierens, G. Kvalheim, A protocol for generation of clinical grade mRNA-transfected monocyte-derived dendritic cells for cancer vaccines, Scandinavian journal of immunology 58(5) (2003) 578-86.

Valmori D, Gervois N, Rimoldi D, Fonteneau J F, Bonelo A, Liénard D, Rivoltini L, Jotereau F, Cerottini J C, Romero P. Diversity of the fine specificity displayed by HLA-A*0201-restricted CTL specific for the immunodominant Melan-A/MART-1 antigenic peptide. J Immunol. 1998 Dec. 15;161(12):6956-62.

The invention claimed is:

1. A method for manufacturing mature, clinical grade autologous dendritic cells (DCs), said method comprising:

culturing dendritic cell precursors for about 48 to 96 hours in a closed culture system in the presence of granulo-cyte-macrophage colony-stimulating factor (GM-CSF) and interleukin-4 (IL-4);

contacting the immature DCs for the last 20 to 28 hours of the culturing step with Interferon gamma (IFN-g) and monophosphoryl lipid A (MPLA), under culture conditions suitable for maturation of the immature DCs to form a mature DC population;

harvesting the mature DCs; and transfecting the mature DCs with antigen-encoding mRNA before or after harvest of the mature DCs.

2. The method according to claim 1, wherein the dendritic cell precursors are isolated by collecting heparinized blood; apheresis or leukapheresis; preparation of buffy coats; roset-ting; centrifugation; density gradient centrifugation; differ-ential lysis of cells; filtration; elutriation; fluorescence-activated cell sorting; or immunomagnetic isolation.

3. The method according to claim 1, wherein the dendritic cell precursors are monocytes.

4. The method according to claim 1, wherein the closed culture system comprises good manufacturing practice (GMP)-compliant cell culture bags.

5. The method according to claim 4, wherein cell density in said culture bags at initiation of cell culture ranges from 0.5 to $2\times10^6$ cells/mL.

6. The method according to claim 1, wherein the concen-tration of said GM-CSF, IL-4 and/or IFN-g is between 500 and 2500 U/ml.

7. The method according to claim 1, wherein the concen-tration of said MPLA is between 1-20 µg/ml.

8. The method according to claim 1, wherein the trans-fection is performed by electroporation, photoporation, lipo-fection, viral vector systems, incubation of naked nucleic acids or fusion of DCs with infected cells or tumor cells.

9. The method according to claim 1, wherein the trans-fection is performed by electroporation.

10. The method according to claim 9, wherein the elec-troporation is by exponential decay pulse, square wave pulse, or time constant.

11. The method according to claim 1, wherein the trans-fected DCs are further resuspended in a cryopreservation medium and, optionally, are stored in the vapor phase of a liquid nitrogen container.

12. The method according to claim 1, wherein the antigen encoded by the antigen-encoding mRNA is selected from the group consisting of a tumor antigen, a tumor-associated antigen, a cancer-testis antigen, a mutanome-derived anti-gen, an oncogenic viral antigen, a bacterial antigen, a yeast antigen, a parasitic antigen, and a fungal antigen.

13. The method of claim 1, wherein the method comprises a total in vitro culture duration of about 3 days.

14. The method of claim 1, wherein the method is carried out without antibiotic supplementation.

15. Mature dendritic cells obtained by a method compris-ing the following steps:

culturing dendritic cell precursors for about 48 to 96 hours in the presence of granulocyte-macrophage colony-stimulating factor (GM-CSF) and interleukin-4 (IL-4);

contacting the immature DCs for the last 20 to 28 hours of the culturing step with Interferon gamma (IFN-g) and monophosphoryl lipid A (MPLA), under culture conditions suitable for maturation of the immature DCs to form a mature DC population;

harvesting the mature DCs; and transfecting the mature DCs with antigen-encoding mRNA before or after harvest of the mature DCs.

16. The mature dendritic cells according to claim 15, wherein said dendritic cells are further cryopreserved.

17. A pharmaceutical composition or vaccine comprising the mature, transfected dendritic cells according to claim 15, and a pharmaceutical acceptable carrier and/or excipient.

18. The pharmaceutical composition according to claim 17, wherein the composition is an aqueous isotonic sterile injection solution comprising an antioxidant, a buffer, a bacteriostat, or a solute that renders the formulation isotonic with the blood of the intended recipient.

19. The pharmaceutical composition according to claim 17, wherein the composition is an aqueous or non-aqueous sterile suspension comprising a suspending agent, a solubi-lizer, a thickening agent, a stabilizer, a preservative, an immunostimulant, a cytokine, or an adjuvant.

20. The pharmaceutical composition according to claim 17, wherein said composition is cryopreserved.

21. A method of eliciting an immune response against an antigen, said method comprising administering a mature antigen-loaded dendritic cell or a composition comprising a mature antigen-loaded dendritic cell, wherein the mature antigen-loaded dendritic cell is prepared according to the method of claim 1.

22. A method of prophylactically or therapeutically vac-cinating a subject against a disease selected from the group of malignant disorders, non-malignant disorders or infec-tious diseases, said method comprising administering a mature antigen loaded dendritic cell or composition com-prising it, wherein the mature dendritic cell is prepared according to the method of claim 1.

23. The method according to claim 21, wherein the mature antigen loaded dendritic cell or composition comprising it is administered to the subject by injection, by continuous infusion, or sustained release from implants.

24. The method according to claim 21, wherein the mature antigen loaded dendritic cell or composition comprising it is administered to the subject at two to four week intervals.

* * * * *

SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Synthetic HLA-A*201-restricted peptide from
      MART-1

<400> SEQUENCE: 1

Ala Ala Ala Gly Ile Gly Ile Leu Thr Val
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic A2-restricted peptide from influenza
      matrix protein -continued <400> SEQUENCE: 2

Gly Ile Leu Gly Phe Val Phe Thr Leu
1               5